: US 8,034,065 B2
(45) Date of Patent: Oct. 11, 2011

(12) United States Patent
Coe et al.

(54) CONTROLLING PRESSURE IN ADJUSTABLE RESTRICTION DEVICES

(75) Inventors: Jonathan A. Coe, Cincinnati, OH (US); Thomas E. Adams, Maineville, OH (US); Mark D. Overmyer, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 702 days.

(21) Appl. No.: 12/037,261

(22) Filed: Feb. 26, 2008

(65) Prior Publication Data
US 2009/0216255 A1 Aug. 27, 2009

(51) Int. Cl.
*A61B 17/08* (2006.01)
(52) U.S. Cl. .................. 606/157; 251/5; 604/99.01
(58) Field of Classification Search .......... 606/157–158, 606/191–202; 251/5; 604/19, 48, 93.01, 604/96.01, 99.04, 99.01; 600/29–31, 37
See application file for complete search history.

(56) References Cited

U.S. PATENT DOCUMENTS

| RE3,036 E | 7/1868 | Shunk |
|---|---|---|
| RE3,037 E | 7/1868 | Tucker |
| RE3,115 E | 9/1868 | Lewis |
| RE3,187 E | 11/1868 | Winchester |
| RE3,322 E | 3/1869 | Murch |
| 236,373 A | 1/1881 | Spilman |
| 322,388 A | 7/1885 | Lord |
| 400,401 A | 3/1889 | Gutzkow |
| D23,637 S | 9/1894 | Casad |
| D24,900 S | 11/1895 | Clemecet |
| D25,318 S | 3/1896 | Perky |
| D27,151 S | 6/1897 | Moulten |
| D29,715 S | 11/1898 | Wheeler |
| D29,745 S | 11/1898 | Bunker |
| D29,885 S | 12/1898 | Gillespie et al. |
| D30,690 S | 5/1899 | Schwedtmann |
| D30,966 S | 6/1899 | Howe |

(Continued)

FOREIGN PATENT DOCUMENTS
CA       1059035       7/1979
(Continued)

OTHER PUBLICATIONS

European Search Report, Application No. 09250497.6, Issued May 13, 2009, 11 pages.

(Continued)

*Primary Examiner* — Corrine M McDermott
*Assistant Examiner* — Mark Mashack
(74) *Attorney, Agent, or Firm* — Nutter McClennen & Fish LLP

(57) ABSTRACT

Methods and devices are provided for regulating a hydraulic restriction system. In general, the methods and devices can allow for non-invasive pressure control using a flow control mechanism. The flow control mechanism can be disposed between an implantable restriction device and a fluid source and include an adjustable, variably-sized fluid communication member in fluid communication with the restriction device and the fluid source. The geometry of the fluid communication member can control a rate of fluid flow between the restriction device and the fluid source, thereby also regulating a rate at which a pressure of fluid within the restriction device changes. Alternatively, the fluid flow control mechanism can include a biasing mechanism that can control the rate of fluid flow between the restriction device and the fluid source.

7 Claims, 14 Drawing Sheets

U.S. PATENT DOCUMENTS

| | | | |
|---|---|---|---|
| D31,230 S | 7/1899 | Hogan |
| 689,758 A | 12/1901 | Shaw |
| 724,913 A | 4/1903 | Montgomery |
| 899,477 A | 9/1908 | Williams |
| 926,197 A | 6/1909 | Kim |
| 953,875 A | 4/1910 | Waring |
| 991,192 A | 5/1911 | Battenfeld |
| 1,087,988 A | 2/1914 | Sheldon |
| 1,210,701 A | 1/1917 | Ryden |
| 1,219,296 A | 3/1917 | Hahn |
| 1,224,355 A | 5/1917 | Brown |
| 1,263,914 A | 4/1918 | Martin |
| 1,310,290 A | 7/1919 | Piechowicz |
| 1,384,873 A | 7/1921 | Strickland |
| 1,421,507 A | 7/1922 | Lindberg |
| 1,551,525 A | 8/1925 | Hamer |
| 1,560,973 A | 11/1925 | Cheron |
| 1,620,633 A | 3/1927 | Colvin |
| 1,623,403 A | 4/1927 | Friel |
| 1,689,085 A | 10/1928 | Russell et al. |
| 1,764,071 A | 6/1930 | Foulke |
| 1,782,704 A | 11/1930 | Woodruff |
| 1,807,107 A | 5/1931 | Sternberch |
| 1,865,446 A | 7/1932 | Sears |
| 1,882,338 A | 10/1932 | Reed et al. |
| 1,924,781 A | 8/1933 | Gaiser |
| 2,027,875 A | 1/1936 | Odend'hal |
| 2,063,430 A | 12/1936 | Graser |
| 2,099,160 A | 11/1937 | Charch |
| 2,105,127 A | 1/1938 | Petrone |
| 2,106,192 A | 1/1938 | Saville |
| 2,143,429 A | 1/1939 | Auble |
| 2,166,603 A | 7/1939 | Menzer |
| 2,168,427 A | 8/1939 | McConkey |
| 2,174,525 A | 10/1939 | Padernal |
| 2,177,564 A | 10/1939 | Havill |
| 2,178,463 A | 10/1939 | Bahnson |
| 2,180,599 A | 11/1939 | Menasco |
| 2,203,460 A | 6/1940 | Fieber |
| 2,206,038 A | 7/1940 | Lang Ford |
| 2,216,374 A | 10/1940 | Martin |
| 2,223,699 A | 12/1940 | Norgren |
| 2,225,145 A | 12/1940 | Baumbach |
| 2,225,880 A | 12/1940 | Montelius |
| 2,261,060 A | 10/1941 | Giesler |
| 2,261,355 A | 11/1941 | Flynn |
| 2,295,539 A | 9/1942 | Beach |
| 2,303,108 A | 11/1942 | Blackburn |
| 2,303,502 A | 12/1942 | Rous |
| 2,318,819 A | 5/1943 | Verson |
| 2,327,407 A | 8/1943 | Edyvean |
| 2,327,615 A | 8/1943 | Ankarlo |
| 2,354,571 A | 7/1944 | Blain |
| 2,426,392 A | 8/1947 | Fennema |
| 2,426,817 A | 9/1947 | Charlton et al. |
| 2,440,260 A | 4/1948 | Gall |
| 2,442,573 A | 6/1948 | Stafford |
| 2,453,217 A | 11/1948 | Gregg et al. |
| 2,455,859 A | 12/1948 | Foley |
| 2,477,922 A | 8/1949 | Emery et al. |
| 2,478,876 A | 8/1949 | Nelson |
| 2,482,392 A | 9/1949 | Whitaker |
| 2,494,881 A | 1/1950 | Kost |
| 2,509,210 A | 5/1950 | Clark |
| 2,509,673 A | 5/1950 | Church |
| 2,511,765 A | 6/1950 | Bradbury |
| 2,520,056 A | 8/1950 | Pozun |
| 2,521,976 A | 9/1950 | Hays |
| 2,533,924 A | 12/1950 | Foley |
| 2,538,259 A | 1/1951 | Merriman |
| 2,581,479 A | 1/1952 | Grashman |
| 2,600,324 A | 6/1952 | Rappaport |
| 2,606,003 A | 8/1952 | McNeill |
| 2,615,940 A | 10/1952 | Williams |
| 2,632,447 A | 3/1953 | Dobes |
| 2,639,342 A | 5/1953 | Cope |
| 2,640,119 A | 5/1953 | Bradford, Jr. |
| 2,641,742 A | 6/1953 | Wolfe |
| 2,651,304 A | 9/1953 | Browner |
| 2,665,577 A | 1/1954 | Sanowskis |
| 2,673,999 A | 4/1954 | Shey |
| 2,676,609 A | 4/1954 | Pfarrer |
| 2,684,118 A | 7/1954 | Osmun |
| 2,689,611 A | 9/1954 | Martinson |
| 2,697,435 A | 12/1954 | Ray |
| 2,723,323 A | 11/1955 | Niemi |
| 2,734,992 A | 2/1956 | Elliot et al. |
| 2,740,007 A | 3/1956 | Amelang |
| 2,740,853 A | 4/1956 | Hatman, Jr. |
| 2,742,323 A | 4/1956 | Shey |
| 2,747,332 A | 5/1956 | Morehouse |
| 2,753,876 A | 7/1956 | Kurt |
| 2,756,883 A | 7/1956 | Schreck |
| 2,756,983 A | 7/1956 | Furcini |
| 2,761,603 A | 9/1956 | Fairchild |
| 2,773,312 A | 12/1956 | Peck |
| 2,783,728 A | 3/1957 | Hoffmann |
| 2,787,875 A | 4/1957 | Johnson |
| 2,793,379 A | 5/1957 | Moore |
| 2,795,460 A | 6/1957 | Bletcher |
| 2,804,514 A | 8/1957 | Peters |
| 2,822,113 A | 2/1958 | Joiner, Jr. |
| 2,831,478 A | 4/1958 | Uddenberg et al. |
| 2,864,393 A | 12/1958 | Drake |
| 2,865,541 A | 12/1958 | Hicks |
| 2,870,024 A | 1/1959 | McK. Martin |
| 2,875,775 A * | 3/1959 | Cummings ................ 137/155 |
| 2,883,995 A | 4/1959 | Bialous et al. |
| 2,886,355 A | 5/1959 | Wurzel |
| 2,895,215 A | 7/1959 | Neher et al. |
| 2,899,493 A | 8/1959 | Levine |
| 2,902,861 A | 9/1959 | Frost et al. |
| 2,923,531 A | 2/1960 | Bauer et al. |
| 2,924,263 A | 2/1960 | Landis |
| 2,924,432 A | 2/1960 | Arps et al. |
| 2,930,170 A | 3/1960 | Holsman et al. |
| 2,938,592 A | 5/1960 | Charske et al. |
| 2,941,338 A | 6/1960 | Santschi |
| 2,943,682 A | 7/1960 | Ingram, Jr. et al. |
| 2,958,781 A | 11/1960 | Marchal et al. |
| 2,961,479 A | 11/1960 | Bertling |
| 2,976,355 A | 3/1961 | Levine |
| 2,976,686 A | 3/1961 | Stelzer |
| 2,977,876 A | 4/1961 | Meyers |
| 2,986,715 A | 5/1961 | Church et al. |
| 2,989,019 A | 6/1961 | Van Sciver, II |
| 3,010,692 A | 11/1961 | Jentoft |
| 3,013,234 A | 12/1961 | Bourns |
| 3,018,791 A | 1/1962 | Knox |
| 3,034,356 A | 5/1962 | Bieganski |
| 3,039,733 A * | 6/1962 | Mattioli ........................ 251/5 |
| 3,040,800 A | 6/1962 | Hartley |
| 3,054,618 A | 9/1962 | Abrams et al. |
| 3,060,262 A | 10/1962 | Hoer |
| 3,070,373 A | 12/1962 | Mathews et al. |
| 3,082,414 A | 3/1963 | Papaminas |
| 3,085,577 A | 4/1963 | Berman et al. |
| 3,096,410 A | 7/1963 | Anderson |
| 3,099,262 A | 7/1963 | Bigliano |
| 3,125,028 A | 3/1964 | Rohde |
| 3,126,029 A | 3/1964 | Englesson |
| 3,129,072 A | 4/1964 | Cook et al. |
| 3,135,914 A | 6/1964 | Callan et al. |
| 3,144,017 A | 8/1964 | Muth |
| 3,151,258 A | 9/1964 | Sonderegger et al. |
| 3,153,460 A | 10/1964 | Raskin |
| 3,161,051 A | 12/1964 | Perry, Jr. |
| 3,167,044 A | 1/1965 | Henrickson |
| 3,171,549 A | 3/1965 | Orloff |
| 3,172,700 A | 3/1965 | Haas |
| 3,173,269 A | 3/1965 | Imbertson |
| 3,182,494 A | 5/1965 | Beatty et al. |
| 3,187,181 A | 6/1965 | Keller |
| 3,187,745 A | 6/1965 | Baum et al. |
| 3,190,388 A | 6/1965 | Moser et al. |
| 3,205,547 A | 9/1965 | Riekse |
| 3,208,255 A | 9/1965 | Burk |

| | | | | | | |
|---|---|---|---|---|---|---|
| 3,209,570 A | 10/1965 | Hills | | 3,492,638 A | 1/1970 | Lane |
| 3,221,468 A | 12/1965 | Casey | | 3,502,829 A | 3/1970 | Reynolds |
| 3,228,703 A | 1/1966 | Wilson | | 3,503,116 A | 3/1970 | Strack |
| 3,229,684 A | 1/1966 | Nagumo et al. | | 3,504,664 A | 4/1970 | Haddad |
| 3,236,088 A | 2/1966 | Moller | | 3,505,808 A | 4/1970 | Eschle |
| 3,238,624 A | 3/1966 | McCabe | | 3,509,754 A | 5/1970 | Massingill et al. |
| 3,240,510 A | 3/1966 | Spouge | | 3,512,517 A | 5/1970 | Kadish et al. |
| 3,245,642 A | 4/1966 | Dicke | | 3,514,919 A | 6/1970 | Ashton et al. |
| 3,255,568 A | 6/1966 | Martin et al. | | 3,516,220 A | 6/1970 | Buford et al. |
| 3,260,091 A | 7/1966 | Shaw, Jr. | | 3,517,553 A | 6/1970 | Williams et al. |
| 3,265,822 A | 8/1966 | Moulten | | 3,527,226 A | 9/1970 | Hakin et al. |
| 3,266,487 A | 8/1966 | Watkins et al. | | 3,529,908 A | 9/1970 | Smith |
| 3,273,447 A | 9/1966 | Frank | | 3,530,449 A | 9/1970 | Anderson |
| 3,283,352 A | 11/1966 | Hu | | 3,533,403 A | 10/1970 | Woodson |
| 3,290,919 A | 12/1966 | Malinak et al. | | 3,534,728 A | 10/1970 | Barrows |
| 3,292,493 A | 12/1966 | Franklin | | 3,534,872 A | 10/1970 | Roth et al. |
| 3,292,888 A | 12/1966 | Fischer | | 3,535,914 A | 10/1970 | Veith et al. |
| 3,294,988 A | 12/1966 | Packard | | 3,539,009 A | 11/1970 | Kudlaty |
| 3,299,603 A | 1/1967 | Shaw | | 3,543,744 A | 12/1970 | LePar |
| 3,299,882 A | 1/1967 | Masino | | 3,545,275 A | 12/1970 | Harrison et al. |
| 3,301,514 A | 1/1967 | Sugaya | | 3,550,583 A | 12/1970 | Chiku |
| 3,302,457 A | 2/1967 | Mayes | | 3,550,847 A | 12/1970 | Scott |
| 3,306,384 A | 2/1967 | Ross | | 3,563,094 A | 2/1971 | Rieschel |
| 3,313,314 A | 4/1967 | Burke et al. | | 3,563,245 A | 2/1971 | McLean et al. |
| 3,316,935 A | 5/1967 | Kaiser et al. | | 3,566,083 A | 2/1971 | McMillin |
| 3,320,750 A | 5/1967 | Haise et al. | | 3,566,875 A | 3/1971 | Stoehr |
| 3,321,035 A | 5/1967 | Tarpley | | 3,568,367 A | 3/1971 | Myers |
| 3,329,391 A * | 7/1967 | Deane ............................... 251/7 | | 3,568,636 A | 3/1971 | Lockwood |
| 3,332,788 A | 7/1967 | Barnby | | 3,576,554 A | 4/1971 | Temps, Jr. et al. |
| 3,334,510 A | 8/1967 | Hallesy | | 3,580,082 A | 5/1971 | Strack |
| 3,339,401 A | 9/1967 | Peters | | 3,581,402 A | 6/1971 | London et al. |
| 3,340,868 A | 9/1967 | Darling | | 3,583,387 A | 6/1971 | Garner et al. |
| 3,347,162 A | 10/1967 | Braznell | | 3,587,204 A | 6/1971 | George |
| 3,350,944 A | 11/1967 | De Michele | | 3,590,809 A | 7/1971 | London |
| 3,353,364 A | 11/1967 | Blanding et al. | | 3,590,818 A | 7/1971 | Lemole |
| 3,353,481 A | 11/1967 | Antonucci | | 3,590,992 A | 7/1971 | Soderstrom et al. |
| 3,356,334 A | 12/1967 | Scaramucci | | 3,592,183 A | 7/1971 | Watkins et al. |
| 3,356,510 A | 12/1967 | Barnby | | 3,594,519 A | 7/1971 | Schmidlin |
| 3,357,218 A | 12/1967 | Mitchell | | 3,602,885 A | 8/1971 | Grajeda |
| 3,357,461 A | 12/1967 | Friendship | | 3,610,016 A | 10/1971 | Bultman |
| 3,359,741 A | 12/1967 | Nelson | | 3,610,851 A | 10/1971 | Krupski |
| 3,361,300 A | 1/1968 | Kaplan | | 3,611,811 A | 10/1971 | Lissau |
| 3,364,929 A | 1/1968 | Ide et al. | | 3,614,926 A | 10/1971 | Brechtel |
| 3,365,684 A | 1/1968 | Stemke | | 3,614,955 A | 10/1971 | Mirowski et al. |
| 3,378,456 A | 4/1968 | Roberts | | 3,619,742 A | 11/1971 | Rud, Jr. |
| 3,380,445 A | 4/1968 | Frasier | | 3,623,371 A | 11/1971 | Jullien-Davin |
| 3,380,649 A | 4/1968 | Roberts | | 3,624,854 A | 12/1971 | Strong |
| 3,385,022 A | 5/1968 | Anderson | | 3,630,242 A | 12/1971 | Schieser et al. |
| 3,389,355 A | 6/1968 | Schroeder, Jr. | | 3,631,847 A | 1/1972 | Hobbs, II |
| 3,393,612 A | 7/1968 | Gorgens et al. | | 3,633,881 A | 1/1972 | Yurdin |
| 3,396,561 A | 8/1968 | Day | | 3,635,061 A | 1/1972 | Rydell et al. |
| 3,399,667 A | 9/1968 | Nishimoto et al. | | 3,635,074 A | 1/1972 | Moos et al. |
| 3,400,734 A | 9/1968 | Rosenberg | | 3,638,496 A | 2/1972 | King |
| 3,403,237 A | 9/1968 | Wysong | | 3,644,883 A | 2/1972 | Borman et al. |
| 3,409,924 A | 11/1968 | Slama | | 3,648,687 A | 3/1972 | Ramsey, III |
| 3,411,347 A | 11/1968 | Wirth et al. | | 3,651,289 A | 3/1972 | Nagashima et al. |
| 3,417,476 A | 12/1968 | Martens | | 3,651,405 A | 3/1972 | Whitney et al. |
| 3,420,325 A | 1/1969 | McAlister et al. | | 3,653,671 A | 4/1972 | Shipes |
| 3,422,324 A | 1/1969 | Webb | | 3,659,615 A | 5/1972 | Enger |
| 3,426,165 A | 2/1969 | Beaman | | 3,675,656 A * | 7/1972 | Hakim .......................... 606/158 |
| 3,438,391 A | 4/1969 | Yocum | | 3,677,444 A * | 7/1972 | Merrill .......................... 222/135 |
| 3,443,608 A | 5/1969 | Copping et al. | | 3,677,685 A | 7/1972 | Aoki et al. |
| 3,445,335 A | 5/1969 | Gluntz | | 3,686,958 A | 8/1972 | Porter et al. |
| 3,447,281 A | 6/1969 | Bufford et al. | | 3,688,568 A | 9/1972 | Karper et al. |
| 3,450,153 A | 6/1969 | Hildebrandt et al. | | 3,701,392 A | 10/1972 | Wirth et al. |
| 3,453,546 A | 7/1969 | Fryer | | 3,702,677 A | 11/1972 | Heffington |
| 3,453,848 A | 7/1969 | Williamson | | 3,703,099 A | 11/1972 | Rouse et al. |
| 3,456,134 A | 7/1969 | Ko | | 3,712,138 A | 1/1973 | Alinari et al. |
| 3,457,909 A | 7/1969 | Laird | | 3,713,124 A | 1/1973 | Durland et al. |
| 3,460,557 A | 8/1969 | Gallant | | 3,717,174 A * | 2/1973 | Dewall ..................... 137/565.15 |
| 3,463,338 A | 8/1969 | Schneider | | 3,719,524 A | 3/1973 | Ripley et al. |
| 3,469,818 A | 9/1969 | Cowan | | 3,721,412 A | 3/1973 | Kindorf |
| 3,470,725 A | 10/1969 | Brown et al. | | 3,723,247 A | 3/1973 | Leine et al. |
| 3,472,230 A | 10/1969 | Fogarty | | 3,724,000 A | 4/1973 | Eakman |
| 3,478,344 A | 11/1969 | Schwitzgebel et al. | | 3,727,463 A | 4/1973 | Intraub |
| 3,482,449 A | 12/1969 | Werner | | 3,727,616 A | 4/1973 | Lenzkes |
| 3,482,816 A | 12/1969 | Arnold | | 3,730,174 A | 5/1973 | Madison |
| 3,487,959 A | 1/1970 | Pearne et al. | | 3,730,560 A | 5/1973 | Abildgaard et al. |
| 3,491,842 A | 1/1970 | Delacour et al. | | 3,731,679 A | 5/1973 | Wilhelmson et al. |

| Patent No. | Date | Name |
|---|---|---|
| 3,731,681 A | 5/1973 | Blackshear et al. |
| 3,732,731 A | 5/1973 | Fussell, Jr. |
| 3,735,040 A | 5/1973 | Punt et al. |
| 3,736,930 A | 6/1973 | Georgi |
| 3,738,356 A | 6/1973 | Workman |
| 3,740,921 A | 6/1973 | Meyer et al. |
| 3,746,111 A | 7/1973 | Berthiaume et al. |
| 3,748,678 A | 7/1973 | Ballou |
| 3,749,098 A | 7/1973 | De Bennetot et al. |
| 3,749,422 A | 7/1973 | Abildgaard et al. |
| 3,749,423 A | 7/1973 | Abildgaard et al. |
| 3,750,194 A | 8/1973 | Summers |
| 3,757,770 A | 9/1973 | Brayshaw et al. |
| 3,759,095 A | 9/1973 | Short, Jr. et al. |
| 3,760,638 A | 9/1973 | Lawson et al. |
| 3,763,960 A | 10/1973 | John et al. |
| 3,765,142 A | 10/1973 | Lindquist et al. |
| 3,765,494 A | 10/1973 | Kielman, Jr. |
| 3,769,156 A | 10/1973 | Brecy et al. |
| 3,769,830 A | 11/1973 | Porter et al. |
| 3,774,243 A | 11/1973 | Ng et al. |
| 3,776,333 A | 12/1973 | Mathauser |
| 3,778,051 A | 12/1973 | Allen et al. |
| 3,780,578 A | 12/1973 | Sellman et al. |
| 3,781,902 A | 12/1973 | Shim et al. |
| 3,783,585 A | 1/1974 | Hoyland et al. |
| 3,789,667 A | 2/1974 | Porter et al. |
| 3,796,095 A | 3/1974 | Fussell, Jr. |
| 3,807,219 A | 4/1974 | Wallskog |
| 3,811,429 A | 5/1974 | Fletcher et al. |
| 3,815,722 A | 6/1974 | Sessoms |
| 3,818,765 A | 6/1974 | Eriksen et al. |
| 3,820,400 A | 6/1974 | Russo |
| 3,820,795 A | 6/1974 | Taylor |
| 3,823,610 A | 7/1974 | Fussell, Jr. |
| 3,825,065 A | 7/1974 | Lloyd et al. |
| 3,825,963 A | 7/1974 | Abildgaard et al. |
| 3,825,964 A | 7/1974 | Groswith, III et al. |
| 3,828,672 A | 8/1974 | Gazzola et al. |
| 3,828,766 A | 8/1974 | Krasnow |
| 3,831,588 A | 8/1974 | Rindner |
| 3,831,942 A | 8/1974 | Del Mar |
| 3,833,238 A | 9/1974 | Liard et al. |
| 3,834,167 A | 9/1974 | Tabor |
| 3,834,739 A | 9/1974 | Abildgaard et al. |
| 3,835,523 A | 9/1974 | Stansfield et al. |
| 3,839,708 A | 10/1974 | Bredesen et al. |
| 3,842,483 A | 10/1974 | Cramer |
| 3,842,668 A | 10/1974 | Lippke et al. |
| 3,845,664 A | 11/1974 | Perry, Jr. |
| 3,845,751 A | 11/1974 | Runstetler |
| 3,845,757 A | 11/1974 | Weyer |
| 3,847,434 A | 11/1974 | Weman et al. |
| 3,850,208 A | 11/1974 | Hamilton |
| 3,853,117 A | 12/1974 | Murr |
| 3,854,469 A | 12/1974 | Giori et al. |
| 3,855,902 A | 12/1974 | Kirst et al. |
| 3,857,399 A | 12/1974 | Zacouto et al. |
| 3,857,452 A | 12/1974 | Hartman |
| 3,857,745 A | 12/1974 | Grausch et al. |
| 3,858,581 A | 1/1975 | Kamen |
| 3,863,622 A | 2/1975 | Buuck |
| 3,863,933 A | 2/1975 | Tredway |
| 3,867,950 A | 2/1975 | Fischell |
| 3,868,008 A | 2/1975 | Brumbaugh |
| 3,868,679 A | 2/1975 | Arneson |
| 3,871,599 A | 3/1975 | Takada et al. |
| 3,872,285 A | 3/1975 | Shum et al. |
| 3,874,388 A | 4/1975 | King et al. |
| 3,876,980 A | 4/1975 | Haemmig et al. |
| 3,878,908 A | 4/1975 | Andersson et al. |
| 3,881,528 A | 5/1975 | Mackenzie |
| 3,893,111 A | 7/1975 | Cotter |
| 3,893,451 A | 7/1975 | Durand et al. |
| 3,895,681 A | 7/1975 | Griffin et al. |
| 3,899,862 A | 8/1975 | Muys et al. |
| 3,904,234 A | 9/1975 | Hill et al. |
| 3,908,334 A | 9/1975 | Rychiger et al. |
| 3,908,461 A | 9/1975 | Turpen |
| 3,908,721 A | 9/1975 | McGahey et al. |
| 3,910,087 A | 10/1975 | Jones |
| 3,912,168 A | 10/1975 | Mullins et al. |
| 3,912,304 A | 10/1975 | Abildgaard et al. |
| 3,918,286 A | 11/1975 | Whitehead |
| 3,918,291 A | 11/1975 | Pauly et al. |
| 3,920,965 A | 11/1975 | Sohrwardy et al. |
| 3,921,682 A | 11/1975 | McGahey et al. |
| 3,922,951 A | 12/1975 | Linsinger et al. |
| 3,923,060 A | 12/1975 | Ellinwood, Jr. |
| 3,924,635 A | 12/1975 | Hakim et al. |
| 3,928,980 A | 12/1975 | Ganzinotti et al. |
| 3,929,175 A | 12/1975 | Coone |
| 3,930,682 A | 1/1976 | Booth |
| 3,930,852 A | 1/1976 | Tanaka et al. |
| 3,936,028 A | 2/1976 | Norton et al. |
| 3,940,122 A | 2/1976 | Janzen et al. |
| 3,940,630 A | 2/1976 | Bergonz |
| 3,942,299 A | 3/1976 | Bory et al. |
| 3,942,382 A | 3/1976 | Hok et al. |
| 3,942,516 A | 3/1976 | Glynn et al. |
| 3,942,536 A | 3/1976 | Mirowski et al. |
| 3,943,915 A | 3/1976 | Severson |
| 3,945,704 A | 3/1976 | Kraus et al. |
| 3,946,613 A | 3/1976 | Silver |
| 3,946,615 A | 3/1976 | Hluchan |
| 3,946,724 A | 3/1976 | La Balme et al. |
| 3,948,141 A | 4/1976 | Shinjo et al. |
| 3,949,388 A | 4/1976 | Fuller |
| 3,953,289 A | 4/1976 | Costes et al. |
| 3,954,271 A | 5/1976 | Tredway, Sr. |
| 3,958,558 A | 5/1976 | Dunphy et al. |
| 3,961,425 A | 6/1976 | Swanson et al. |
| 3,961,646 A | 6/1976 | Schon et al. |
| 3,962,895 A | 6/1976 | Rydell et al. |
| 3,962,921 A | 6/1976 | Lips |
| 3,963,019 A | 6/1976 | Quandt |
| 3,964,485 A | 6/1976 | Neumeier |
| 3,964,770 A | 6/1976 | Abildgaard et al. |
| 3,967,737 A | 7/1976 | Peralta et al. |
| 3,968,473 A | 7/1976 | Patton et al. |
| 3,968,694 A | 7/1976 | Clark |
| 3,972,320 A | 8/1976 | Kalman |
| 3,973,753 A | 8/1976 | Wheeler |
| 3,973,858 A | 8/1976 | Poisson et al. |
| 3,974,655 A | 8/1976 | Halpern et al. |
| 3,974,865 A | 8/1976 | Fenton et al. |
| 3,977,391 A | 8/1976 | Fleischmann |
| 3,980,871 A | 9/1976 | Lindstrom et al. |
| 3,982,571 A | 9/1976 | Fenton et al. |
| 3,983,948 A | 10/1976 | Jeter |
| 3,985,133 A | 10/1976 | Jenkins et al. |
| 3,987,860 A | 10/1976 | Jabsen |
| 3,989,005 A | 11/1976 | Bowler, Jr. et al. |
| 3,991,749 A | 11/1976 | Zent |
| 3,992,948 A | 11/1976 | D'Antonio et al. |
| 3,993,149 A | 11/1976 | Harvey |
| 3,996,927 A | 12/1976 | Frank |
| 3,996,962 A | 12/1976 | Sutherland |
| 4,003,141 A | 1/1977 | Le Roy |
| 4,005,282 A | 1/1977 | Jennings |
| 4,005,593 A | 2/1977 | Goldberg |
| 4,006,735 A | 2/1977 | Hittman et al. |
| 4,009,375 A | 2/1977 | White et al. |
| 4,009,591 A | 3/1977 | Hester |
| 4,010,449 A | 3/1977 | Faggin et al. |
| 4,014,319 A | 3/1977 | Favre et al. |
| 4,014,321 A | 3/1977 | March |
| 4,016,764 A | 4/1977 | Rice |
| 4,017,329 A | 4/1977 | Larson |
| 4,018,134 A | 4/1977 | Linsinger et al. |
| 4,022,190 A | 5/1977 | Meyer |
| 4,024,864 A | 5/1977 | Davies et al. |
| 4,025,912 A | 5/1977 | Rice |
| 4,026,276 A | 5/1977 | Chubbuck |
| 4,027,661 A | 6/1977 | Lyon et al. |
| 4,031,899 A | 6/1977 | Renirie et al. |
| 4,036,775 A | 7/1977 | Trautvetter et al. |
| 4,039,069 A | 8/1977 | Kwan et al. |

| | | | | | | |
|---|---|---|---|---|---|---|
| 4,041,954 A | 8/1977 | Ohara et al. | | 4,170,280 A | 10/1979 | Schwarz |
| 4,042,504 A | 8/1977 | Drori et al. | | 4,171,218 A | 10/1979 | Hoshino et al. |
| 4,045,345 A | 8/1977 | Drori et al. | | 4,183,124 A | 1/1980 | Hoffman |
| 4,047,851 A | 9/1977 | Bender | | 4,183,247 A | 1/1980 | Allen et al. |
| 4,048,494 A | 9/1977 | Liesting et al. | | 4,185,641 A | 1/1980 | Minior et al. |
| 4,048,879 A | 9/1977 | Cox | | 4,186,287 A | 1/1980 | Scott |
| 4,049,004 A | 9/1977 | Walters | | 4,186,749 A | 2/1980 | Fryer |
| 4,051,338 A | 9/1977 | Harris, III | | 4,186,751 A | 2/1980 | Fleischmann |
| 4,052,991 A | 10/1977 | Zacouto et al. | | 4,190,057 A | 2/1980 | Hill et al. |
| 4,055,074 A | 10/1977 | Thimons et al. | | 4,191,004 A | 3/1980 | Gmuer et al. |
| 4,055,175 A | 10/1977 | Clemens et al. | | 4,191,187 A | 3/1980 | Wright et al. |
| 4,056,854 A | 11/1977 | Boretos et al. | | 4,192,192 A | 3/1980 | Schnell |
| 4,058,007 A | 11/1977 | Exner et al. | | 4,193,397 A | 3/1980 | Tucker et al. |
| 4,062,351 A | 12/1977 | Hastwell et al. | | 4,204,547 A | 5/1980 | Allocca |
| 4,062,354 A | 12/1977 | Taylor et al. | | 4,206,755 A | 6/1980 | Klein et al. |
| 4,062,360 A | 12/1977 | Bentley | | 4,206,761 A | 6/1980 | Cosman |
| 4,063,439 A | 12/1977 | Besson et al. | | 4,206,762 A | 6/1980 | Cosman |
| 4,064,882 A | 12/1977 | Johnson et al. | | 4,207,903 A | 6/1980 | O'Neill |
| 4,070,239 A | 1/1978 | Bevilacqua | | 4,212,074 A | 7/1980 | Kuno et al. |
| 4,072,047 A | 2/1978 | Reismuller et al. | | 4,217,221 A | 8/1980 | Masso |
| 4,073,292 A | 2/1978 | Edelman | | 4,217,588 A | 8/1980 | Freeny, Jr. |
| 4,075,099 A | 2/1978 | Pelton et al. | | 4,220,189 A | 9/1980 | Marquez |
| 4,075,602 A | 2/1978 | Clothier | | 4,221,219 A | 9/1980 | Tucker |
| 4,077,072 A | 3/1978 | Dezura et al. | | 4,221,523 A | 9/1980 | Eberle |
| 4,077,394 A | 3/1978 | McCurdy | | 4,222,377 A | 9/1980 | Burton |
| 4,077,405 A | 3/1978 | Haerten et al. | | 4,223,837 A | 9/1980 | Gubbiotti et al. |
| 4,077,882 A | 3/1978 | Gangemi | | 4,226,124 A | 10/1980 | Kersten et al. |
| 4,078,620 A | 3/1978 | Westlake et al. | | 4,226,229 A | 10/1980 | Eckhart et al. |
| 4,080,653 A | 3/1978 | Barnes, Jr. et al. | | 4,227,533 A | 10/1980 | Godfrey |
| 4,084,752 A | 4/1978 | Hagiwara et al. | | 4,231,376 A | 11/1980 | Lyon et al. |
| 4,086,488 A | 4/1978 | Hill | | 4,232,682 A | 11/1980 | Veth |
| 4,087,568 A | 5/1978 | Fay et al. | | 4,237,900 A | 12/1980 | Schulman et al. |
| 4,088,417 A | 5/1978 | Kosmowski | | 4,241,247 A | 12/1980 | Byrne et al. |
| 4,089,329 A | 5/1978 | Couvillon, Jr. et al. | | 4,241,870 A | 12/1980 | Marcus |
| 4,090,802 A | 5/1978 | Bilz et al. | | 4,245,593 A | 1/1981 | Stein |
| 4,092,719 A | 5/1978 | Salmon et al. | | 4,246,877 A | 1/1981 | Kennedy |
| 4,092,925 A | 6/1978 | Fromson | | 4,247,850 A | 1/1981 | Marcus |
| 4,096,866 A | 6/1978 | Fischell | | 4,248,238 A | 2/1981 | Joseph et al. |
| 4,098,293 A | 7/1978 | Kramer et al. | | 4,248,241 A | 2/1981 | Tacchi |
| 4,103,496 A | 8/1978 | Colamussi et al. | | 4,256,094 A | 3/1981 | Kapp et al. |
| 4,106,370 A | 8/1978 | Kraus et al. | | 4,256,118 A | 3/1981 | Nagel et al. |
| 4,107,689 A | 8/1978 | Jellinek | | 4,256,130 A * | 3/1981 | Smith et al. .................. 137/1 |
| 4,107,995 A | 8/1978 | Ligman et al. | | 4,262,343 A | 4/1981 | Claycomb |
| 4,108,148 A | 8/1978 | Cannon, III | | 4,262,632 A | 4/1981 | Hanton et al. |
| 4,108,575 A | 8/1978 | Schal et al. | | 4,265,241 A | 5/1981 | Portner et al. |
| 4,109,148 A | 8/1978 | Jaulmes et al. | | 4,265,252 A | 5/1981 | Chubbuck et al. |
| 4,109,518 A | 8/1978 | Dooley et al. | | 4,271,018 A | 6/1981 | Drori et al. |
| 4,109,644 A | 8/1978 | Kojima | | 4,273,070 A | 6/1981 | Hoefelmayr et al. |
| 4,111,056 A | 9/1978 | Mastromatteo | | 4,274,444 A | 6/1981 | Ruyak |
| 4,111,629 A | 9/1978 | Nussbaumer et al. | | 4,275,600 A | 6/1981 | Turner et al. |
| 4,114,424 A | 9/1978 | Johnson | | 4,275,913 A | 6/1981 | Marcus |
| 4,114,606 A | 9/1978 | Seylar | | 4,278,540 A | 7/1981 | Drori et al. |
| 4,120,097 A | 10/1978 | Jeter | | 4,280,036 A | 7/1981 | Fukatsu et al. |
| 4,120,134 A | 10/1978 | Scholle | | 4,280,775 A | 7/1981 | Wood |
| 4,121,635 A | 10/1978 | Hansel | | 4,281,666 A | 8/1981 | Cosman |
| 4,123,310 A | 10/1978 | Varon et al. | | 4,281,667 A | 8/1981 | Cosman |
| 4,124,023 A | 11/1978 | Fleischmann et al. | | 4,284,073 A | 8/1981 | Krause et al. |
| 4,127,110 A | 11/1978 | Bullara | | 4,285,770 A | 8/1981 | Chi et al. |
| 4,130,169 A | 12/1978 | Denison | | 4,291,699 A | 9/1981 | Geddes et al. |
| 4,131,596 A | 12/1978 | Allen | | 4,295,963 A | 10/1981 | Drori et al. |
| 4,133,355 A | 1/1979 | Mayer | | 4,297,927 A | 11/1981 | Kuroda et al. |
| 4,133,367 A | 1/1979 | Abell | | 4,303,075 A | 12/1981 | Heilman et al. |
| 4,140,131 A | 2/1979 | Dutcher et al. | | 4,305,402 A | 12/1981 | Katims |
| 4,141,348 A | 2/1979 | Hittman | | 4,312,374 A | 1/1982 | Drori et al. |
| 4,141,349 A | 2/1979 | Ory et al. | | 4,314,480 A | 2/1982 | Becker |
| 4,143,661 A | 3/1979 | LaForge et al. | | 4,316,693 A | 2/1982 | Baxter et al. |
| 4,146,029 A | 3/1979 | Ellinwood, Jr. | | 4,325,387 A | 4/1982 | Helfer |
| 4,147,161 A | 4/1979 | Ikebe et al. | | 4,327,804 A | 5/1982 | Reed |
| 4,148,096 A | 4/1979 | Haas et al. | | 4,328,654 A | 5/1982 | Van Ginkel et al. |
| 4,149,423 A | 4/1979 | Frosch et al. | | 4,332,254 A | 6/1982 | Lundquist |
| 4,151,823 A | 5/1979 | Grosse et al. | | 4,339,831 A | 7/1982 | Johnson |
| 4,153,085 A | 5/1979 | Adams | | 4,342,218 A | 8/1982 | Fox |
| 4,156,422 A | 5/1979 | Hildebrandt et al. | | 4,342,308 A | 8/1982 | Trick |
| 4,160,448 A | 7/1979 | Jackson | | 4,346,604 A | 8/1982 | Snook et al. |
| 4,160,971 A | 7/1979 | Jones et al. | | 4,347,851 A | 9/1982 | Jundanian |
| 4,166,469 A | 9/1979 | Littleford | | 4,350,647 A | 9/1982 | de la Cruz |
| 4,167,304 A | 9/1979 | Gelbke | | 4,350,970 A | 9/1982 | von Tomkewitsch et al. |
| 4,167,952 A | 9/1979 | Reinicke | | 4,351,037 A | 9/1982 | Scherbatskoy |
| 4,168,567 A | 9/1979 | Leguy et al. | | 4,351,116 A | 9/1982 | Scott, Jr. |

| | | |
|---|---|---|
| 4,356,486 A | 10/1982 | Mount |
| 4,360,010 A | 11/1982 | Finney |
| 4,360,277 A | 11/1982 | Daniel et al. |
| 4,361,153 A | 11/1982 | Slocum et al. |
| 4,363,236 A | 12/1982 | Meyers |
| 4,364,276 A | 12/1982 | Shimazoe et al. |
| 4,365,425 A | 12/1982 | Gotchel |
| 4,368,937 A | 1/1983 | Palombo et al. |
| 4,369,013 A | 1/1983 | Abildgaard et al. |
| 4,373,527 A | 2/1983 | Fischell |
| 4,376,523 A | 3/1983 | Goyen et al. |
| 4,378,809 A | 4/1983 | Cosman |
| 4,380,427 A | 4/1983 | Hehl et al. |
| 4,385,636 A | 5/1983 | Cosman |
| 4,386,422 A | 5/1983 | Mumby et al. |
| 4,387,907 A | 6/1983 | Hiestand et al. |
| 4,392,368 A | 7/1983 | Folkesson et al. |
| 4,393,899 A | 7/1983 | Tsuji et al. |
| 4,393,951 A | 7/1983 | Horst-Rudolf et al. |
| 4,395,232 A | 7/1983 | Koch |
| 4,395,258 A | 7/1983 | Wang et al. |
| 4,395,916 A | 8/1983 | Martin |
| 4,398,983 A | 8/1983 | Suzuki et al. |
| 4,399,705 A | 8/1983 | Weiger et al. |
| 4,399,707 A | 8/1983 | Wamstad |
| 4,399,809 A | 8/1983 | Baro et al. |
| 4,399,821 A | 8/1983 | Bowers |
| 4,403,984 A | 9/1983 | Ash et al. |
| 4,404,968 A | 9/1983 | Evans, Sr. |
| 4,404,974 A | 9/1983 | Titus |
| 4,405,318 A | 9/1983 | Whitney et al. |
| 4,407,125 A | 10/1983 | Parsons et al. |
| 4,407,271 A | 10/1983 | Schiff |
| 4,407,296 A | 10/1983 | Anderson |
| 4,407,326 A | 10/1983 | Wilhelm |
| 4,408,597 A | 10/1983 | Tenney, Jr. |
| 4,408,615 A | 10/1983 | Grossman |
| 4,410,164 A * | 10/1983 | Kamen ............ 251/9 |
| 4,415,071 A | 11/1983 | Butler et al. |
| 4,416,282 A | 11/1983 | Saulson et al. |
| 4,418,899 A | 12/1983 | Zimmermann et al. |
| 4,419,393 A | 12/1983 | Hanson et al. |
| 4,421,505 A | 12/1983 | Schwartz |
| 4,424,720 A | 1/1984 | Bucchianeri |
| 4,428,228 A | 1/1984 | Banzhaf et al. |
| 4,428,365 A | 1/1984 | Hakky et al. |
| 4,430,899 A | 2/1984 | Wessel et al. |
| 4,431,009 A | 2/1984 | Marino, Jr. et al. |
| 4,431,365 A | 2/1984 | Sturtz, Jr. |
| 4,432,363 A | 2/1984 | Kakegawa et al. |
| 4,435,173 A | 3/1984 | Siposs et al. |
| 4,439,186 A | 3/1984 | Kuhl et al. |
| 4,441,491 A | 4/1984 | Evans, Sr. |
| 4,441,501 A | 4/1984 | Parent |
| 4,444,194 A | 4/1984 | Burcham |
| 4,444,498 A | 4/1984 | Heinemann |
| 4,445,385 A | 5/1984 | Endo |
| 4,446,711 A | 5/1984 | Valente |
| 4,447,224 A | 5/1984 | DeCant, Jr. et al. |
| 4,449,493 A | 5/1984 | Kopec et al. |
| 4,450,811 A | 5/1984 | Ichikawa et al. |
| 4,451,033 A | 5/1984 | Nestegard |
| 4,453,537 A | 6/1984 | Spitzer |
| 4,453,578 A | 6/1984 | Wilder |
| 4,460,835 A | 7/1984 | Masuoka et al. |
| 4,464,170 A | 8/1984 | Clemens et al. |
| 4,465,015 A | 8/1984 | Osta et al. |
| 4,465,474 A | 8/1984 | Mardorf et al. |
| 4,466,290 A | 8/1984 | Frick |
| 4,468,172 A | 8/1984 | Dixon et al. |
| 4,468,762 A | 8/1984 | Jurgens et al. |
| 4,469,365 A | 9/1984 | Marcus et al. |
| 4,471,182 A | 9/1984 | Wielgos et al. |
| 4,471,786 A | 9/1984 | Inagaki et al. |
| 4,473,067 A | 9/1984 | Schiff |
| 4,473,078 A | 9/1984 | Angel |
| 4,476,721 A | 10/1984 | Hochreuther et al. |
| 4,478,213 A | 10/1984 | Redding |
| 4,478,538 A | 10/1984 | Kakino et al. |
| 4,483,196 A | 11/1984 | Kurtz et al. |
| 4,484,135 A | 11/1984 | Ishihara et al. |
| 4,485,813 A | 12/1984 | Anderson et al. |
| 4,489,916 A | 12/1984 | Stevens |
| 4,492,632 A | 1/1985 | Mattson |
| 4,493,706 A * | 1/1985 | Borsanyi et al. ............ 604/153 |
| 4,494,411 A | 1/1985 | Koschke et al. |
| 4,494,950 A | 1/1985 | Fischell |
| 4,497,176 A | 2/1985 | Rubin et al. |
| 4,497,201 A | 2/1985 | Allen et al. |
| 4,499,394 A | 2/1985 | Koal |
| 4,499,691 A | 2/1985 | Karazim et al. |
| 4,499,750 A | 2/1985 | Gerber et al. |
| 4,503,678 A | 3/1985 | Wimbush et al. |
| 4,511,974 A | 4/1985 | Nakane et al. |
| 4,513,295 A | 4/1985 | Jones et al. |
| 4,515,004 A | 5/1985 | Jaenson |
| 4,515,750 A | 5/1985 | Pardini et al. |
| 4,516,866 A | 5/1985 | Yamauchi et al. |
| 4,518,637 A | 5/1985 | Takeda et al. |
| 4,519,401 A | 5/1985 | Ko et al. |
| 4,520,443 A | 5/1985 | Yuki et al. |
| 4,522,213 A | 6/1985 | Wallroth et al. |
| 4,527,568 A | 7/1985 | Rickards et al. |
| 4,529,401 A | 7/1985 | Leslie et al. |
| 4,531,526 A | 7/1985 | Genest |
| 4,531,936 A | 7/1985 | Gordon |
| 4,536,000 A | 8/1985 | Rohm et al. |
| 4,537,005 A | 8/1985 | Hoyland et al. |
| 4,537,129 A | 8/1985 | Heinemann et al. |
| 4,538,616 A | 9/1985 | Rogoff |
| 4,540,404 A | 9/1985 | Wolvek |
| 4,542,461 A | 9/1985 | Eldridge et al. |
| 4,544,369 A | 10/1985 | Skakoon et al. |
| 4,545,185 A | 10/1985 | Chikatani et al. |
| 4,546,524 A | 10/1985 | Kreft |
| 4,548,209 A | 10/1985 | Wielders et al. |
| 4,552,150 A | 11/1985 | Zacouto et al. |
| 4,553,226 A | 11/1985 | Scherbatskoy |
| 4,556,063 A | 12/1985 | Thompson et al. |
| 4,557,269 A | 12/1985 | Reynolds et al. |
| 4,557,332 A | 12/1985 | Denison et al. |
| 4,559,815 A | 12/1985 | Needham et al. |
| 4,560,979 A | 12/1985 | Rosskopf et al. |
| 4,561,442 A | 12/1985 | Vollmann et al. |
| 4,562,751 A | 1/1986 | Nason et al. |
| 4,563,175 A | 1/1986 | LaFond |
| 4,565,116 A | 1/1986 | Hehl et al. |
| 4,566,456 A | 1/1986 | Koning et al. |
| 4,569,623 A | 2/1986 | Goldmann |
| 4,570,351 A | 2/1986 | Szanto et al. |
| 4,571,161 A | 2/1986 | Leblanc et al. |
| 4,571,995 A | 2/1986 | Timme |
| 4,573,835 A | 3/1986 | Eckardt et al. |
| 4,574,792 A | 3/1986 | Trick |
| 4,576,181 A | 3/1986 | Wallace et al. |
| 4,576,183 A | 3/1986 | Plicchi et al. |
| 4,577,512 A | 3/1986 | Lowenheck et al. |
| 4,581,018 A | 4/1986 | Jassawalla et al. |
| 4,581,915 A | 4/1986 | Haulsee et al. |
| 4,587,840 A | 5/1986 | Dobler et al. |
| 4,589,626 A * | 5/1986 | Kurtz et al. ............ 251/10 |
| 4,589,805 A | 5/1986 | Duffner et al. |
| 4,592,339 A | 6/1986 | Kuzmak et al. |
| 4,592,340 A | 6/1986 | Boyles |
| 4,593,703 A | 6/1986 | Cosman |
| 4,595,228 A | 6/1986 | Chu |
| 4,596,563 A | 6/1986 | Pande |
| 4,599,943 A | 7/1986 | Kobler et al. |
| 4,600,855 A | 7/1986 | Strachan et al. |
| 4,602,541 A | 7/1986 | Benzinger et al. |
| 4,604,089 A | 8/1986 | Santangelo et al. |
| 4,605,354 A | 8/1986 | Daly |
| 4,606,419 A | 8/1986 | Perini |
| 4,606,478 A | 8/1986 | Hack et al. |
| 4,610,256 A | 9/1986 | Wallace |
| 4,614,137 A | 9/1986 | Jones |
| 4,617,016 A | 10/1986 | Blomberg et al. |
| 4,618,861 A | 10/1986 | Gettens et al. |

| | | | | | | |
|---|---|---|---|---|---|---|
| 4,620,807 A | 11/1986 | Polit | | 4,777,953 A | 10/1988 | Ash et al. |
| 4,621,331 A | 11/1986 | Iwata et al. | | 4,779,626 A | 10/1988 | Peel et al. |
| 4,622,871 A | 11/1986 | Van Sickle et al. | | 4,781,192 A | 11/1988 | Demer |
| 4,626,462 A | 12/1986 | Kober et al. | | 4,782,826 A | 11/1988 | Fogarty |
| 4,633,304 A | 12/1986 | Nagasaki et al. | | 4,783,106 A | 11/1988 | Nutter |
| 4,633,878 A | 1/1987 | Bombardieri et al. | | 4,788,847 A | 12/1988 | Sterghos |
| 4,635,182 A | 1/1987 | Hintz | | 4,791,318 A | 12/1988 | Lewis et al. |
| 4,637,736 A | 1/1987 | Andeen et al. | | 4,794,803 A | 1/1989 | Osterhout et al. |
| 4,638,665 A | 1/1987 | Benson et al. | | 4,796,641 A | 1/1989 | Mills et al. |
| 4,644,246 A | 2/1987 | Knapen et al. | | 4,798,211 A | 1/1989 | Goor et al. |
| 4,646,553 A | 3/1987 | Tufte et al. | | 4,798,227 A | 1/1989 | Goodwin |
| 4,648,363 A | 3/1987 | Kronich | | 4,799,491 A | 1/1989 | Eckerle |
| 4,648,406 A | 3/1987 | Miller | | 4,799,625 A | 1/1989 | Weaver, Jr. et al. |
| 4,658,358 A | 4/1987 | Leach et al. | | 4,800,879 A * | 1/1989 | Golyakhovsky et al. ...... 606/158 |
| 4,658,760 A | 4/1987 | Zebuhr | | 4,802,488 A | 2/1989 | Eckerle |
| 4,660,568 A | 4/1987 | Cosman | | 4,803,987 A | 2/1989 | Calfee et al. |
| 4,665,511 A | 5/1987 | Rodney et al. | | 4,804,368 A | 2/1989 | Skakoon et al. |
| 4,665,896 A | 5/1987 | LaForge et al. | | 4,807,321 A | 2/1989 | Grasselli et al. |
| 4,669,484 A | 6/1987 | Masters | | 4,808,167 A | 2/1989 | Mann et al. |
| 4,672,974 A | 6/1987 | Lee | | 4,812,823 A | 3/1989 | Dickerson |
| 4,674,457 A | 6/1987 | Berger et al. | | 4,813,938 A * | 3/1989 | Raulerson ...................... 604/158 |
| 4,674,546 A | 6/1987 | Fournier et al. | | 4,819,656 A | 4/1989 | Spector |
| 4,678,408 A | 7/1987 | Nason et al. | | 4,820,265 A | 4/1989 | DeSatnick et al. |
| 4,681,559 A | 7/1987 | Hooven | | 4,820,953 A | 4/1989 | Saubolle et al. |
| 4,683,850 A | 8/1987 | Bauder et al. | | 4,821,167 A | 4/1989 | Wiebe |
| 4,685,463 A | 8/1987 | Williams | | 4,821,723 A | 4/1989 | Baker, Jr. et al. |
| 4,685,469 A | 8/1987 | Keller et al. | | 4,823,779 A | 4/1989 | Daly et al. |
| 4,685,903 A | 8/1987 | Cable et al. | | 4,830,006 A | 5/1989 | Haluska et al. |
| 4,686,987 A | 8/1987 | Salo et al. | | 4,832,034 A | 5/1989 | Pizziconi et al. |
| 4,687,468 A * | 8/1987 | Gianturco ...................... 604/153 | | 4,833,384 A | 5/1989 | Munro et al. |
| 4,687,530 A | 8/1987 | Berscheid et al. | | 4,834,731 A | 5/1989 | Nowak et al. |
| 4,689,979 A | 9/1987 | Otsuka et al. | | 4,838,857 A | 6/1989 | Strowe et al. |
| 4,691,694 A | 9/1987 | Boyd et al. | | 4,840,068 A | 6/1989 | Mayhew, Jr. |
| 4,691,710 A | 9/1987 | Dickens et al. | | 4,840,350 A | 6/1989 | Cook et al. |
| 4,693,253 A | 9/1987 | Adams | | 4,844,002 A | 7/1989 | Yasui et al. |
| 4,695,237 A | 9/1987 | Inaba et al. | | 4,846,153 A | 7/1989 | Berci |
| 4,696,189 A | 9/1987 | Hochreuther et al. | | 4,846,191 A | 7/1989 | Brockway et al. |
| 4,697,574 A | 10/1987 | Karcher et al. | | 4,846,664 A | 7/1989 | Hehl et al. |
| 4,698,038 A | 10/1987 | Key et al. | | 4,854,328 A | 8/1989 | Pollack |
| 4,700,497 A | 10/1987 | Sato et al. | | 4,863,470 A | 9/1989 | Carter |
| 4,700,610 A | 10/1987 | Bauer et al. | | 4,865,587 A | 9/1989 | Walling |
| 4,701,143 A | 10/1987 | Key et al. | | 4,867,160 A | 9/1989 | Schaldach et al. |
| 4,703,756 A | 11/1987 | Gough et al. | | 4,867,498 A | 9/1989 | Delphia et al. |
| 4,705,507 A | 11/1987 | Boyles | | 4,867,618 A | 9/1989 | Brohammer |
| 4,706,948 A | 11/1987 | Kroecher et al. | | 4,869,252 A | 9/1989 | Gilli |
| 4,712,562 A | 12/1987 | Ohayon et al. | | 4,870,258 A | 9/1989 | Mochizuki et al. |
| 4,718,425 A | 1/1988 | Tanaka et al. | | 4,871,351 A | 10/1989 | Feingold et al. |
| 4,722,348 A | 2/1988 | Ligtenberg et al. | | 4,872,483 A | 10/1989 | Shah |
| 4,724,806 A | 2/1988 | Hartwig et al. | | 4,872,869 A | 10/1989 | Johns |
| 4,724,830 A | 2/1988 | Fischell | | 4,873,677 A | 10/1989 | Sakamoto et al. |
| 4,725,826 A | 2/1988 | Hunter | | 4,875,483 A | 10/1989 | Vollmann et al. |
| 4,728,479 A | 3/1988 | Merkovsky | | 4,880,004 A | 11/1989 | Baker, Jr. et al. |
| 4,729,384 A * | 3/1988 | Bazenet ........................ 600/504 | | 4,882,678 A | 11/1989 | Hollis et al. |
| 4,729,517 A | 3/1988 | Krokor et al. | | 4,886,392 A | 12/1989 | Iio et al. |
| 4,730,188 A | 3/1988 | Milheiser | | 4,895,151 A | 1/1990 | Grevis et al. |
| 4,730,420 A | 3/1988 | Stratmann et al. | | 4,896,594 A | 1/1990 | Baur et al. |
| 4,730,619 A | 3/1988 | Koning et al. | | 4,898,158 A | 2/1990 | Daly et al. |
| 4,731,058 A | 3/1988 | Doan | | 4,898,578 A | 2/1990 | Rubalcaba, Jr. |
| 4,735,205 A | 4/1988 | Chachques et al. | | 4,899,751 A | 2/1990 | Cohen |
| 4,738,267 A | 4/1988 | Lazorthes et al. | | 4,899,752 A | 2/1990 | Cohen |
| 4,738,268 A | 4/1988 | Kipnis | | 4,902,277 A | 2/1990 | Mathies et al. |
| 4,741,345 A | 5/1988 | Matthews et al. | | 4,903,701 A | 2/1990 | Moore et al. |
| 4,741,732 A | 5/1988 | Crankshaw et al. | | 4,909,678 A | 3/1990 | Kakimoto et al. |
| 4,743,129 A | 5/1988 | Keryhuel et al. | | 4,913,147 A | 4/1990 | Fahlstrom et al. |
| 4,745,541 A | 5/1988 | Vaniglia et al. | | 4,919,143 A | 4/1990 | Ayers |
| 4,746,830 A | 5/1988 | Holland | | 4,924,872 A | 5/1990 | Frank |
| 4,750,495 A | 6/1988 | Moore et al. | | 4,926,903 A | 5/1990 | Kawai et al. |
| 4,752,115 A | 6/1988 | Murray, Jr. et al. | | 4,932,406 A | 6/1990 | Berkovits |
| 4,752,658 A | 6/1988 | Mack | | 4,934,369 A | 6/1990 | Maxwell |
| 4,757,463 A | 7/1988 | Ballou et al. | | 4,936,304 A | 6/1990 | Kresh et al. |
| 4,759,386 A | 7/1988 | Grouw, III | | 4,940,037 A | 7/1990 | Eckert et al. |
| 4,763,649 A | 8/1988 | Merrick | | 4,941,718 A | 7/1990 | Alexander, III et al. |
| 4,765,001 A | 8/1988 | Smith | | 4,942,004 A | 7/1990 | Catanzaro |
| 4,767,406 A | 8/1988 | Wadham et al. | | 4,944,050 A | 7/1990 | Shames et al. |
| 4,769,001 A | 9/1988 | Prince | | 4,944,298 A | 7/1990 | Sholder |
| 4,772,896 A | 9/1988 | Nakatsu et al. | | 4,944,307 A | 7/1990 | Hon et al. |
| 4,773,401 A | 9/1988 | Citak et al. | | 4,945,761 A | 8/1990 | Lessi et al. |
| 4,774,950 A | 10/1988 | Cohen | | 4,949,724 A | 8/1990 | Mahutte et al. |
| 4,774,955 A | 10/1988 | Jones | | 4,952,205 A | 8/1990 | Mauerer et al. |

| Patent | Type | Date | Inventor |
|---|---|---|---|
| 4,952,928 A | | 8/1990 | Carroll et al. |
| 4,953,563 A | | 9/1990 | Kaiser et al. |
| 4,954,677 A | | 9/1990 | Alberter et al. |
| 4,958,630 A | | 9/1990 | Rosenbluth et al. |
| 4,958,645 A | | 9/1990 | Cadell et al. |
| 4,960,424 A | | 10/1990 | Grooters |
| 4,960,966 A | | 10/1990 | Evans et al. |
| 4,967,585 A | | 11/1990 | Grimaldo |
| 4,967,761 A | | 11/1990 | Nathanielsz |
| 4,970,823 A | | 11/1990 | Chen et al. |
| 4,971,251 A | | 11/1990 | Dobrick et al. |
| 4,977,896 A | | 12/1990 | Robinson et al. |
| 4,978,335 A | | 12/1990 | Arthur, III |
| 4,978,338 A | | 12/1990 | Melsky et al. |
| 4,979,730 A | | 12/1990 | Holbrook et al. |
| 4,980,671 A | | 12/1990 | McCurdy |
| 4,981,141 A | | 1/1991 | Segalowitz |
| 4,981,173 A | | 1/1991 | Perkins et al. |
| 4,981,426 A | | 1/1991 | Aoki et al. |
| 4,987,897 A | | 1/1991 | Funke et al. |
| 4,988,337 A | | 1/1991 | Ito et al. |
| 4,992,794 A | | 2/1991 | Brouwers et al. |
| 4,997,556 A | | 3/1991 | Yano et al. |
| 5,001,528 A | | 3/1991 | Bahraman |
| 5,003,807 A | | 4/1991 | Terrell et al. |
| 5,003,975 A | | 4/1991 | Hafelfinger et al. |
| 5,003,976 A | | 4/1991 | Alt et al. |
| 5,004,472 A | | 4/1991 | Wallace |
| 5,004,873 A | | 4/1991 | Schnut |
| 5,005,574 A | | 4/1991 | Fearnot et al. |
| 5,005,586 A | | 4/1991 | Lahr |
| 5,006,844 A | | 4/1991 | Ohta et al. |
| 5,007,401 A | | 4/1991 | Grohn et al. |
| 5,007,430 A | | 4/1991 | Dardik |
| 5,007,919 A | | 4/1991 | Silva et al. |
| 5,009,662 A | | 4/1991 | Wallace et al. |
| 5,010,893 A | | 4/1991 | Sholder |
| 5,012,286 A | | 4/1991 | Kawano et al. |
| 5,012,810 A | | 5/1991 | Strand et al. |
| 5,013,292 A | | 5/1991 | Lemay et al. |
| 5,014,040 A | | 5/1991 | Weaver et al. |
| 5,019,032 A | | 5/1991 | Robertson |
| 5,019,041 A | | 5/1991 | Robinson et al. |
| 5,020,845 A | | 6/1991 | Falcoff et al. |
| 5,021,046 A | | 6/1991 | Wallace |
| 5,022,395 A | | 6/1991 | Russie |
| 5,024,965 A | | 6/1991 | Chang et al. |
| 5,026,180 A | | 6/1991 | Tajima et al. |
| 5,026,360 A | | 6/1991 | Johnsen et al. |
| 5,028,918 A | | 7/1991 | Giles et al. |
| 5,032,822 A | | 7/1991 | Sweet |
| 5,036,869 A | | 8/1991 | Inahara et al. |
| 5,038,800 A | | 8/1991 | Oba et al. |
| 5,041,086 A | | 8/1991 | Koenig et al. |
| 5,041,826 A | | 8/1991 | Milheiser |
| 5,042,503 A | | 8/1991 | Torok et al. |
| 5,044,770 A | | 9/1991 | Haghkar |
| 5,046,661 A | | 9/1991 | Kimura et al. |
| 5,048,060 A | | 9/1991 | Arai et al. |
| 5,050,922 A | | 9/1991 | Falcoff |
| 5,052,910 A | | 10/1991 | Hehl et al. |
| 5,053,008 A | | 10/1991 | Bajaj |
| 5,057,078 A | | 10/1991 | Foote et al. |
| 5,058,583 A | | 10/1991 | Geddes et al. |
| 5,061,239 A | | 10/1991 | Shiels |
| 5,062,052 A | | 10/1991 | Sparer et al. |
| 5,062,053 A | | 10/1991 | Shirai et al. |
| 5,062,559 A | | 11/1991 | Falcoff |
| 5,064,974 A | | 11/1991 | Vigneau et al. |
| 5,067,960 A | | 11/1991 | Grandjean et al. |
| 5,068,779 A | | 11/1991 | Sullivan et al. |
| 5,069,680 A | | 12/1991 | Grandjean et al. |
| 5,077,102 A | | 12/1991 | Chong |
| 5,077,870 A | | 1/1992 | Melbye et al. |
| 5,078,139 A | | 1/1992 | Strand et al. |
| 5,082,006 A | | 1/1992 | Jonasson et al. |
| 5,083,563 A | | 1/1992 | Collins et al. |
| 5,084,699 A | | 1/1992 | DeMichele |
| 5,085,224 A | | 2/1992 | Galen et al. |
| 5,085,258 A | | 2/1992 | Fink, Jr. et al. |
| 5,089,673 A | | 2/1992 | Strzodka et al. |
| 5,089,979 A | | 2/1992 | McEachern et al. |
| 5,092,856 A * | | 3/1992 | Johnston ............... 604/249 |
| 5,095,309 A | | 3/1992 | Troyk et al. |
| 5,096,271 A | | 3/1992 | Portman |
| 5,097,831 A | | 3/1992 | Lekholm |
| 5,098,384 A | | 3/1992 | Abrams |
| 5,103,832 A | | 4/1992 | Jackson |
| 5,105,810 A | | 4/1992 | Collins et al. |
| 5,107,850 A | | 4/1992 | Olive |
| 5,112,344 A | | 5/1992 | Petros et al. |
| 5,113,859 A | | 5/1992 | Funke et al. |
| 5,113,869 A | | 5/1992 | Nappholz et al. |
| 5,115,676 A | | 5/1992 | Lee |
| 5,117,825 A | | 6/1992 | Grevious |
| 5,121,777 A | | 6/1992 | Leininger et al. |
| 5,127,451 A | | 7/1992 | Fink, Jr. et al. |
| 5,129,394 A | | 7/1992 | Mehra |
| 5,129,806 A | | 7/1992 | Hehl et al. |
| 5,131,145 A | | 7/1992 | Badoureaux et al. |
| 5,131,388 A | | 7/1992 | Pless et al. |
| 5,133,358 A | | 7/1992 | Gustafson et al. |
| 5,135,488 A | | 8/1992 | Foote et al. |
| 5,139,484 A | | 8/1992 | Hazon et al. |
| 5,144,949 A | | 9/1992 | Olson |
| 5,148,580 A | | 9/1992 | Dyckow et al. |
| 5,148,695 A | | 9/1992 | Ellis |
| 5,152,770 A | | 10/1992 | Bengmark et al. |
| 5,152,776 A | | 10/1992 | Pinchuk |
| 5,154,170 A | | 10/1992 | Bennett et al. |
| 5,154,171 A | | 10/1992 | Chirife et al. |
| 5,154,693 A | | 10/1992 | East et al. |
| 5,156,972 A | | 10/1992 | Issachar |
| 5,158,078 A | | 10/1992 | Bennett et al. |
| 5,161,773 A * | | 11/1992 | Tower ............... 251/5 |
| 5,163,429 A | | 11/1992 | Cohen |
| 5,167,615 A | | 12/1992 | East et al. |
| 5,168,757 A | | 12/1992 | Rabenau et al. |
| 5,168,982 A | | 12/1992 | Hakanen et al. |
| 5,171,299 A | | 12/1992 | Heitzmann et al. |
| 5,173,873 A | | 12/1992 | Wu et al. |
| 5,174,286 A | | 12/1992 | Chirife et al. |
| 5,174,291 A | | 12/1992 | Schoonen et al. |
| 5,176,502 A | | 1/1993 | Sanderson et al. |
| 5,178,197 A | | 1/1993 | Healy |
| 5,181,423 A | | 1/1993 | Philipps et al. |
| 5,181,517 A | | 1/1993 | Hickey |
| 5,184,132 A | | 2/1993 | Baird |
| 5,184,614 A | | 2/1993 | Collins et al. |
| 5,184,619 A | | 2/1993 | Austin |
| 5,185,535 A | | 2/1993 | Farb et al. |
| 5,186,224 A | | 2/1993 | Schirmacher et al. |
| 5,186,431 A * | | 2/1993 | Tamari ............... 251/5 |
| 5,188,106 A | | 2/1993 | Nappholz et al. |
| 5,188,604 A | | 2/1993 | Orth |
| 5,192,314 A | | 3/1993 | Daskalakis |
| 5,195,362 A | | 3/1993 | Eason |
| 5,197,322 A | | 3/1993 | Indravudh |
| 5,199,427 A | | 4/1993 | Strickland |
| 5,199,428 A | | 4/1993 | Obel et al. |
| 5,201,753 A | | 4/1993 | Lampropoulos et al. |
| 5,204,670 A | | 4/1993 | Stinton |
| 5,207,429 A | | 5/1993 | Walmsley et al. |
| 5,209,223 A | | 5/1993 | McGorry et al. |
| 5,209,732 A | | 5/1993 | Lampropoulos et al. |
| 5,211,129 A | | 5/1993 | Taylor et al. |
| 5,211,161 A | | 5/1993 | Stef et al. |
| 5,212,476 A | | 5/1993 | Maloney |
| 5,213,331 A | | 5/1993 | Avanzini |
| 5,215,523 A | | 6/1993 | Williams et al. |
| 5,218,343 A | | 6/1993 | Stobbe et al. |
| 5,218,957 A | | 6/1993 | Strickland |
| 5,226,429 A | | 7/1993 | Kuzmak |
| 5,226,604 A | | 7/1993 | Seiffert et al. |
| 5,230,694 A | | 7/1993 | Rosenblum |
| 5,233,985 A | | 8/1993 | Hudrlik |
| 5,235,326 A | | 8/1993 | Beigel et al. |
| 5,238,217 A * | | 8/1993 | Fell ............... 251/5 |

| | | | | | |
|---|---|---|---|---|---|
| 5,244,269 A | 9/1993 | Harriehausen et al. | 5,431,694 A | 7/1995 | Snaper et al. |
| 5,244,461 A | 9/1993 | Derlien et al. | 5,433,694 A | 7/1995 | Lim et al. |
| 5,246,008 A | 9/1993 | Mueller et al. | 5,437,605 A | 8/1995 | Helmy et al. |
| 5,249,858 A | 10/1993 | Nusser | 5,443,215 A | 8/1995 | Fackler |
| 5,250,020 A | 10/1993 | Bley | 5,447,519 A | 9/1995 | Peterson |
| 5,254,096 A | 10/1993 | Rondelet et al. | 5,449,368 A | 9/1995 | Kuzmak |
| 5,256,157 A | 10/1993 | Samiotes et al. | 5,456,690 A | 10/1995 | Duong-Van |
| 5,263,244 A | 11/1993 | Centa et al. | 5,461,390 A | 10/1995 | Hoshen |
| 5,263,981 A | 11/1993 | Polyak et al. | 5,464,435 A | 11/1995 | Neumann |
| 5,267,940 A | 12/1993 | Moulder | 5,467,627 A | 11/1995 | Smith et al. |
| 5,267,942 A | 12/1993 | Saperston | 5,474,226 A | 12/1995 | Joseph |
| 5,269,891 A | 12/1993 | Colin et al. | 5,479,818 A | 1/1996 | Walter et al. |
| 5,271,395 A | 12/1993 | Wahlstrand et al. | 5,482,049 A | 1/1996 | Addiss et al. |
| 5,274,859 A | 1/1994 | Redman et al. | 5,487,760 A | 1/1996 | Villafana |
| 5,280,789 A | 1/1994 | Potts | 5,493,738 A | 2/1996 | Sanderson et al. |
| 5,282,839 A | 2/1994 | Roline et al. | 5,494,036 A | 2/1996 | Uber, III et al. |
| 5,282,840 A | 2/1994 | Hudrlik | 5,494,193 A | 2/1996 | Kirschner et al. |
| 5,291,894 A | 3/1994 | Nagy et al. | 5,504,474 A | 4/1996 | Libman et al. |
| 5,292,219 A | 3/1994 | Merin et al. | 5,505,916 A | 4/1996 | Berry, Jr. |
| 5,295,967 A | 3/1994 | Rondelet et al. | 5,507,412 A | 4/1996 | Ebert et al. |
| 5,298,022 A | 3/1994 | Bernardi et al. | 5,507,737 A | 4/1996 | Palmskog et al. |
| 5,298,884 A | 3/1994 | Gilmore et al. | 5,507,785 A | 4/1996 | Deno |
| 5,300,093 A | 4/1994 | Koestner et al. | 5,509,888 A | 4/1996 | Miller |
| 5,300,120 A | 4/1994 | Knapp et al. | 5,509,891 A | 4/1996 | DeRidder |
| 5,304,112 A | 4/1994 | Mrklas et al. | 5,513,945 A | 5/1996 | Hartmann et al. |
| 5,305,923 A | 4/1994 | Kirschner et al. | 5,514,103 A | 5/1996 | Srisathapat et al. |
| 5,312,443 A | 5/1994 | Adams et al. | 5,518,504 A | 5/1996 | Polyak |
| 5,312,452 A | 5/1994 | Salo | 5,520,606 A | 5/1996 | Schoolman et al. |
| 5,312,453 A | 5/1994 | Shelton et al. | 5,523,740 A | 6/1996 | Burgmann et al. |
| 5,313,953 A | 5/1994 | Yomtov et al. | 5,534,018 A | 7/1996 | Wahlstrand et al. |
| 5,314,451 A | 5/1994 | Mulier | 5,535,752 A | 7/1996 | Halperin et al. |
| 5,314,457 A | 5/1994 | Jeutter et al. | 5,538,005 A | 7/1996 | Harrison et al. |
| 5,324,315 A | 6/1994 | Grevious | 5,541,857 A | 7/1996 | Walter et al. |
| 5,325,834 A | 7/1994 | Ballheimer et al. | 5,545,140 A | 8/1996 | Conero et al. |
| 5,326,249 A | 7/1994 | Weissfloch et al. | 5,545,151 A | 8/1996 | O'Connor et al. |
| 5,328,460 A | 7/1994 | Lord et al. | 5,545,186 A | 8/1996 | Olson et al. |
| 5,330,511 A | 7/1994 | Boute et al. | 5,545,214 A | 8/1996 | Stevens |
| 5,337,750 A | 8/1994 | Walloch | 5,547,470 A | 8/1996 | Johnson et al. |
| 5,341,430 A | 8/1994 | Aulia et al. | 5,551,427 A | 9/1996 | Altman |
| 5,342,401 A | 8/1994 | Spano et al. | 5,551,439 A | 9/1996 | Hickey |
| 5,342,406 A | 8/1994 | Thompson | 5,554,185 A | 9/1996 | Block et al. |
| 5,344,388 A | 9/1994 | Maxwell et al. | 5,558,644 A | 9/1996 | Boyd et al. |
| 5,347,476 A | 9/1994 | McBean, Sr. | 5,564,434 A | 10/1996 | Halperin et al. |
| 5,348,210 A | 9/1994 | Linzell et al. | 5,575,770 A | 11/1996 | Melsky et al. |
| 5,348,536 A | 9/1994 | Young et al. | 5,584,803 A | 12/1996 | Stevens et al. |
| 5,350,413 A | 9/1994 | Miller et al. | 5,586,629 A | 12/1996 | Shoberg et al. |
| 5,352,180 A | 10/1994 | Candelon et al. | 5,593,430 A | 1/1997 | Renger |
| 5,353,622 A | 10/1994 | Theener | 5,594,665 A | 1/1997 | Walter et al. |
| 5,353,800 A | 10/1994 | Pohndorf et al. | 5,596,986 A | 1/1997 | Goldfarb |
| 5,354,200 A | 10/1994 | Klein et al. | 5,597,284 A | 1/1997 | Weltlich et al. |
| 5,354,316 A | 10/1994 | Keimel | 5,610,083 A | 3/1997 | Chan et al. |
| 5,354,319 A | 10/1994 | Wyborny et al. | 5,611,768 A | 3/1997 | Tutrone, Jr. |
| 5,360,407 A | 11/1994 | Leonard et al. | 5,612,497 A | 3/1997 | Walter et al. |
| 5,365,462 A | 11/1994 | McBean, Sr. | 5,615,671 A | 4/1997 | Schoonen et al. |
| 5,365,619 A | 11/1994 | Solomon | 5,619,991 A | 4/1997 | Sloane |
| 5,365,985 A | 11/1994 | Todd et al. | 5,625,946 A | 5/1997 | Wildeson et al. |
| 5,368,040 A | 11/1994 | Carney | 5,626,623 A | 5/1997 | Kieval et al. |
| 5,370,665 A | 12/1994 | Hudrlik | 5,626,630 A | 5/1997 | Markowitz et al. |
| 5,373,852 A | 12/1994 | Harrison et al. | 5,630,836 A | 5/1997 | Prem et al. |
| 5,375,073 A | 12/1994 | McBean | 5,634,255 A | 6/1997 | Bishop et al. |
| 5,377,128 A | 12/1994 | McBean | 5,637,083 A | 6/1997 | Bertrand et al. |
| 5,378,231 A | 1/1995 | Johnson et al. | 5,643,207 A | 7/1997 | Rise |
| 5,382,232 A | 1/1995 | Hague et al. | 5,645,116 A | 7/1997 | McDonald |
| 5,383,915 A | 1/1995 | Adams | 5,650,766 A | 7/1997 | Burgmann et al. |
| 5,388,578 A | 2/1995 | Yomtov et al. | 5,673,585 A | 10/1997 | Bishop et al. |
| 5,388,586 A | 2/1995 | Lee et al. | 5,676,690 A | 10/1997 | Noren et al. |
| 5,388,831 A | 2/1995 | Quadri et al. | 5,681,285 A | 10/1997 | Ford et al. |
| 5,394,909 A | 3/1995 | Mitchell et al. | 5,686,831 A | 11/1997 | Vandervalk et al. |
| 5,402,944 A | 4/1995 | Pape et al. | 5,687,734 A | 11/1997 | Dempsey et al. |
| 5,406,957 A | 4/1995 | Tansey | 5,693,076 A | 12/1997 | Kaemmerer |
| 5,409,009 A | 4/1995 | Olson | 5,702,368 A | 12/1997 | Stevens et al. |
| 5,411,031 A | 5/1995 | Yomtov | 5,702,427 A | 12/1997 | Ecker et al. |
| 5,411,551 A | 5/1995 | Winston et al. | 5,702,431 A | 12/1997 | Wang et al. |
| 5,411,552 A | 5/1995 | Andersen et al. | 5,704,352 A | 1/1998 | Tremblay et al. |
| 5,416,372 A | 5/1995 | Ljungstroem et al. | 5,715,786 A | 2/1998 | Seiberth et al. |
| 5,417,226 A | 5/1995 | Juma | 5,715,837 A | 2/1998 | Chen |
| 5,417,717 A | 5/1995 | Salo et al. | 5,720,436 A | 2/1998 | Buschor et al. |
| 5,425,362 A | 6/1995 | Siker et al. | 5,730,101 A | 3/1998 | Aupperle et al. |
| 5,431,171 A | 7/1995 | Harrison et al. | 5,732,710 A | 3/1998 | Rabinovich et al. |

| | | |
|---|---|---|
| 5,733,313 A | 3/1998 | Barreras, Sr. et al. |
| 5,738,652 A | 4/1998 | Boyd et al. |
| 5,742,233 A | 4/1998 | Hoffman et al. |
| 5,743,267 A | 4/1998 | Nikolic et al. |
| 5,749,369 A | 5/1998 | Rabinovich et al. |
| 5,749,909 A | 5/1998 | Schroeppel et al. |
| 5,755,687 A | 5/1998 | Donlon |
| 5,755,748 A | 5/1998 | Borza et al. |
| 5,765,568 A | 6/1998 | Sweezer, Jr. et al. |
| 5,769,812 A | 6/1998 | Stevens et al. |
| 5,771,903 A | 6/1998 | Jakobsson |
| 5,782,774 A | 7/1998 | Shmulewitz |
| 5,787,520 A | 8/1998 | Dunbar |
| 5,791,344 A | 8/1998 | Schulman et al. |
| 5,792,094 A | 8/1998 | Stevens et al. |
| 5,792,179 A | 8/1998 | Sideris |
| 5,795,325 A | 8/1998 | Valley et al. |
| 5,796,827 A | 8/1998 | Coppersmith et al. |
| 5,800,375 A | 9/1998 | Sweezer et al. |
| 5,807,265 A | 9/1998 | Itoigawa et al. |
| 5,807,336 A | 9/1998 | Russo et al. |
| 5,810,015 A | 9/1998 | Flaherty |
| 5,810,757 A | 9/1998 | Sweezer, Jr. et al. |
| 5,814,016 A | 9/1998 | Valley et al. |
| 5,817,093 A | 10/1998 | Williamson, IV et al. |
| 5,833,603 A | 11/1998 | Kovacs et al. |
| 5,836,300 A | 11/1998 | Mault |
| 5,836,886 A | 11/1998 | Itoigawa et al. |
| 5,840,081 A | 11/1998 | Andersen et al. |
| 5,849,225 A | 12/1998 | Ebina et al. |
| 5,855,597 A | 1/1999 | Jayaraman et al. |
| 5,855,601 A | 1/1999 | Bessler et al. |
| 5,860,938 A | 1/1999 | Lafontaine et al. |
| 5,861,018 A | 1/1999 | Feierbach |
| 5,863,366 A | 1/1999 | Snow |
| 5,868,702 A | 2/1999 | Stevens et al. |
| 5,873,837 A | 2/1999 | Lieber et al. |
| 5,875,953 A | 3/1999 | Shioya et al. |
| 5,879,499 A | 3/1999 | Corvi |
| 5,881,919 A | 3/1999 | Womac et al. |
| 5,885,238 A | 3/1999 | Stevens et al. |
| 5,887,475 A | 3/1999 | Muldner |
| 5,899,927 A | 5/1999 | Ecker et al. |
| 5,916,179 A | 6/1999 | Sharrock |
| 5,916,237 A | 6/1999 | Schu |
| 5,935,078 A | 8/1999 | Feierbach |
| 5,938,669 A | 8/1999 | Klaiber et al. |
| 5,951,487 A | 9/1999 | Brehmeier-Flick et al. |
| 5,957,861 A | 9/1999 | Combs et al. |
| 5,967,986 A | 10/1999 | Cimochowski et al. |
| 5,971,934 A | 10/1999 | Scherer et al. |
| 5,974,873 A | 11/1999 | Nelson et al. |
| 5,978,985 A | 11/1999 | Thurman |
| 5,995,874 A | 11/1999 | Borza et al. |
| 6,015,386 A | 1/2000 | Kensey et al. |
| 6,015,387 A | 1/2000 | Schwartz et al. |
| 6,019,729 A | 2/2000 | Itoigawa et al. |
| 6,024,704 A | 2/2000 | Meador et al. |
| 6,030,413 A | 2/2000 | Lazarus |
| 6,035,461 A | 3/2000 | Nguyen |
| 6,053,873 A | 4/2000 | Govari et al. |
| 6,056,723 A | 5/2000 | Donlon |
| 6,058,330 A | 5/2000 | Borza et al. |
| 6,059,757 A | 5/2000 | Macoviak et al. |
| 6,067,474 A | 5/2000 | Schulman et al. |
| 6,067,991 A * | 5/2000 | Forsell .................... 128/899 |
| 6,076,016 A | 6/2000 | Feierbach |
| 6,083,174 A | 7/2000 | Brehmeier-Flick et al. |
| 6,090,096 A | 7/2000 | St. Goar et al. |
| 6,102,678 A | 8/2000 | Peclat et al. |
| 6,102,856 A | 8/2000 | Groff et al. |
| 6,102,922 A | 8/2000 | Jakobsson et al. |
| 6,106,477 A | 8/2000 | Miesel et al. |
| 6,106,551 A | 8/2000 | Crossett et al. |
| 6,110,145 A | 8/2000 | Macoviak |
| 6,113,553 A | 9/2000 | Chubbuck |
| 6,131,664 A | 10/2000 | Sonnier |
| 6,135,945 A | 10/2000 | Sultan |
| 6,138,984 A * | 10/2000 | Abell .................... 251/5 |
| 6,146,394 A * | 11/2000 | Morejohn et al. .................... 606/158 |
| 6,159,156 A | 12/2000 | Van Bockel et al. |
| 6,162,180 A | 12/2000 | Miesel et al. |
| 6,162,245 A | 12/2000 | Jayaraman et al. |
| 6,168,614 B1 | 1/2001 | Andersen et al. |
| 6,221,057 B1 * | 4/2001 | Schwartz et al. .................... 604/246 |
| 6,231,543 B1 * | 5/2001 | Hegde et al. .................... 604/96.01 |
| 6,234,745 B1 | 5/2001 | Pugh et al. |
| 6,240,316 B1 | 5/2001 | Richmond et al. |
| 6,240,318 B1 | 5/2001 | Phillips |
| 6,245,102 B1 | 6/2001 | Jayaraman |
| 6,248,080 B1 | 6/2001 | Miesel et al. |
| 6,251,093 B1 | 6/2001 | Valley et al. |
| 6,269,819 B1 | 8/2001 | Oz et al. |
| 6,277,078 B1 | 8/2001 | Porat et al. |
| 6,292,697 B1 | 9/2001 | Roberts |
| 6,309,350 B1 | 10/2001 | VanTassel et al. |
| 6,315,769 B1 | 11/2001 | Peer et al. |
| 6,319,208 B1 | 11/2001 | Abita et al. |
| 6,328,699 B1 | 12/2001 | Eigler et al. |
| 6,338,735 B1 | 1/2002 | Stevens |
| 6,357,438 B1 | 3/2002 | Hansen |
| 6,360,122 B1 | 3/2002 | Fischell et al. |
| 6,360,822 B1 | 3/2002 | Robertson et al. |
| 6,366,817 B1 | 4/2002 | Kung |
| 6,379,308 B1 | 4/2002 | Brockway et al. |
| 6,379,380 B1 | 4/2002 | Satz |
| 6,398,752 B1 | 6/2002 | Sweezer, Jr. et al. |
| 6,398,760 B1 * | 6/2002 | Danby .................... 604/132 |
| 6,409,674 B1 | 6/2002 | Brockway et al. |
| 6,423,031 B1 | 7/2002 | Donlon |
| 6,430,444 B1 | 8/2002 | Borza et al. |
| 6,431,175 B1 | 8/2002 | Penner et al. |
| 6,432,040 B1 | 8/2002 | Meah |
| 6,443,887 B1 | 9/2002 | Derus et al. |
| 6,443,893 B1 | 9/2002 | Schnakenberg et al. |
| 6,450,173 B1 | 9/2002 | Forsell et al. |
| 6,450,946 B1 | 9/2002 | Forsell et al. |
| 6,453,907 B1 | 9/2002 | Forsell et al. |
| 6,454,698 B1 | 9/2002 | Forsell et al. |
| 6,454,699 B1 | 9/2002 | Forsell et al. |
| 6,454,700 B1 | 9/2002 | Forsell et al. |
| 6,454,701 B1 | 9/2002 | Forsell et al. |
| 6,460,543 B1 * | 10/2002 | Forsell .................... 128/898 |
| 6,461,292 B1 | 10/2002 | Forsell et al. |
| 6,461,293 B1 | 10/2002 | Forsell et al. |
| 6,463,329 B1 | 10/2002 | Goedeke |
| 6,463,935 B1 | 10/2002 | Forsell et al. |
| 6,464,628 B1 | 10/2002 | Forsell et al. |
| 6,470,212 B1 | 10/2002 | Weijand et al. |
| 6,470,892 B1 | 10/2002 | Forsell et al. |
| 6,471,635 B1 | 10/2002 | Forsell et al. |
| 6,475,136 B1 | 11/2002 | Forsell et al. |
| 6,475,170 B1 | 11/2002 | Doron et al. |
| 6,482,145 B1 | 11/2002 | Forsell et al. |
| 6,482,171 B1 | 11/2002 | Corvi et al. |
| 6,482,177 B1 | 11/2002 | Leinders et al. |
| 6,486,588 B2 | 11/2002 | Doron et al. |
| 6,503,189 B1 | 1/2003 | Forsell et al. |
| 6,504,286 B1 | 1/2003 | Porat et al. |
| 6,531,739 B2 | 3/2003 | Cable et al. |
| 6,533,719 B2 | 3/2003 | Kuyava et al. |
| 6,533,733 B1 | 3/2003 | Ericson et al. |
| 6,542,350 B1 | 4/2003 | Rogers |
| 6,544,220 B2 * | 4/2003 | Shuman et al. .................... 604/99.04 |
| 6,558,321 B1 | 5/2003 | Burd et al. |
| 6,558,994 B2 | 5/2003 | Cha et al. |
| 6,573,563 B2 | 6/2003 | Lee et al. |
| 6,582,462 B1 | 6/2003 | Andersen et al. |
| 6,599,250 B2 | 7/2003 | Webb et al. |
| 6,605,112 B1 | 8/2003 | Moll et al. |
| 6,629,534 B1 | 10/2003 | St. Goar et al. |
| 6,638,208 B1 * | 10/2003 | Natarajan et al. .................... 600/30 |
| 6,640,137 B2 | 10/2003 | MacDonald |
| 6,641,610 B2 | 11/2003 | Wolf et al. |
| 6,645,143 B2 | 11/2003 | VanTassel et al. |
| 6,673,109 B2 | 1/2004 | Cox |
| 6,678,561 B2 | 1/2004 | Forsell et al. |
| 6,682,480 B1 | 1/2004 | Habib et al. |

| Patent/Publication | Date | Inventor |
|---|---|---|
| 6,682,503 B1 | 1/2004 | Fariss et al. |
| 6,682,559 B2 | 1/2004 | Myers et al. |
| 6,695,866 B1 | 2/2004 | Kuehn et al. |
| 6,709,385 B2 | 3/2004 | Forsell et al. |
| 6,718,200 B2 | 4/2004 | Marmaropoulos et al. |
| 6,719,787 B2 | 4/2004 | Cox |
| 6,719,788 B2 | 4/2004 | Cox |
| 6,719,789 B2 | 4/2004 | Cox |
| 6,731,976 B2 | 5/2004 | Penn et al. |
| 6,733,525 B2 | 5/2004 | Yang et al. |
| 6,736,846 B2 | 5/2004 | Cox |
| 6,752,813 B2 | 6/2004 | Goldfarb et al. |
| 6,764,461 B2 * | 7/2004 | Mickley et al. ............... 604/15 |
| 6,796,942 B1 | 9/2004 | Kreiner et al. |
| 6,822,343 B2 | 11/2004 | Estevez |
| 6,851,628 B1 | 2/2005 | Garrison et al. |
| 6,855,115 B2 | 2/2005 | Fonseca et al. |
| 6,889,772 B2 | 5/2005 | Buytaert et al. |
| 6,890,300 B2 | 5/2005 | Lloyd et al. |
| 6,896,651 B2 | 5/2005 | Gross et al. |
| 6,896,690 B1 | 5/2005 | Lambrecht et al. |
| 6,913,600 B2 | 7/2005 | Valley et al. |
| 6,915,165 B2 | 7/2005 | Forsell et al. |
| 6,926,246 B2 | 8/2005 | Ginggen et al. |
| 6,929,653 B2 | 8/2005 | Strecter |
| 6,932,792 B1 | 8/2005 | St. Goar et al. |
| 6,951,229 B2 | 10/2005 | Garrison et al. |
| 6,951,571 B1 | 10/2005 | Srivastava |
| 6,953,429 B2 | 10/2005 | Forsell et al. |
| 6,961,619 B2 | 11/2005 | Casey |
| 6,970,742 B2 | 11/2005 | Mann et al. |
| 6,979,350 B2 | 12/2005 | Moll et al. |
| 6,985,078 B2 | 1/2006 | Suzuki et al. |
| 6,989,027 B2 | 1/2006 | Allen et al. |
| 7,011,095 B2 | 3/2006 | Wolf et al. |
| 7,011,624 B2 | 3/2006 | Forsell et al. |
| 7,017,583 B2 | 3/2006 | Forsell et al. |
| 7,018,406 B2 | 3/2006 | Seguin et al. |
| 7,021,402 B2 | 4/2006 | Beato et al. |
| 7,025,727 B2 | 4/2006 | Brockway et al. |
| 7,044,920 B2 | 5/2006 | Letort et al. |
| 7,060,080 B2 | 6/2006 | Bachmann et al. |
| 7,081,683 B2 | 7/2006 | Ariav et al. |
| 7,109,933 B2 | 9/2006 | Ito et al. |
| 7,118,086 B1 * | 10/2006 | Borglum et al. ............... 251/5 |
| 7,131,447 B2 | 11/2006 | Sterman et al. |
| 7,131,945 B2 | 11/2006 | Fink et al. |
| 7,134,580 B2 | 11/2006 | Garrison et al. |
| 7,144,400 B2 | 12/2006 | Byrum et al. |
| 7,147,640 B2 | 12/2006 | Huebner et al. |
| 7,153,262 B2 | 12/2006 | Stivoric et al. |
| 7,187,978 B2 | 3/2007 | Malek et al. |
| 7,225,032 B2 | 5/2007 | Schmeling et al. |
| 7,257,438 B2 | 8/2007 | Kinast |
| 7,285,090 B2 | 10/2007 | Stivoric et al. |
| 7,530,943 B2 * | 5/2009 | Lechner ............... 600/37 |
| 7,658,196 B2 * | 2/2010 | Ferreri et al. ............... 128/899 |
| 7,798,954 B2 * | 9/2010 | Birk et al. ............... 600/37 |
| 7,846,126 B2 * | 12/2010 | Steen et al. ............... 604/28 |
| 2001/0011543 A1 | 8/2001 | Forsell |
| 2001/0041823 A1 * | 11/2001 | Snyder et al. ............... 600/31 |
| 2002/0049394 A1 | 4/2002 | Roy et al. |
| 2002/0111644 A1 * | 8/2002 | Shuman et al. ............... 606/167 |
| 2002/0120200 A1 | 8/2002 | Brockway et al. |
| 2002/0138009 A1 | 9/2002 | Brockway et al. |
| 2002/0177782 A1 | 11/2002 | Penner |
| 2003/0009201 A1 | 1/2003 | Forsell |
| 2003/0030893 A1 | 2/2003 | Cornelius et al. |
| 2003/0032857 A1 | 2/2003 | Forsell |
| 2003/0037591 A1 | 2/2003 | Ashton et al. |
| 2003/0045775 A1 | 3/2003 | Forsell |
| 2003/0066536 A1 | 4/2003 | Forsell |
| 2003/0088148 A1 | 5/2003 | Forsell |
| 2003/0092962 A1 | 5/2003 | Forsell |
| 2003/0093117 A1 | 5/2003 | Saadat |
| 2003/0100929 A1 | 5/2003 | Forsell |
| 2003/0105385 A1 | 6/2003 | Forsell |
| 2003/0109771 A1 | 6/2003 | Forsell |
| 2003/0114729 A1 | 6/2003 | Forsell |
| 2003/0125605 A1 | 7/2003 | Forsell |
| 2003/0125768 A1 | 7/2003 | Peter |
| 2003/0135089 A1 | 7/2003 | Forsell |
| 2003/0135090 A1 | 7/2003 | Forsell |
| 2003/0136417 A1 | 7/2003 | Fonseca et al. |
| 2003/0144648 A1 | 7/2003 | Forsell |
| 2003/0163079 A1 | 8/2003 | Burnett |
| 2003/0183536 A1 * | 10/2003 | Eden ............... 205/775.5 |
| 2003/0216666 A1 | 11/2003 | Ericson et al. |
| 2004/0054352 A1 | 3/2004 | Adams et al. |
| 2004/0092865 A1 * | 5/2004 | Flaherty et al. ............... 604/93.01 |
| 2004/0093007 A1 * | 5/2004 | Sussman et al. ............... 606/194 |
| 2004/0113790 A1 | 6/2004 | Hamel et al. |
| 2004/0133092 A1 | 7/2004 | Kain |
| 2004/0147969 A1 | 7/2004 | Mann et al. |
| 2004/0172087 A1 | 9/2004 | Forsell |
| 2004/0186396 A1 | 9/2004 | Roy et al. |
| 2004/0254537 A1 | 12/2004 | Conlon et al. |
| 2005/0015014 A1 | 1/2005 | Fonseca et al. |
| 2005/0025979 A1 | 2/2005 | Sandt et al. |
| 2005/0027175 A1 | 2/2005 | Yang |
| 2005/0038328 A1 | 2/2005 | Stoehrer et al. |
| 2005/0054971 A1 * | 3/2005 | Steen et al. ............... 604/22 |
| 2005/0061079 A1 | 3/2005 | Schulman |
| 2005/0102026 A1 | 5/2005 | Turner et al. |
| 2005/0159789 A1 | 7/2005 | Brockway et al. |
| 2005/0165317 A1 | 7/2005 | Turner et al. |
| 2005/0182330 A1 | 8/2005 | Brockway et al. |
| 2005/0187482 A1 | 8/2005 | O'Brien et al. |
| 2005/0187488 A1 | 8/2005 | Wolf |
| 2005/0192642 A1 | 9/2005 | Forsell |
| 2005/0240155 A1 | 10/2005 | Conlon |
| 2005/0240156 A1 | 10/2005 | Conlon |
| 2005/0250979 A1 | 11/2005 | Coe |
| 2005/0267406 A1 | 12/2005 | Hassler |
| 2005/0267500 A1 | 12/2005 | Hassler et al. |
| 2005/0272968 A1 * | 12/2005 | Byrum et al. ............... 600/31 |
| 2005/0277960 A1 | 12/2005 | Hassler et al. |
| 2005/0277974 A1 | 12/2005 | Hassler et al. |
| 2005/0288604 A1 | 12/2005 | Eigler et al. |
| 2005/0288720 A1 | 12/2005 | Ross et al. |
| 2005/0288721 A1 | 12/2005 | Girouard et al. |
| 2005/0288739 A1 | 12/2005 | Hassler et al. |
| 2005/0288740 A1 | 12/2005 | Hassler et al. |
| 2005/0288741 A1 | 12/2005 | Hassler et al. |
| 2005/0288742 A1 | 12/2005 | Giordano et al. |
| 2006/0002035 A1 | 1/2006 | Gao et al. |
| 2006/0010090 A1 | 1/2006 | Brockway et al. |
| 2006/0020224 A1 | 1/2006 | Geiger |
| 2006/0020305 A1 | 1/2006 | Desai et al. |
| 2006/0035446 A1 | 2/2006 | Chang et al. |
| 2006/0047205 A1 | 3/2006 | Ludomirsky et al. |
| 2006/0049714 A1 | 3/2006 | Liu et al. |
| 2006/0058627 A1 | 3/2006 | Flaherty et al. |
| 2006/0064134 A1 | 3/2006 | Mazar et al. |
| 2006/0085051 A1 | 4/2006 | Fritsch |
| 2006/0089571 A1 | 4/2006 | Gertner |
| 2006/0094966 A1 | 5/2006 | Brockway et al. |
| 2006/0100531 A1 | 5/2006 | Moser |
| 2006/0113187 A1 | 6/2006 | Deng et al. |
| 2006/0122285 A1 | 6/2006 | Falloon et al. |
| 2006/0122863 A1 | 6/2006 | Gottesman et al. |
| 2006/0142635 A1 | 6/2006 | Forsell |
| 2006/0149124 A1 | 7/2006 | Forsell |
| 2006/0149324 A1 | 7/2006 | Mann et al. |
| 2006/0149327 A1 | 7/2006 | Hedberg et al. |
| 2006/0157701 A1 | 7/2006 | Bauer et al. |
| 2006/0161186 A1 | 7/2006 | Hassler et al. |
| 2006/0161196 A1 * | 7/2006 | Widgerow ............... 606/192 |
| 2006/0178617 A1 | 8/2006 | Adams et al. |
| 2006/0178695 A1 | 8/2006 | Decant et al. |
| 2006/0183967 A1 | 8/2006 | Lechner |
| 2006/0184206 A1 | 8/2006 | Baker et al. |
| 2006/0189887 A1 | 8/2006 | Hassler et al. |
| 2006/0189888 A1 | 8/2006 | Hassler et al. |
| 2006/0189889 A1 | 8/2006 | Gertner |
| 2006/0199997 A1 | 9/2006 | Hassler et al. |
| 2006/0211912 A1 | 9/2006 | Dlugos et al. |
| 2006/0211913 A1 | 9/2006 | Dlugos et al. |

| | | | | | | |
|---|---|---|---|---|---|---|
| 2006/0211914 A1 | 9/2006 | Hassler et al. | | EP | 1253880 | 11/2002 |
| 2006/0217668 A1 | 9/2006 | Schulze et al. | | EP | 1253881 | 11/2002 |
| 2006/0217673 A1 | 9/2006 | Schulze et al. | | EP | 1253883 | 11/2002 |
| 2006/0235310 A1 | 10/2006 | O'Brien et al. | | EP | 1253888 | 11/2002 |
| 2006/0235439 A1 | 10/2006 | Molitor et al. | | EP | 1255511 | 11/2002 |
| 2006/0235448 A1 | 10/2006 | Roslin et al. | | EP | 1255513 | 11/2002 |
| 2006/0244914 A1 | 11/2006 | Cech et al. | | EP | 1255514 | 11/2002 |
| 2006/0247682 A1 | 11/2006 | Gerber et al. | | EP | 1263355 | 12/2002 |
| 2006/0247719 A1 | 11/2006 | Maschino et al. | | EP | 1263357 | 12/2002 |
| 2006/0247721 A1 | 11/2006 | Maschino et al. | | EP | 1284691 | 2/2003 |
| 2006/0247722 A1 | 11/2006 | Maschino et al. | | EP | 1374758 | 1/2004 |
| 2006/0247723 A1 | 11/2006 | Gerber et al. | | EP | 1488735 | 12/2004 |
| 2006/0247724 A1 | 11/2006 | Gerber et al. | | EP | 1500411 | 1/2005 |
| 2006/0247725 A1 | 11/2006 | Gerber et al. | | EP | 1510306 | 3/2005 |
| 2006/0252982 A1 | 11/2006 | Hassler et al. | | EP | 1518514 | 3/2005 |
| 2006/0293625 A1 | 12/2006 | Hunt et al. | | EP | 1545303 | 6/2005 |
| 2006/0293626 A1 | 12/2006 | Byrum et al. | | EP | 1547549 | 6/2005 |
| 2006/0293627 A1 | 12/2006 | Byrum et al. | | EP | 1563814 | 8/2005 |
| 2007/0010790 A1 | 1/2007 | Byrum et al. | | EP | 1568338 | 8/2005 |
| 2007/0027356 A1 | 2/2007 | Ortiz | | EP | 1582175 | 10/2005 |
| 2007/0027493 A1 | 2/2007 | Ben-Haim et al. | | EP | 1582176 | 10/2005 |
| 2007/0067206 A1 | 3/2007 | Haggerty et al. | | EP | 1584303 | 10/2005 |
| 2007/0070906 A1 | 3/2007 | Thakur | | EP | 1586283 | 10/2005 |
| 2007/0072452 A1 | 3/2007 | Inagaki et al. | | EP | 1591086 | 11/2005 |
| 2007/0081304 A1 | 4/2007 | Takeguchi | | EP | 1593359 | 11/2005 |
| 2007/0156013 A1* | 7/2007 | Birk .................. 600/37 | | EP | 1598030 | 11/2005 |
| 2007/0161958 A1 | 7/2007 | Glenn | | EP | 1609440 | 12/2005 |
| 2007/0167672 A1 | 7/2007 | Dlugos et al. | | EP | 1674033 | 6/2006 |
| 2007/0173881 A1 | 7/2007 | Birk et al. | | EP | 1736123 | 12/2006 |
| 2007/0179583 A1 | 8/2007 | Goetzinger et al. | | EP | 1799119 | 6/2007 |
| 2007/0185462 A1* | 8/2007 | Byrum .................. 604/288.02 | | EP | 1815881 A1 | 8/2007 |
| 2007/0208313 A1 | 9/2007 | Conlon et al. | | GB | 2355937 | 5/2001 |
| 2007/0225781 A1 | 9/2007 | Saadat et al. | | WO | WO-8911244 | 11/1989 |
| 2008/0009680 A1* | 1/2008 | Hassler .................. 600/300 | | WO | WO-8911701 | 11/1989 |
| 2009/0171375 A1* | 7/2009 | Coe et al. .................. 606/151 | | WO | WO-9004368 | 5/1990 |
| 2009/0171378 A1 | 7/2009 | Coe et al. | | WO | WO-9511057 | 4/1995 |
| 2009/0171379 A1 | 7/2009 | Coe et al. | | WO | WO-9715351 | 5/1997 |
| 2009/0254106 A1* | 10/2009 | Forsell .................. 606/157 | | WO | WO-9733513 | 9/1997 |
| 2011/0009897 A1* | 1/2011 | Forsell .................. 606/192 | | WO | WO-9833554 | 8/1998 |
| 2011/0071460 A1* | 3/2011 | Steen et al. .................. 604/22 | | WO | WO-9835610 | 8/1998 |
| | | | | WO | WO-9901063 | 1/1999 |
| FOREIGN PATENT DOCUMENTS | | | | WO | WO-9918850 | 4/1999 |
| CA | 1119469 | 3/1982 | | WO | WO-0004945 | 2/2000 |
| CA | 1275135 | 10/1990 | | WO | WO-0009047 A1 | 2/2000 |
| CA | 1277885 | 12/1990 | | WO | WO-0033738 | 6/2000 |
| CA | 1317482 | 5/1993 | | WO | WO-0072899 | 12/2000 |
| CA | 2082015 | 5/1993 | | WO | WO-0104487 | 1/2001 |
| CA | 1327191 | 2/1994 | | WO | WO-0112075 | 2/2001 |
| CA | 2119101 | 9/1994 | | WO | WO-0112076 | 2/2001 |
| CA | 2305998 | 4/1999 | | WO | WO-0112077 | 2/2001 |
| CN | 1059035 | 2/1992 | | WO | WO-0112078 | 2/2001 |
| CN | 1119469 | 3/1996 | | WO | WO-0121066 | 3/2001 |
| CN | 1241003 | 1/2000 | | WO | WO-0136014 | 5/2001 |
| EA | 4581 | 6/2004 | | WO | WO-0145485 | 6/2001 |
| EP | 125387 B1 | 11/1984 | | WO | WO-0145486 | 6/2001 |
| EP | 417171 | 3/1991 | | WO | WO-0147431 | 7/2001 |
| EP | 508141 | 10/1992 | | WO | WO-0147432 | 7/2001 |
| EP | 568730 | 11/1993 | | WO | WO-0147433 | 7/2001 |
| EP | 605302 | 7/1994 | | WO | WO-0147434 | 7/2001 |
| EP | 660482 | 6/1995 | | WO | WO-0147435 | 7/2001 |
| EP | 714017 | 5/1996 | | WO | WO-0147440 | 7/2001 |
| EP | 769340 | 4/1997 | | WO | WO-0147575 | 7/2001 |
| EP | 846475 | 6/1998 | | WO | WO-0148451 | 7/2001 |
| EP | 848780 | 6/1998 | | WO | WO-0149245 | 7/2001 |
| EP | 876808 | 11/1998 | | WO | WO-0150832 | 7/2001 |
| EP | 888079 | 1/1999 | | WO | WO-0150833 | 7/2001 |
| EP | 914059 | 5/1999 | | WO | WO-0154626 | 8/2001 |
| EP | 981293 | 3/2000 | | WO | WO-0158388 | 8/2001 |
| EP | 997680 | 5/2000 | | WO | WO-0158390 | 8/2001 |
| EP | 1003021 | 5/2000 | | WO | WO-0158391 | 8/2001 |
| EP | 1022983 | 8/2000 | | WO | WO-0158393 | 8/2001 |
| EP | 1050265 | 11/2000 | | WO | WO-0160453 | 8/2001 |
| EP | 1115329 | 7/2001 | | WO | WO-0181890 | 11/2001 |
| EP | 1119314 | 8/2001 | | WO | WO-0200118 | 1/2002 |
| EP | 1128871 | 9/2001 | | WO | WO-0215769 | 2/2002 |
| EP | 1202674 | 5/2002 | | WO | WO-0226161 | 4/2002 |
| EP | 1213991 | 6/2002 | | WO | WO-02053228 | 7/2002 |
| EP | 1253877 | 11/2002 | | WO | WO-02055126 | 7/2002 |
| EP | 1253879 | 11/2002 | | WO | WO-02058551 | 8/2002 |

| | | |
|---|---|---|
| WO | WO-02065894 | 8/2002 |
| WO | WO-02076289 | 10/2002 |
| WO | WO-02082984 | 10/2002 |
| WO | WO-02089655 | 11/2002 |
| WO | WO-02090894 | 11/2002 |
| WO | WO-02100481 | 12/2002 |
| WO | WO-03002192 | 1/2003 |
| WO | WO-03002193 | 1/2003 |
| WO | WO-03020182 | 3/2003 |
| WO | WO-03061467 | 7/2003 |
| WO | WO-03061504 | 7/2003 |
| WO | WO-03096889 | 11/2003 |
| WO | WO-2004014456 | 2/2004 |
| WO | WO-2004019773 | 3/2004 |
| WO | WO-2004058101 | 7/2004 |
| WO | WO-2004066879 | 8/2004 |
| WO | WO-2004110263 | 12/2004 |
| WO | WO-2005000206 | 1/2005 |
| WO | WO-2005007075 | 1/2005 |
| WO | WO-2005107583 | 11/2005 |
| WO | WO-2006001851 | 1/2006 |
| WO | WO-2006035446 | 4/2006 |
| WO | WO-2006108203 A2 | 10/2006 |
| WO | WO-2006113187 | 10/2006 |
| WO | WO-2006122285 | 11/2006 |
| WO | WO-2007067206 | 6/2007 |
| WO | WO-2007070906 | 6/2007 |
| WO | WO-2007072452 | 6/2007 |
| WO | WO-2007081304 | 7/2007 |
| WO | WO-2007104356 | 9/2007 |

OTHER PUBLICATIONS

"Application Specific Integrated Circuits (ASICs)", Honeywell product information from website http://www.honeywell.com/sites/portal?smap=aerospace&page=Radiation-Hardened-Electronics3&theme=T18&catID=CE06BEF88-65F8-6A1E-4ED1-6A1EC1B7AE7A&id=HA0E380D3-C27B-9EBF-AAC8-9FAF8851256D&sel=1&sel4=1; 1 page.

"Rad Hard Aerospace Components Products", Honeywell product and service information from website http://www.honeywell.com/sites/portal?smap=aerospace&page=Radiation-Hardened-Electronics3&theme=T6&catID=C815147E4-8786-29FE-49EB-C21C8790AA99&id=H0166BA51-5344-E57E-5C37-C6333EA43F61&sel=1; 1 page.

"Radiation Hardened Electronics and Radiation Technology", Honeywell product and service information from website http://www.honeywell.com/sites/portal?smap=aerospace&page=Radiation-Hardened-Electronics&theme=T4; 2 pages.

Kirchner, G., "Honeywell and Synopsys: Concept-to-Parts Solutions for Next Generation Rad-Hard ASICs", in online magazine Compiler, http://www.synopsys.com/news/pubs/compiler/artlead_redasic-apr05.html, Apr. 2005, 5 pages.

P.A. Neukomm and H. Kundig, "Passive Wireless Actuator Control and Sensor Signal Transmission," Sensors and Actuators, A21-A23 (1990) 258-262.

* cited by examiner

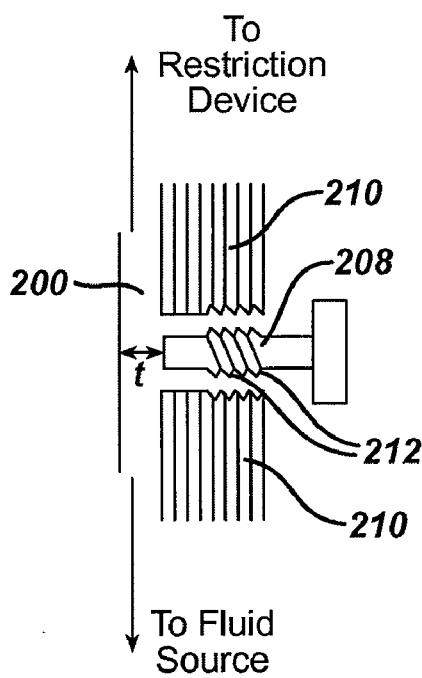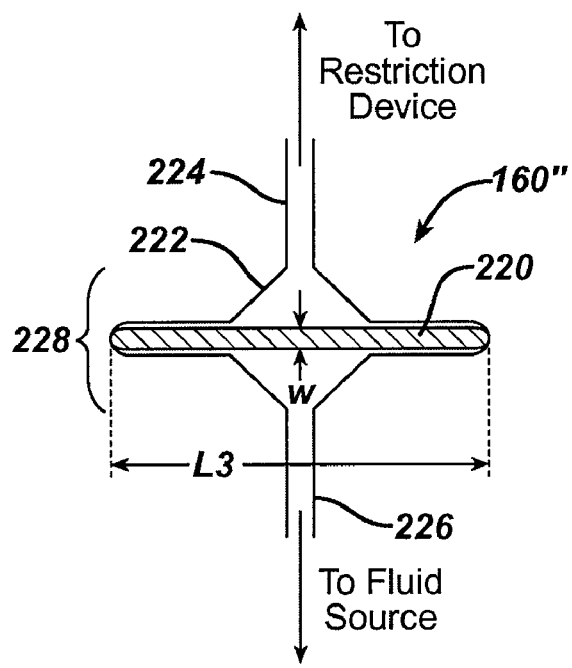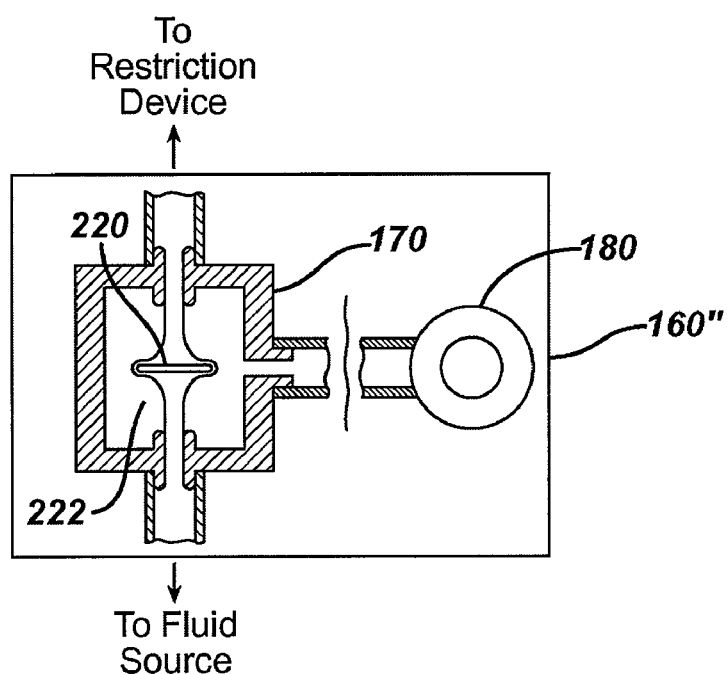

CONTROLLING PRESSURE IN ADJUSTABLE RESTRICTION DEVICES

FIELD OF THE INVENTION

The present invention relates to implantable restriction devices, and in particular to methods and devices for pressure control of fluid in a restriction system.

BACKGROUND OF THE INVENTION

Obesity is becoming a growing concern, particularly in the United States, as the number of obese people continues to increase and more is learned about the negative health effects of obesity. Morbid obesity, in which a person is 100 pounds or more over ideal body weight, in particular poses significant risks for severe health problems. Accordingly, a great deal of attention is being focused on treating obese patients. One method of treating morbid obesity has been to place a restriction device, such as an elongated band, about the upper portion of the stomach. Gastric bands have typically comprised a fluid-filled elastomeric balloon with fixed endpoints that encircles the stomach just inferior to the esophageal-gastric junction to form a small gastric pouch above the band and a reduced stoma opening in the stomach. When fluid is infused into the balloon, the band expands against the stomach creating a food intake restriction or stoma in the stomach. To decrease this restriction, fluid is removed from the band. The effect of the band is to reduce the available stomach volume and thus the amount of food that can be consumed before becoming "full."

With each of the above-described food restriction devices, safe, effective treatment requires that the device be regularly monitored and adjusted to vary the degree of restriction applied to the stomach. With banding devices, the gastric pouch above the band will substantially increase in size following the initial implantation. Accordingly, the stoma opening in the stomach must initially be made large enough to enable the patient to receive adequate nutrition while the stomach adapts to the banding device. As the gastric pouch increases in size, the band may be adjusted to vary the stoma size. In addition, it is desirable to vary the stoma size in order to accommodate changes in the patient's body or treatment regime, or in a more urgent case, to relieve an obstruction or severe esophageal dilatation. Traditionally, adjusting a hydraulic gastric band requires a scheduled clinician visit during which a Huber needle and syringe are used to penetrate the patient's skin and add or remove fluid from the balloon via an injection port. More recently, implantable pumps have been developed which enable non-invasive adjustments of the band. An external programmer communicates with the implanted pump using telemetry to control the pump. During a scheduled visit, a physician places a hand-held portion of the programmer near the gastric implant and transmits power and command signals to the implant. The implant in turn adjusts the fluid levels in the band and transmits a response command to the programmer. While such pumps can be effective, they require power to operate, requiring patients to visit physicians for the pumps to properly operate and be maintained.

Accordingly, there remains a need for methods and devices for regulating a hydraulic restriction system, and in particular for regulating the rate of fluid flow between a restriction device and a fluid source, preferably without the use of power to operate.

SUMMARY OF THE INVENTION

The present invention generally provides methods and devices for regulating a hydraulic restriction system. In one embodiment, a restriction system for forming a restriction in a patient is provided that includes an implantable restriction device configured to form a restriction in a pathway as a function of a volume of fluid contained in the restriction device. The system also includes an adjustable flow control mechanism in fluid communication with the restriction device and configured to define a rate of fluid flow to and from the restriction device.

In one embodiment, the adjustable flow control mechanism can have a geometry that defines a rate of fluid flow to and from the restriction device. The flow control mechanism can be adjustable between a plurality of fixed positions such that increasing the a volume of the geometry increases the rate of fluid flow and decreasing a volume of the geometry decreases the rate of fluid flow. The fluid control mechanism's geometry can be adjusted, for example, through linear motion. In some embodiments, the geometry defines a rate of fluid flow between the restriction device and a fluid reservoir included in the system.

The flow control mechanism can have a variety of configurations. For example, the flow control mechanism can include a flexible tube disposed in a housing and in fluid communication with the restriction device. The geometry of the flexible tube can be adjusted by modifying an amount of fluid within the housing. In some embodiments, the housing is in fluid communication with an implantable port, and the amount of fluid within the housing can be modified through the port. As another example, the flow control mechanism can include a pathway in fluid communication with the restriction device, wherein a geometry of the pathway is configured to be adjusted by adjusting an amount of an obstruction mechanism within the pathway. As yet another example, the flow control mechanism can include a porous membrane.

In other aspects, the flow control mechanism can include a porous member disposed within a fluid-filled housing. Fluid in the housing can be configured to regulate a rate of movement of the porous member through the housing to thereby regulate the rate of fluid flow to and from the restriction device. In an exemplary embodiment, the porous member is coupled to a fluid source in fluid communication with the restriction device such that movement of the porous member through the fluid-filled housing is effective to cause fluid to flow between the fluid source and the restriction device. The flow control mechanism can be regulated by regulating a viscosity of fluid in the fluid-filled housing and/or altering a biasing force of a biasing mechanism coupled to the porous member.

In another embodiment, a restriction system includes an implantable restriction device that can contain a fluid and form a restriction in a pathway corresponding to an amount of fluid in the restriction device. A fluid source can be in fluid communication with the restriction device for receiving fluid from the restriction device to decrease the restriction and for delivering fluid to the restriction device to increase the restriction. The system can further include an adjustable flow control mechanism disposed between the restriction device and the fluid source that can regulate a flow rate of fluid between the fluid source and the restriction device.

The flow control mechanism can have a variety of configurations. For example, the flow control mechanism can have a diameter that is adjustable between at least two positions to regulate the flow rate of fluid. Increasing the diameter can increase the flow rate of fluid, and decreasing the diameter can decrease the flow rate of fluid. As another example, the flow control mechanism can include a flexible tube disposed in a housing and having a diameter that defines the flow rate of fluid. The diameter of the flexible tube can be adjusted by modifying an amount of fluid within the housing. In some embodiments, the housing can be in fluid communication with an implantable port, and the amount of fluid within the housing can be modified through the port. As still another example, the flow control mechanism can include a porous membrane.

The fluid source can also have a variety of configurations. For example, the fluid source can include a pressured fluid reservoir, and the flow control mechanism's fixed diameter can define a flow rate of fluid between the pressured fluid reservoir and the restriction device. Fluid can flow at a rate defined by the flow control mechanism's fixed diameter from the restriction device and through the flow control mechanism to the fluid reservoir when a pressure in the restriction device exceeds a pressure in the fluid reservoir. The pressured fluid reservoir can also have a variety of configurations. In some embodiments, the pressured fluid reservoir includes a cavity in fluid communication with the flow control mechanism and a mechanism configured to apply a biasing force to fluid in the cavity.

In other aspects, a method of forming a restriction in a patient is provided. The method includes implanting a restriction device to form a restriction in a pathway that corresponds to a volume of fluid in the restriction device. The restriction device receives fluid from and delivers fluid to a fluid source at a flow rate defined by a diameter of a flow control mechanism in fluid communication with and disposed between the restriction device and the fluid source. The flow control mechanism's geometry can be adjusted to adjust the flow rate. Increasing the geometry can increase the flow rate, and decreasing the geometry can decrease the flow rate. In some embodiments, the flow control mechanism can include a flexible tube disposed in a fluid cavity, and a geometry of the flexible tube can be adjusted by modifying an amount of fluid within the fluid cavity.

BRIEF DESCRIPTION OF THE DRAWINGS

The invention will be more fully understood from the following detailed description taken in conjunction with the accompanying drawings, in which:

FIG. 13 is a schematic diagram of a variation of the flow control mechanism of FIG. 12;

FIG. 14 is a schematic diagram of still another embodiment of a flow control mechanism that can be used in the food intake restriction system of FIG. 1A;

FIG. 15 is an expanded schematic diagram of the flow control mechanism of FIG. 14;

DETAILED DESCRIPTION OF THE INVENTION

Figure 1A:
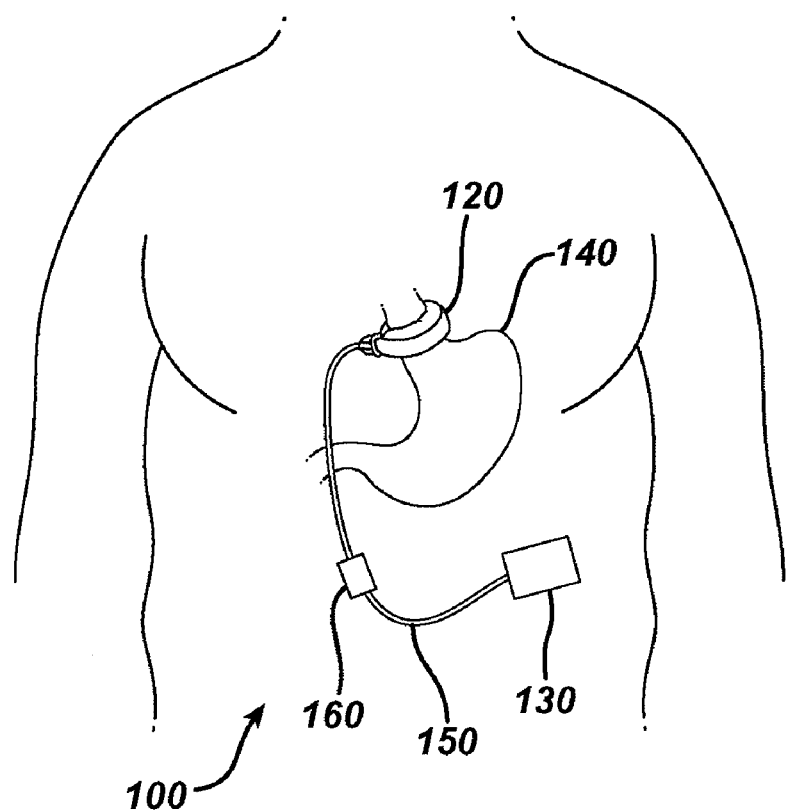
FIG. 1A is a schematic diagram of one embodiment of a food intake restriction system.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for regulating a hydraulic restriction system. In general, the methods and devices can allow for non-invasive pressure control using a flow control mechanism disposed between an implantable restriction device and a fluid source. The flow control mechanism can include an adjustable fluid communication member in fluid communication with the restriction device and the fluid source. In certain embodiments, the geometry of the fluid communication member can control a rate of fluid flow between the restriction device and the fluid source, thereby also regulating a rate at which a pressure of fluid within the restriction device changes. Using the flow control mechanism can provide a time-controlled regulation of pressure of fluid in the restriction device because the larger the geometry of the fluid communication member, the faster fluid can flow between the restriction device and the fluid source, while the smaller the geometry of the fluid communication member, the slower fluid can flow between the restriction device and the fluid source. In other words, the flow control mechanism can provide a delay-controlled regulation of fluid pressure in the restriction device that can be configured to respond more quickly (e.g., with a larger geometry) or more slowly (e.g., with a smaller geometry) to at least one parameter of restriction device function or patient physiology that varies as a function of food intake or other patient physiologic condition. In this way, the flow control mechanism can provide a more constant pressure within the restriction device over time. Because the flow control mechanism can prevent fluid from immediately flowing to or from the restriction device, temporary or transitory changes in the restriction device and/or in the patient (e.g., restriction device pressure increases during eating due to the presence of food and peristaltic waves during swallowing) do not necessarily result in a significant increase or decrease of fluid in the restriction device before the temporary or transitory changes decrease or disappear from effect. In other embodiments, a biasing mechanism, such as a fluid-filled housing for limiting movement of an actuator for driving fluid between the fluid source and restriction device and/or a spring coupled to the actuator, can control the rate of fluid flow between the restriction device and the fluid source. The use of the flow control mechanism can also mechanically regulate a rate of the pressure change of the restriction device without the use of any electrical components that may need to be powered to operate over extended periods of time.

While the present invention can be used with a variety of restriction systems known in the art, in an exemplary embodiment the devices and methods are used with a gastric restriction device. While various types of gastric restriction devices are known, including electrical, mechanical, and/or fluid-based devices, for reference purposes the devices and methods disclosed herein are discussed in connection various embodiments of a fluid-based gastric restriction device as disclosed in commonly-owned U.S. Publication No. 2006/0211913 of Dlugos et al. (hereinafter "Dlugos") filed on Mar. 7, 2006 and entitled "Non-Invasive Pressure Measurement In A Fluid Adjustable Restrictive Device," which is hereby incorporated by reference in its entirety. A person skilled in the art will appreciate that the methods and devices disclosed herein are not intended to be limited to use with any particular restriction device.

Figure 1B:
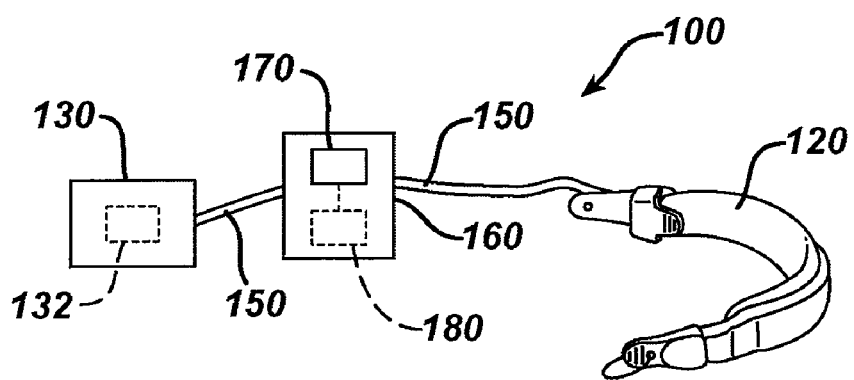
FIG. 1B is a perspective, schematic view of the food intake restriction system of FIG. 1A.

FIGS. 1A-1B illustrate one embodiment of an implantable restriction system 100. As shown, the implantable restriction system 100 generally includes a restriction device, e.g., an adjustable gastric band 120, that is configured to be positioned around the upper portion of a patient's stomach 140 to receive fluid and to form a restriction in a pathway corresponding to an amount of fluid contained therein. The restriction system 100 also includes a pressure control mechanism 130 and a fluid flow control mechanism 160 fluidly coupled, e.g., via a catheter 150 (which can be formed from one or more components), between the band 120 and the pressure control mechanism 130. The pressure control mechanism 130 is configured to control fluid introduction into and fluid removal from one or more elements included in the restriction system 100 to thereby adjust the size of the band 120 and thus the pressure applied to the stomach 140. The flow control mechanism 160 is configured to regulate a flow rate of fluid between the pressure control mechanism 130 and the band 120, thereby regulating a rate of pressure change. Although the flow control mechanism 160 can be disposed anywhere to control a rate of fluid delivery to and from the band 120, in the illustrated embodiment the catheter 150 includes a first portion that is coupled between the band 120 and the flow control mechanism 160 and a second portion that is coupled between the flow control mechanism 160 and the pressure control mechanism 130. Various configurations are possible, including configurations where one or more additional elements are fluidly coupled between any of the band 120, the pressure control mechanism 130, and the flow control mechanism 160, and any known restriction system or device can be used with the present invention.

Figure 2A:
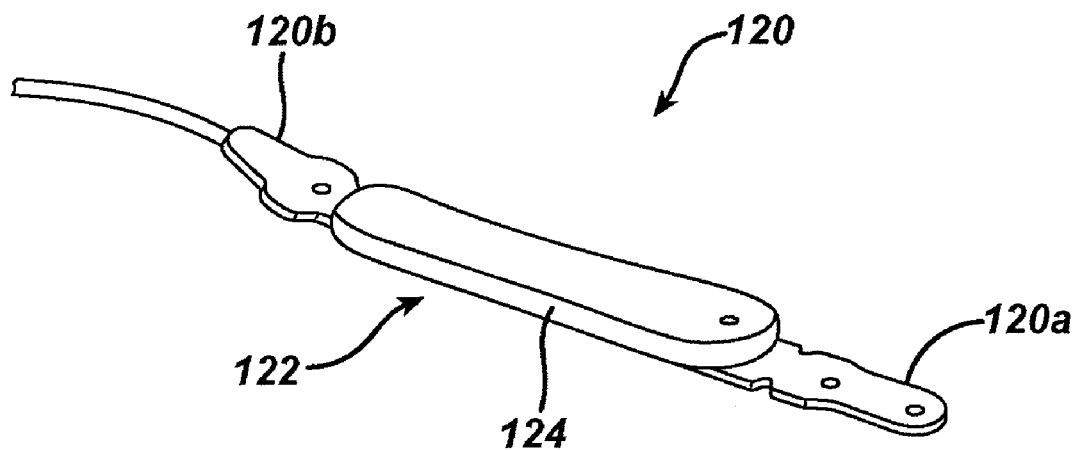
FIG. 2A is a perspective view of a gastric band of the food intake restriction device of FIG. 1A.

FIG. 2A shows the gastric band 120 in more detail. While the gastric band 120 can have a variety of configurations, and various gastric bands known in the art can be used with the present invention, in the illustrated embodiment the gastric band 120 has a generally elongate shape with a support structure 122 having first and second opposite ends 120a, 120b that can be formed in a loop such that the ends are secured to each other. Various mating techniques can be used to secure the ends 120a, 120b to one another. In the illustrated embodiment, the ends 120a, 120b are in the form of straps that mate together, with one laying on top of the other. A support structure can be included at one end of the gastric band 120, and it can have an opening through which the other end of the gastric band 120 can feed through to secure the ends to one another. The gastric band 120 can also include a variable volume member, such as an inflatable balloon 124, that is disposed or formed on an internal side of the support structure 122 and that is configured to be positioned adjacent to tissue. The balloon 124 can expand or contract against the outer wall of the stomach to form an adjustable stoma for controllably restricting food intake into the stomach. The balloon 124 can receive fluid to expand and release fluid to contract. An amount of fluid within the balloon can correspond to an amount of restriction created by the band 120. Thus, adjustment of fluid in the band 120 can be used to control the amount of restriction formed by the band 120.

A person skilled in the art will appreciate that the gastric band 120 can have a variety of other configurations. Moreover, the various methods and devices disclosed herein have equal applicability to other types of implantable bands. For example, bands are used for the treatment of fecal incontinence, as described in U.S. Pat. No. 6,461,292 which is hereby incorporated by reference in its entirety. Bands can also be used to treat urinary incontinence, as described in U.S. Publication No. 2003/0105385 which is hereby incorporated by reference in its entirety. Bands can also be used to treat heartburn and/or acid reflux, as disclosed in U.S. Pat. No. 6,470,892 which is hereby incorporated by reference in its entirety. Bands can also be used to treat impotence, as described in U.S. Publication No. 2003/0114729 which is hereby incorporated by reference in its entirety.

Figure 2B:
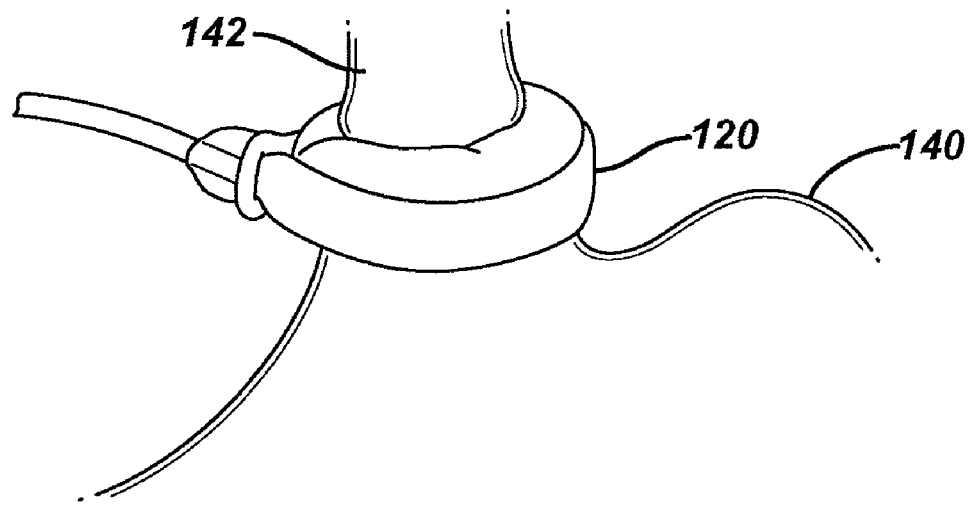
FIG. 2B is a schematic diagram of the gastric band of FIG. 2A applied about the gastro-esophageal junction of a patient.

FIG. 2B shows the adjustable gastric band 120 applied about the gastro-esophageal junction of a patient. As shown, the band 120 at least substantially encloses the upper portion of the stomach 140 near the junction with the patient's esophagus 142. After the band 120 is implanted, preferably in the deflated configuration wherein the band 120 contains little or no fluid, the band 120 can be inflated, e.g., using saline, to decrease the size of the stoma opening. A person skilled in the art will appreciate that various techniques, including those described below, can be used to adjust the amount of restriction formed by the band 120.

The restriction system 100 can also optionally include one or more sensors for sensing one or more parameters related to the system 100, such as pressure of the fluid within the closed fluid circuit of the system 100. While Dlugos discloses a pressure reading device, the sensor could be any sensing device for sensing various parameters of the system 100 or external to the system 100. The sensing device can also have various configurations, and it can be coupled to or positioned anywhere in the restriction system 100. In addition to sensing the pressure of fluid in the closed system, a pressure of fluid within the esophagus 142, the stomach 140, or other body lumen can also be sensed using a sensor, such as an endoscopic manometer. By way of non-limiting example, such fluid pressure measurements can be compared against the measured pressure of fluid within the system 100 before, during, and/or after adjustment of pressure within the system 100. Other suitable uses for measured pressure within the esophagus 142, the stomach 140, or other body lumen will be appreciated by those skilled in the art. The sensor can also be configured to measure various other physiological parameters, as may be desired.

FIG. 1B illustrates the restriction system 100 in more detail. As shown, the flow control mechanism 160 includes a flow control housing 170 and, optionally, an implantable fluid injection port 180 in fluid communication with the control housing 170 (e.g., via the catheter 150). The control housing 170 is also in fluid communication with the band 120 and with a fluid source 132 included in the pressure control mechanism 130 (e.g., via the catheter 150).

The pressure control mechanism 130 can have a variety of configurations. Generally, the pressure control mechanism 130 can be configured to regulate a pressure of fluid in the band 120 by controlling a flow of fluid between the band 120 and the fluid source 132. The pressure control mechanism 130 can include the fluid source 132 as illustrated in FIG. 1B, but the fluid source 132 can be a separate element included in the system 100 outside the pressure control mechanism 130. One exemplary embodiment of the pressure control mechanism 130 includes a fluid logic system configured to regulate a pressure of fluid in the band 120 in response to a fluid pressure acting thereon, such as a fluid logic system disclosed in more detail in commonly-owned U.S. application Ser. No. 11/965,334 entitled "Fluid Logic For Regulating Restriction Devices," filed on Dec. 27, 2007, which is hereby incorporated by reference in its entirety. Another exemplary embodiment of the pressure control mechanism 130 includes a transient pressure control mechanism configured to controllably release fluid from a fluid source (e.g., the fluid source 132) into the band 120 to help maintain a desirable pressure of fluid in the band 120, such as a transient pressure control mechanism disclosed in more detail in commonly-owned U.S. application Ser. No. 11/965,331 entitled "Controlling Pressure In Adjustable Restriction Devices," filed on Dec. 27, 2007, which is hereby incorporated by reference in its entirety. Still another embodiment of the pressure control mechanism 130 includes a substantially constant force mechanism configured to maintain a substantially constant pressure of fluid in the band 120 where an amount of fluid in the band 120 can correspond to an amount of restriction applied by the band 120, such as a substantially constant force mechanism disclosed in more detail in commonly-owned U.S. application Ser. No. 11/965,322 entitled "Constant Force Mechanisms For Regulating Restriction Devices," filed on Dec. 27, 2007, which is hereby incorporated by reference in its entirety. A person skilled in the art will appreciate that other pressure control mechanisms can be used as the pressure control mechanism 130 and that, as mentioned above, the fluid source 132 can be located external to the pressure control mechanism 130.

The fluid source 132 can also have various configurations, as discussed further below, and the restriction system 100 can include any number of fluid sources. For example, the fluid source 132 can include a pressured fluid reservoir in the form of a rigid or flexible housing coupled to the flow control mechanism 160 by a catheter (e.g., the catheter 150) or other connector. The pressured fluid reservoir can be a low pressure reservoir, a constant pressure reservoir, a high pressure reservoir, or various combinations thereof. The pressure can also change from low to high etc. Exemplary pressured fluid reservoirs are disclosed in more detail in previously mentioned U.S. application Ser. No. 11/965,334 entitled "Fluid Logic For Regulating Restriction Devices," filed on Dec. 27, 2007. As another example, the fluid source 132 can include the human body (e.g., the stomach, peritoneum, lung, saline generated through osmosis, intracellular fluids, blood, etc.). A catheter or other pathway can extend from the flow control mechanism 160 to a location in the body where it is desirable to obtain and/or release fluid. As yet another example, the fluid source 132 can include a pump system (e.g., a positive displacement pump and a centrifugal pump), such as those disclosed in more detail in previously mentioned U.S. application Ser. No. 11/965,331 entitled "Controlling Pressure In Adjustable Restriction Devices," filed on Dec. 27, 2007. As still another example, the fluid source 132 can include a constant force mechanism, such as those disclosed in more detail in previously mentioned U.S. application Ser. No. 11/965,322 entitled "Constant Force Mechanisms For Regulating Restriction Devices," filed on Dec. 27, 2007. The fluid source 132 can also or alternatively be included in the port 180 or in another, similar port. Additionally, if the fluid source 132 is not disposed in a port, it may or may not be in fluid communication with a port through a catheter or other connector to allow fluid to be introduced to and withdrawn from the fluid source 132.

In an exemplary embodiment, the fluid source 132 can include at least one pressured fluid reservoir contained within a housing. The pressure can be generated using various techniques known in the art, including various techniques disclosed herein and discussed in more detail below. The maximum amount of fluid contained in the housing can be a sufficient volume of fluid to fill the band 120 and any connecting elements disposed between the band 120 and the fluid source 132, e.g., the catheter 150, the flow control mechanism 160, the pressure control mechanism 130, etc. The pressure $P_1$ of fluid within the fluid source 132 can be configured to allow the pressure $P_2$ of fluid within the band 120 to be at or substantially near its maximum pressure level when the band 120 is dormant (e.g., when the patient is not eating or drinking). The pressure $P_1$ of fluid within the fluid source 132 can also be configured such that the pressure control mechanism 130 can allow fluid to flow from the band 120 toward the fluid source 132 when the band 120 is not dormant (e.g., when the patient is eating or drinking) because the pressure $P_2$ in the band 120 would exceed the pressure $P_1$ in the fluid source 132. Similarly, when forces (e.g., peristaltic pulses from swallowing) stop acting on the band 120, the pressure $P_2$ in the band 120 can be lower than the pressure $P_1$ in the fluid source 132, and the pressure control mechanism 130 can allow fluid to flow from the fluid source 132 toward the band 120. The pressure $P_1$ in the fluid source 132 can be fixed or adjustable.

The fluid source 132 can have a variety of shapes, sizes, and configurations. FIGS. 3A-3D show various embodiments of a pressured fluid source 132. In the illustrated embodiment of FIG. 3A, the fluid source 300 generally includes a housing 302 (e.g., a rigid volume) having an internal cavity divided into two chambers with an inverse relationship, namely a biasing chamber 304 configured to have a biasing element disposed therein and a fluid chamber 306 configured to contain fluid. The housing 302 can have a variety of shapes and sizes, but in the illustrated embodiment the housing 302 is substantially cylindrical. The chambers 304, 306 can be separated by a movable translating surface 308. In the illustrated embodiment, forces acting on the translating surface 308 can include a force $F_{fluid}$ in a direction toward the translating surface 308 and the housing's proximal end 309 caused by fluid in the fluid chamber 306 and a force $F_{bias}$ in a direction toward the translating surface 308 and the housing's distal end 311 caused by a biasing mechanism 310 coupled to the translating surface 308. As shown, the biasing mechanism 310 is configured to bias the translating surface 308 toward the housing's distal end 311 and is thus configured to form a pressured fluid source 300. Generally, biasing the biasing mechanism 310 in the opposite direction, toward the housing's proximal end 309, can bias the fluid source 300 as a high pressure reservoir. When the pressure in the band 120 changes, the translating surface 308 can move in response as the force $F_{fluid}$ in the fluid chamber 306 correspondingly changes. For example, when the pressure $P_2$ of fluid in the band 120 decreases, e.g., following eating, in response to any physiologic condition of the patient's anatomy, etc., the biasing force $F_{bias}$ of the biasing mechanism 310 will be greater than a force applied to the fluid chamber 306 by the fluid in the band 120, and thus the translating surface 308 will move toward the housing's distal end 311 (e.g., increase the size of the biasing chamber 304 and decrease the size of the fluid chamber 306). This will allow fluid to flow from the fluid source 300 toward the band 120, thus increasing the pressure $P_2$ of fluid in the band 120. As the pressure $P_2$ increases, the force applied to the fluid chamber 306 by the fluid in the band 120 will overcome the biasing force $F_{bias}$ to move the translating surface 308 back toward the closed position.

Figure 3A:
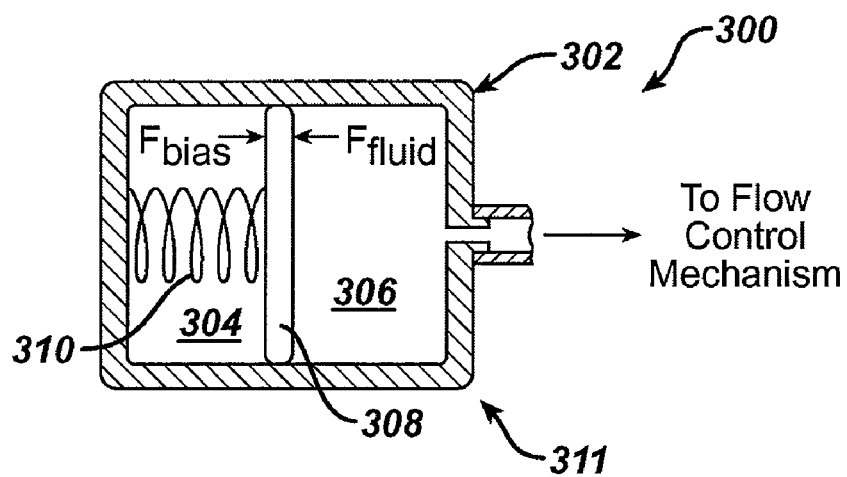
FIG. 3A is a schematic diagram of one embodiment of a fluid source that can be used in the food intake restriction system of FIG. 1B.
Figure 3B:
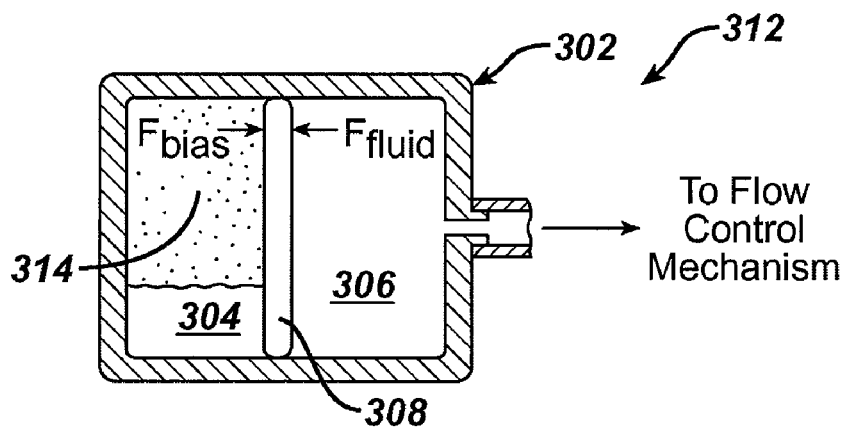
FIG. 3B is a schematic diagram of another embodiment of a fluid source that can be used in the food intake restriction system of FIG. 1B.
Figure 3C:
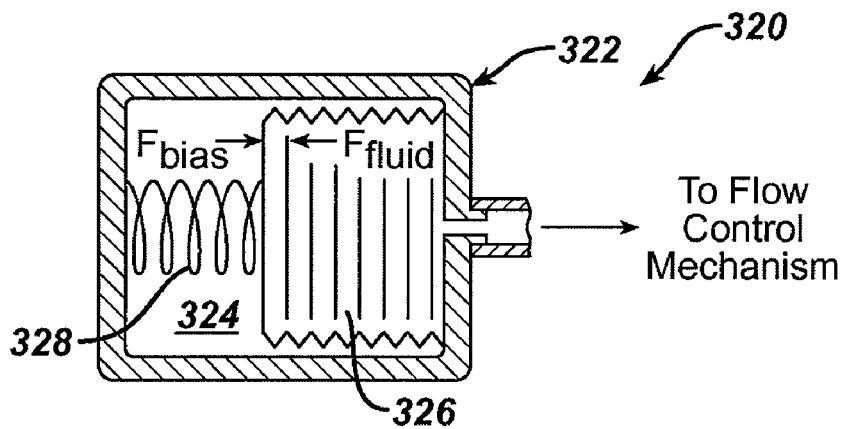
FIG. 3C is a schematic diagram of still another embodiment of a fluid source that can be used in the food intake restriction system of FIG. 1B.

The biasing mechanism 310 can include any number of components configured to bias the translating surface 308, but in the illustrated embodiment the biasing mechanism 310 is a spring coupled to an inside surface of the housing 302 at one end of the spring and to the translating surface 308 at a second end of the spring. The translating surface 308 can have various configurations that allow the force $F_{fluid}$ created by the fluid within the fluid chamber 306 to be transferred to the biasing mechanism 310. Additionally, the biasing mechanism 310 can be removable and/or adjustable to change the amount of force $F_{bias}$ acting on the fluid. When the biasing mechanism 310 is a spring, the pressure limit of the fluid source 132 can be changed by changing the type of spring that is used, which can at least change the spring constant, and/or by changing the length of the spring that is used. FIG. 3B illustrates another embodiment of a fluid source 312 where instead of the biasing mechanism in the biasing chamber 304 being a spring, the biasing mechanism includes a fluid 314 in thermodynamic saturation.

Figure 3D:
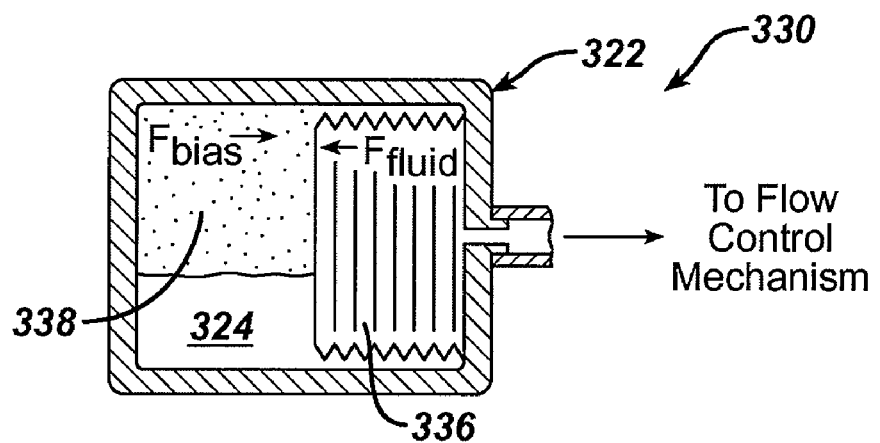
FIG. 3D is a schematic diagram of yet another embodiment of a fluid source that can be used in the food intake restriction system of FIG. 1B.

The fluid chamber 306 can include any number of components configured to contain a fluid and bias the translating surface 308. In the embodiments shown in FIGS. 3A and 3B, fluid is freely disposed within the fluid chamber 306 (e.g., contained within inner surfaces of the housing 302). In another embodiment shown in FIG. 3C, a fluid source 320 is similar to the fluid source 300 of FIG. 3A, but the fluid source 320 of FIG. 3C includes a housing 322 having a single-chambered internal cavity 324 (and thus no translating surface separating chambers). The internal cavity 324 includes an expandable bladder, e.g., a bellows 326, and a biasing mechanism 328 disposed therein. The bellows 326 is configured to contain fluid and to be in fluid communication with other elements included in the restriction system 100 (e.g., the flow control mechanism 160, the band 120, etc.). The biasing mechanism 328 is a spring in this embodiment coupled to an inside surface of the housing 322 at one end of the spring and to an outside surface of the bellows 326 at a second end of the spring. FIG. 3D illustrates another embodiment of a fluid source 330 that, similar to the fluid source 320 of FIG. 3C, includes the housing 322 having the single-chambered internal cavity 324 with an expandable bladder, e.g., a bellows 336, disposed therein. Similar to the fluid source 312 of FIG. 3B, the fluid source 330 also includes a fluid 338 in thermodynamic solution disposed within the housing 322 that acts as a biasing mechanism.

The flow control mechanism 160 of FIG. 1B can also have a variety of configurations. Generally, the control housing 170 includes a fluid communication member (e.g., a flexible tube) having a fluid pathway with a geometry that defines the flow rate of fluid through the control housing 170 and hence a flow rate between the band 120 and the fluid source 132. The geometry of the control housing's fluid pathway can be adjusted between a plurality of fixed positions, as discussed further below, thereby allowing for fixed but adjustable flow rates between the band 120 and the fluid source 132.

The flow control mechanism 160 (e.g., the control housing 170 and optionally the port 180) can have any configuration, size, and shape and can be made from any type of and any combination of materials, preferably biocompatible materials appropriate for use in a body, such as a polymer, a biocompatible metal (e.g., stainless steel and titanium), and other similar types of materials. The control housing 170 can be rigid or flexible and can be made from any combination of rigid and flexible materials, but, as discussed further below, the control housing 170 preferably has rigid top and bottom surfaces and a rigid perimeter wall, while the fluid communication member disposed within the control housing 170 is preferably flexible. The control housing 170 can have any shape. The control housing 170 can further include two or more catheter tube connection members in fluid communication with various elements included in the system 100 (e.g., the band 120, the pressure control mechanism 130, and the port 180) and configured to couple to a catheter (e.g., the catheter 150) or other connector.

The control housing 170 can optionally be coupled with a regulation mechanism, e.g., the port 180, that can be used to adjust the diameter of the fluid communication member within the control housing 170, as described further below. The control housing 170 and the port 180 are separate elements in fluid communication via the catheter 150, but in some embodiments, the control housing 170 and the port 180 can be included in a single housing. The port 180 can be configured to allow fluid to be introduced into and removed from one or more elements included in the restriction system 100, which in this example includes the control housing 170. The port 180 can thus be implanted at a location within the body that is accessible through the tissue. Typically, injection ports are positioned in the lateral subcostal region of the patient's abdomen under the skin and layers of fatty tissue. Surgeons also typically implant injection ports on the sternum of the patient. Generally, as fluid is introduced and removed through the port 180, fluid can be, respectively, introduced into and removed from the control housing 170, thereby adjusting the diameter of the fluid communication member within the control housing 170.

Figure 4:
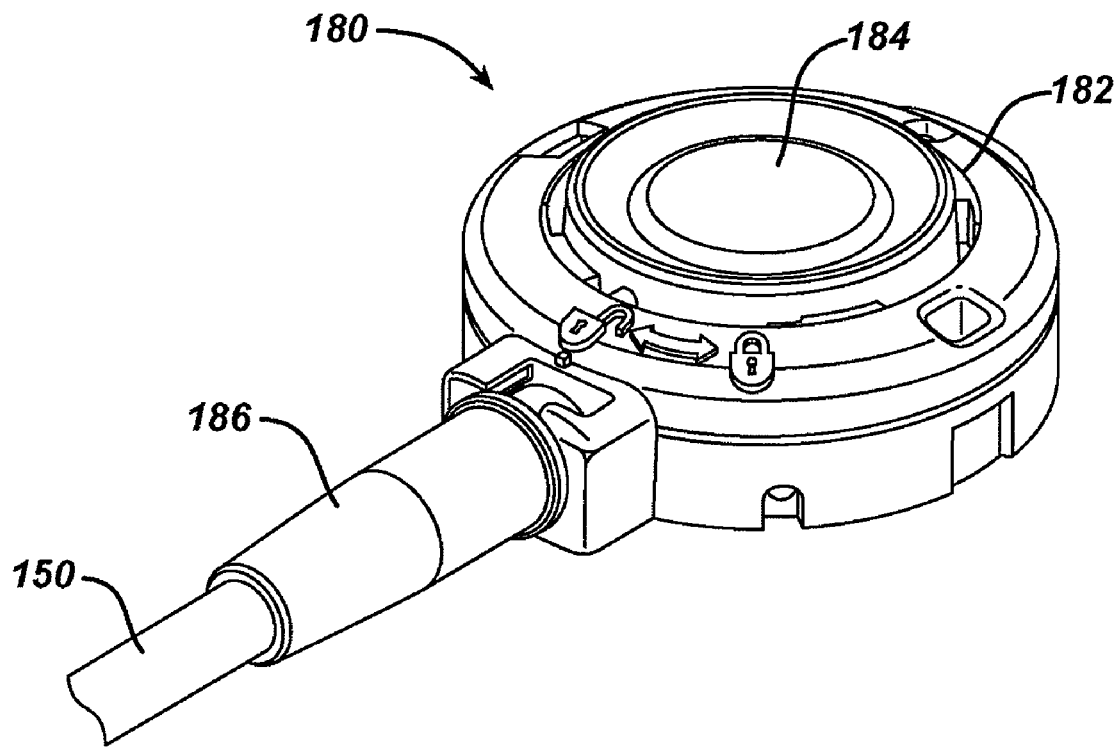
FIG. 4 is a perspective view of one embodiment of an injection port housing of the food intake restriction system of FIG. 1B.

The port 180 can also have a variety of configurations, and it can optionally be provided in the system 100 to allow fluid or other materials to be introduced into various components of the system 100, such as the band 120, the flow control mechanism 160, and/or one or more fluid sources. In one embodiment shown in FIG. 4, the port 180 has a generally cylindrical housing with a distal or bottom surface and a perimeter wall extending proximally from the bottom surface and defining a proximal opening 182. The proximal opening 182 can include a needle-penetrable septum 184 extending there across and providing access to a fluid source or reservoir (not visible in FIG. 4) formed within the port's housing. The septum 184 is preferably placed in a proximal enough position such that the depth of the reservoir is sufficient enough to expose the open tip of a needle, such as a Huber needle, so that fluid transfer can take place. The septum 184 is preferably arranged so that it will self seal after being punctured by a needle and the needle is withdrawn. As further shown in FIG. 4, the port 180 can further include a catheter tube connection member 186 in fluid communication with the reservoir and configured to couple to a catheter (e.g., the catheter 150). A person skilled in the art will appreciate that the port's housing can be made from any number of materials, preferably biocompatible materials such as stainless steel, titanium, or polymeric materials, and the septum 184 can likewise be made from any number of materials, preferably biocompatible materials, including silicone.

Figure 5:
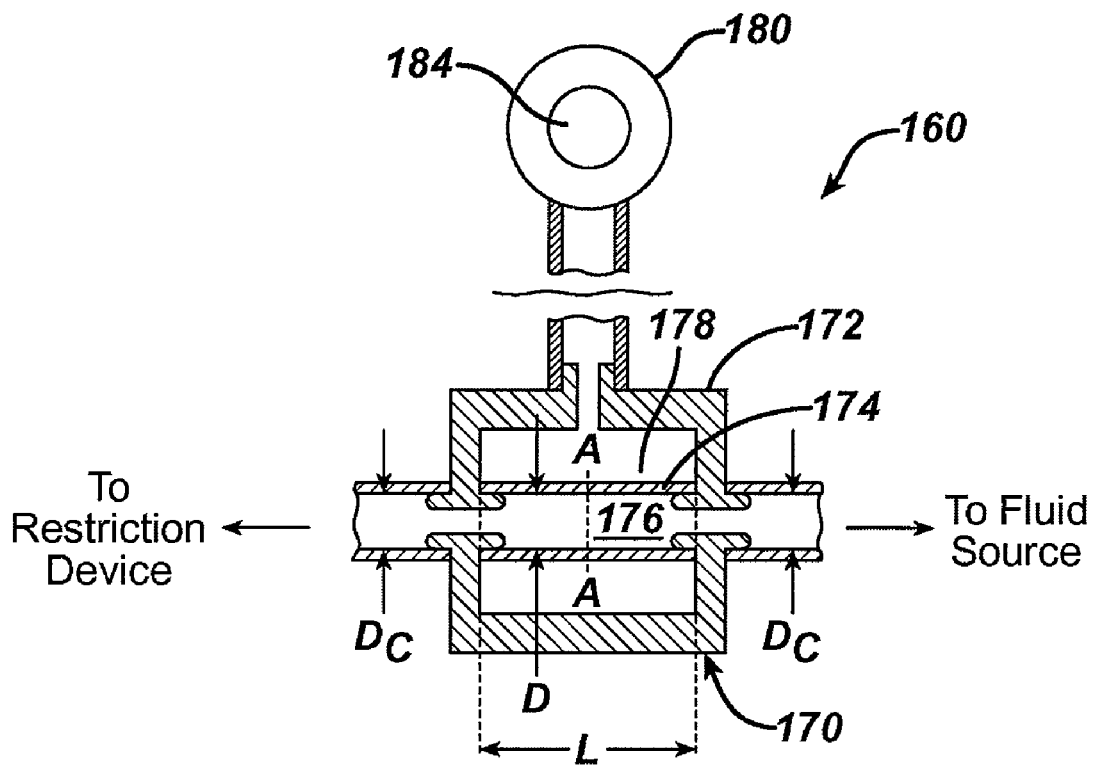
FIG. 5 is a schematic diagram of one embodiment of a flow control mechanism that can be used in the food intake restriction system of FIG. 1A.

As indicated above, the control housing 170 can have a variety of configurations, but FIG. 5 illustrates one exemplary embodiment of a flow control housing 170 having a body 172 with an internal cavity 178 having a fluid conduit 174 disposed therein. The illustrated fluid conduit 174 is in the form of an elongate tubular body having an inner pathway 176 extending longitudinally therethrough through which fluid can flow, but the fluid conduit 174 can have any configuration. Furthermore, the fluid conduit 174 can have any size and shape and can be made of any (preferably biocompatible) material(s), but it is preferably made from a flexible material to allow for adjustment of its geometry, such as its size, e.g., volume or diameter, and/or shape.

Figure 6:
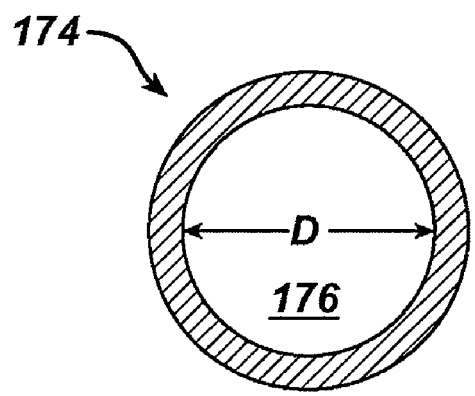
FIG. 6 is a cross-sectional view of a fluid communication member of the flow control mechanism of FIG. 5.

Generally, the fluid conduit 174 is configured to be in fluid communication with the band 120 and the fluid source 132 and to have a diameter D adjustable between two or more fixed positions. The diameter D in this embodiment defines an inner diameter of the fluid conduit 174, as illustrated in FIG. 6. The cross-section of the fluid conduit 174 is shown as substantially circular, but the fluid conduit 174 can have any cross-sectional shape, e.g., elliptical, rectangular, square, "D"-shaped, etc. The shape of the fluid conduit 174 determines the rate of fluid flow through the control housing 170, with a larger diameter D corresponding to faster flow rates (e.g., a higher fluid volume flow per second) and a smaller diameter D corresponding to slower flow rates (e.g., a lower fluid volume flow per second). In other words, adjusting the diameter D of the fluid conduit 174 can increase or decrease the size (e.g., volume) of the inner pathway 176 and hence increase or decrease a volume of fluid that can flow through the control housing 170 in a period of time. The flow rate (Q) through the fluid conduit 174 can be generally expressed as follows, where L equals the fluid conduit's longitudinal length, $P_1$ equals the pressure of fluid in the fluid source 132, and $P_2$ equals the pressure of fluid in the band 120:

$$Q \propto \frac{D}{L}(P_1 - P_2)$$

The diameter D can vary along the length L of the fluid conduit 174, as discussed further below, but as illustrated in FIG. 5, the fluid conduit 174 is in an equilibrium position where the diameter D is substantially constant along the fluid conduit's length L. In other words, in the equilibrium position, the diameter D of the fluid conduit 174 substantially equals the diameter $D_C$ of the catheter 150 coupling the flow control mechanism 160 with the band 120 and with the fluid source 132 such that, in use, the flow control mechanism 160 effectively acts as part of the catheter 150 and does not substantially increase or decrease a rate of fluid flow through the control housing 170 as compared to a rate of fluid flow through the catheter 150 coupling the flow control mechanism 160 with the band 120 and with the fluid source 132. In this case, the catheter's diameter $D_C$ is the catheter's inner diameter to appropriately correspond to the fluid conduit's diameter D.

The fluid conduit's diameter D can be adjusted in a variety of ways, but in certain exemplary embodiments, the size of the diameter D can be adjusted by introducing fluid into and removing fluid from the internal cavity 178 of the body 172. In other words, the fluid conduit 174 disposed within the internal cavity 178 can be allowed more or less expansion space within the internal cavity 178 depending on an amount of fluid disposed within the internal cavity 178 (external to the fluid conduit 174). Whether the body 172 is made from a rigid or a flexible material, the internal cavity 178 can have an internal area that can hold a finite amount of fluid (e.g., air, water, saline, etc.). When fluid is added to the internal cavity 178, the fluid conduit 174 can be constricted (e.g., the diameter D can decrease to decrease the volume of the inner pathway 176) to accommodate the additional fluid in the internal cavity 178. Correspondingly, when fluid is removed from the internal cavity 178, the fluid conduit can expand (e.g., the diameter D can increase to increase the volume of the inner pathway 176) given the newly freed space in the internal cavity 178. For example, the fluid cavity 178 can be in fluid communication with the port 180 (e.g., with a fluid reservoir included in the port 180). When an amount of fluid is introduced into or withdrawn from the flow control mechanism 160 through the port 180, a corresponding amount of fluid is introduced into or withdrawn from the internal cavity 178. Because the internal cavity 178 has a finite volume in which to accommodate fluid disposed therein and the fluid conduit 174 also disposed within the internal cavity 178, maintaining a constant amount of fluid in the internal cavity 178 allows the fluid conduit 174 to have a fixed position having a maximum diameter. The fluid conduit 174 can remain in the fixed position at least until (and if) the amount of fluid in the internal cavity 178 changes, when the fluid conduit 174 can change to another fixed position having a different maximum diameter D. The fluid conduit 174 can increase from any diameter to any increased diameter and decrease from any diameter to any decreased diameter.

Figure 7:
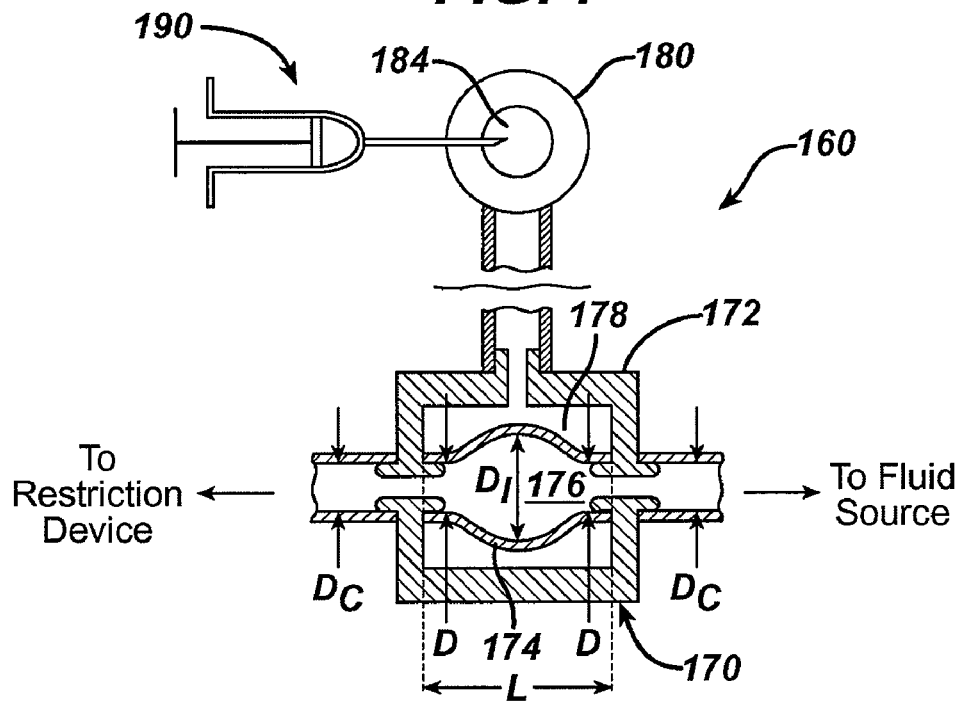
FIG. 7 is a schematic diagram of the flow control mechanism of FIG. 5 having a fluid communication member with an increased diameter.

As shown in one embodiment of an increased fluid conduit diameter in FIG. 7, fluid can be removed from the flow control mechanism 160 through the port 180 using a syringe 190, e.g., a Huber needle inserted through the port's septum 184, thereby reducing an amount of fluid in the control housing's internal cavity 178. With a reduction in the amount of fluid in the internal cavity 178, the fluid conduit 174 can increase from the equilibrium position having the diameter D to a second position having an increased diameter $D_I$, where $D_I$ is greater than D. As shown in FIG. 7, the increased diameter $D_I$ of the fluid conduit 174 is not constant along the length L of the fluid conduit 174 (although the increased diameter $D_I$ could be constant along the length L in some embodiments). Rather, the diameter D of the fluid conduit 174 increases to the increased diameter $D_I$ at least in a mid-portion of the fluid conduit 174 and remains substantially at the equilibrium diameter D at the fluid conduit's proximal and distal ends where the fluid conduit 174 couples with the body 172 so as to be in fluid communication with the catheter 150. The effect remains that decreasing an amount of fluid in the internal cavity 178 increases the fluid conduit's diameter and increases a volume of the inner pathway 176 through which fluid can flow between the band 120 and the fluid source 132.

Figure 8:
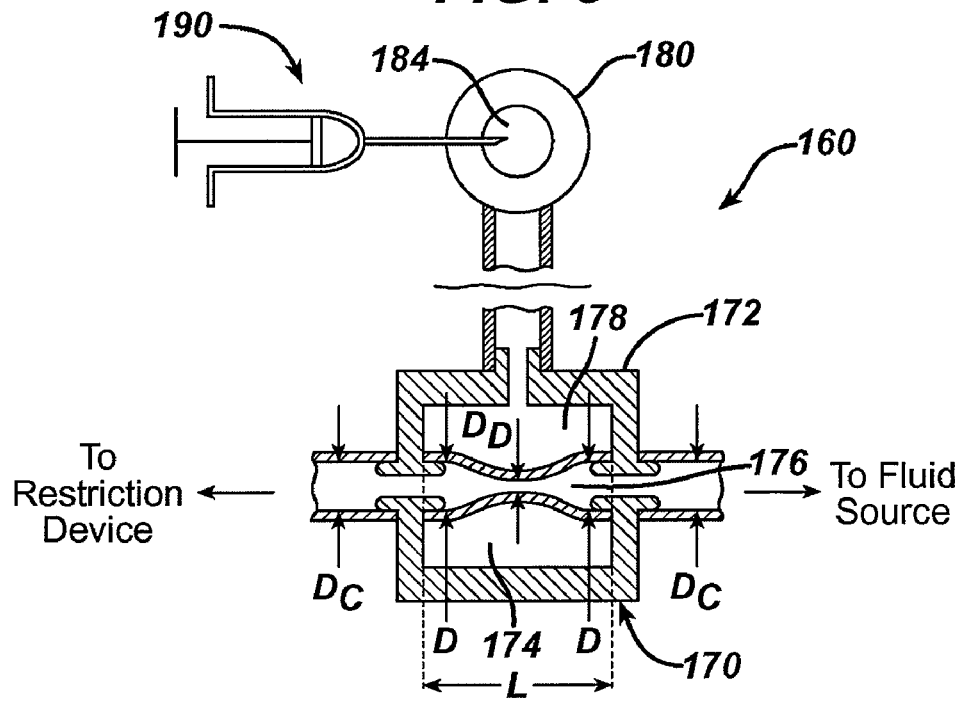
FIG. 8 is a schematic diagram of the flow control mechanism of FIG. 5 having a fluid communication member with a decreased diameter.

Similarly, as shown in one embodiment of a decreased fluid conduit diameter in FIG. 8, fluid can be introduced to the flow control mechanism 160 through the port 180 using the syringe 190, thereby increasing an amount of fluid in the control housing's internal cavity 178. With an increase in the amount of fluid in the internal cavity 178, the fluid conduit 174 can reduce from the equilibrium position having the diameter D to a second position having a decreased diameter $D_D$, where $D_D$ is less than D. As shown in FIG. 8, the decreased diameter $D_D$ of the fluid conduit 174 is not constant along the length L of the fluid conduit 174 (although the decreased diameter $D_D$ could be constant along the length L in some embodiments). Rather, the diameter D of the fluid conduit 174 decreases to a minimum diameter $D_D$ at least in a mid-portion of the fluid conduit 174 and remains substantially at the equilibrium diameter D at the fluid conduit's proximal and distal ends. The effect remains that increasing an amount of fluid in the internal cavity 178 decreases the fluid conduit's diameter and decreases a volume of the inner pathway 176 through which fluid can flow between the band 120 and the fluid source 132.

Because the body 172 is rigid in this embodiment, as shown in FIGS. 7 and 8, the body 172 does not change size or shape with removal of fluid from or introduction of fluid to the internal cavity 178, nor does the length L of the fluid conduit 174 change.

The diameter D of the fluid conduit 174 can vary even in a fixed position dependent on, for example, an amount of fluid flowing through the inner pathway 176. For example, the fluid conduit 174 can at least partially collapse to a smaller diameter at least in its mid-portion if little or no fluid is flowing through the flow control mechanism 160, e.g., because not enough fluid is flowing through the inner pathway 176 to allow the inner pathway 176 to expand to its maximum volume because substantially all fluid in the system's closed fluid circuit is in the band 120. However, the fluid conduit 174 still has a fixed position that cannot vary, e.g., the fluid conduit 174 cannot increase its volume beyond what is allowed in the internal cavity 178 by the amount of fluid disposed outside the fluid conduit 174 in the internal cavity 178.

While the syringe 190 is described as being manually operable to adjust an amount of fluid in the internal cavity 178 through the port 180, fluid need not actually transfer between the internal cavity 178 (or any part of the control housing 170) and the syringe 190. In other words, the amount of fluid in the internal cavity 178 can be adjusted by the mere shifting of fluid between the internal cavity 178 and the syringe 190 (e.g., by introducing fluid to or removing fluid from the fluid source or reservoir included in the port 180, which displaces fluid previously in the internal cavity 178 or displaces fluid into the internal cavity 178), as such shifting will cause similar shifting of fluid "upstream" of the internal cavity 178. It is not necessary for fluid being introduced into or removed from the internal cavity 178 through the port 180 to have actually come from or be withdrawn into the syringe 190 (or even from or into the port 180 because fluid can be displaced from within the catheter 150, or any other connectors, between the port 180 and the control housing 170). Furthermore, flow of any fluid discussed herein can include similar fluid shifting between two or more elements.

As discussed above, the flow control mechanism 160 can have various configurations, and the system 100 can include any number of fluid sources. For example, an amount of fluid in the control housing's internal cavity 178 can be adjusted directly through the control housing 170 rather than through the port 180 if, for example, the control housing 170 includes a septum (such as one similar to the septum 184) configured to allow fluid introduction to and fluid withdrawal from the internal cavity 178.

Any amount of fluid can be introduced into or withdrawn from the flow control mechanism 160 through the port 180 any number of times and at any frequency. The amount of fluid introduced into and/or withdrawn from the flow control mechanism 160, the number of times fluid is introduced into and/or withdrawn from the flow control mechanism 160, and the frequency of fluid adjustments can vary by patient and are preferably determined by the patient's physician (or other medical personnel) as part of a patient's treatment plan. Furthermore, the system 100 can be implanted in a patient with a particular amount of fluid in the flow control mechanism 160 (including no fluid in the flow control mechanism 160). Subsequent to implantation, the flow control mechanism 160 can be filled with an amount of fluid, such as by introducing fluid into the port 180 using the syringe 190.

Figure 9:
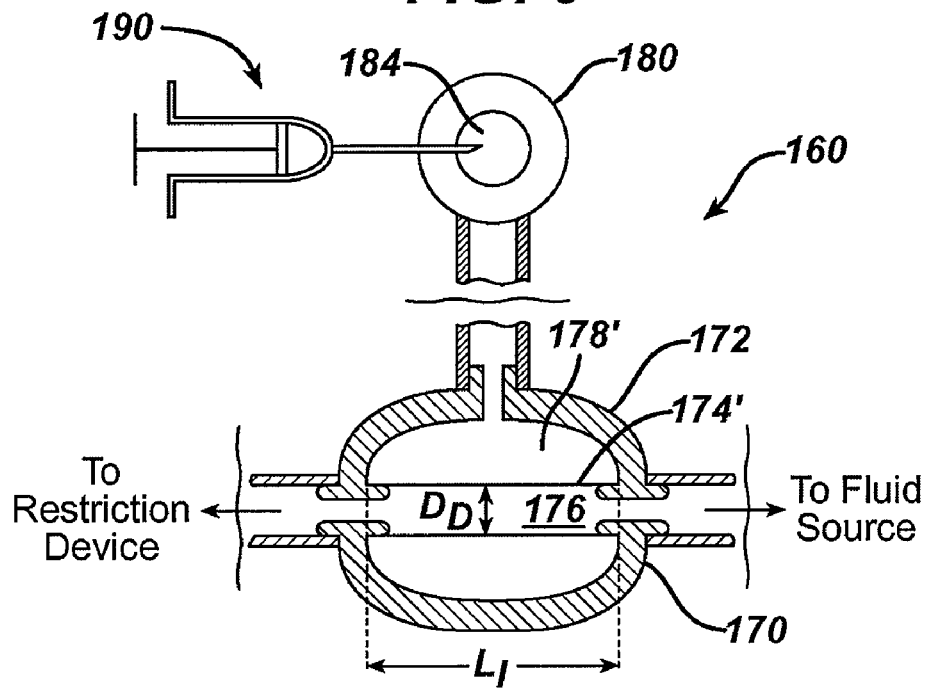
FIG. 9 is a schematic diagram of the flow control mechanism of FIG. 5 having a fluid communication member with a decreased diameter and an increased length.
Figure 10:
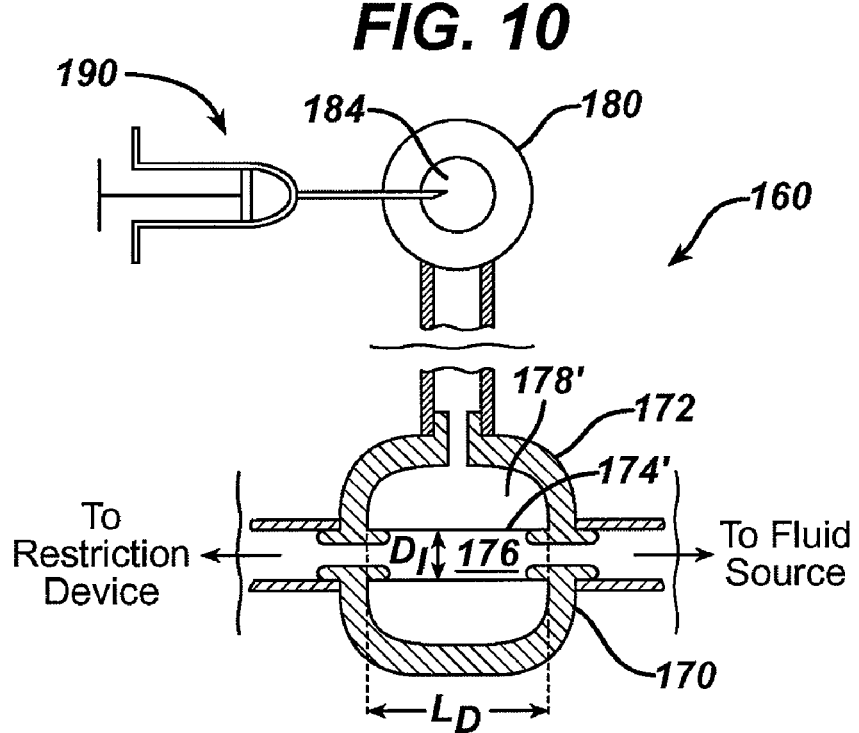
FIG. 10 is a schematic diagram of the flow control mechanism of FIG. 5 having a fluid communication member with an increased diameter and a decreased length.

While not shown, in another embodiment, the fluid conduit 174 can include a microcapillary, e.g., a capillary tube. The microcapillary can change its diameter D and its length L when fluid is added to or withdrawn from the internal cavity 178 (e.g., as described above using the port 180). In this embodiment, the body 172 is preferably flexible or at least partially flexible to allow the microcapillary to expand and contract in length. For example, as shown in one embodiment of a decreased fluid conduit diameter in FIG. 9, fluid can be introduced to the flow control mechanism 160 through the port 180 using the syringe 190, thereby increasing an amount of fluid in the control housing's internal cavity 178'. With an increase in the amount of fluid in the internal cavity 178', a fluid conduit 174' can reduce from the equilibrium position having the diameter D to a second position having a decreased diameter $D_D$ constant along the length $L_I$ of the microcapillary 174', where $L_I$ is greater than L. Similarly, in another example shown in FIG. 10, fluid can be withdrawn from the flow control mechanism 160 through the port 180 using the syringe 190, thereby decreasing an amount of fluid in the control housing's internal cavity 178'. With a decrease in the amount of fluid in the internal cavity 178', the fluid conduit 174' can increase from the equilibrium position having the diameter D to a second position having an increased diameter $D_I$ constant along the length $L_D$ of the microcapillary 174', where $L_D$ is less than L.

Figure 11:
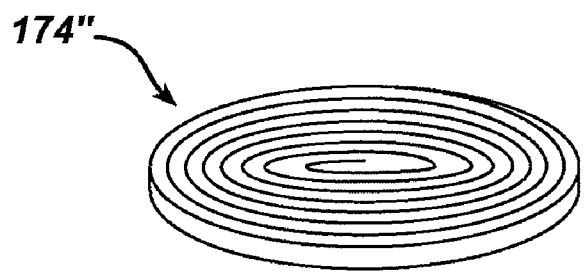
FIG. 11 is a cross-sectional view of an alternate embodiment of a fluid communication member that can be included in the flow control mechanism of FIG. 5.

In some embodiments, the microcapillary 174' can have a spiraled A-A cross-section as shown in a variation of a microcapillary 174" in FIG. 11. The microcapillary 174" can have such a spiraled cross-section along its entire length L or along any one or more portions of its length L. Such a spiraled cross-section can allow the microcapillary 174" to increase and decrease its length L as fluid is, respectively, introduced into and withdrawn from the internal cavity 178'. In other words, the microcapillary 174" can act as an expansion cone.

Preferably, the microcapillary's distal and proximal portions are each spiral-shaped such that the distal and proximal portions can expand and contract to change the length L of the microcapillary 174".

In another embodiment of a flow control mechanism 160', a diameter of the flow control mechanism 160' can be adjustably controlled through linear motion. As shown in one embodiment in FIG. 12, the flow control mechanism 160' includes a fluid pathway 200 in fluid communication with the band 120 and the fluid source 132. The fluid pathway 200 has a maximum diameter or thickness $t_{max}$ along the fluid pathway's longitudinal length L2. The maximum thickness $t_{max}$ of the fluid pathway 200 can be adjustable along at least a portion of its longitudinal length L2. In this illustrated example, a portion less than the fluid pathway's longitudinal length L2 has an adjustable diameter or thickness t. As the adjustable thickness t of the fluid pathway 200 changes, the flow rate through the flow control mechanism 160 changes and can generally be expressed as $$Q \propto t(P_1 - P_2)$$

where the flow rate (Q) is maximized when the adjustable thickness t equals the maximum thickness $t_{max}$.

The adjustable thickness t can be adjusted between two or more fixed positions in a variety of ways. For example, a length l of an obstruction mechanism 202 extending into the fluid pathway 200 can define the adjustable thickness t of the fluid pathway 200. The length l can have any value (including zero, in which case the adjustable thickness t is at its maximum value $t_{max}$ without any obstruction in the fluid pathway 200 being provided by the obstruction mechanism 202). Generally, the flow rate and the adjustable thickness t have a linear relationship such that increasing the length l decreases the diameter of and the flow rate through the fluid pathway 200, while decreasing the length l increases the diameter of and the flow rate through the fluid pathway 200.

Figure 12:
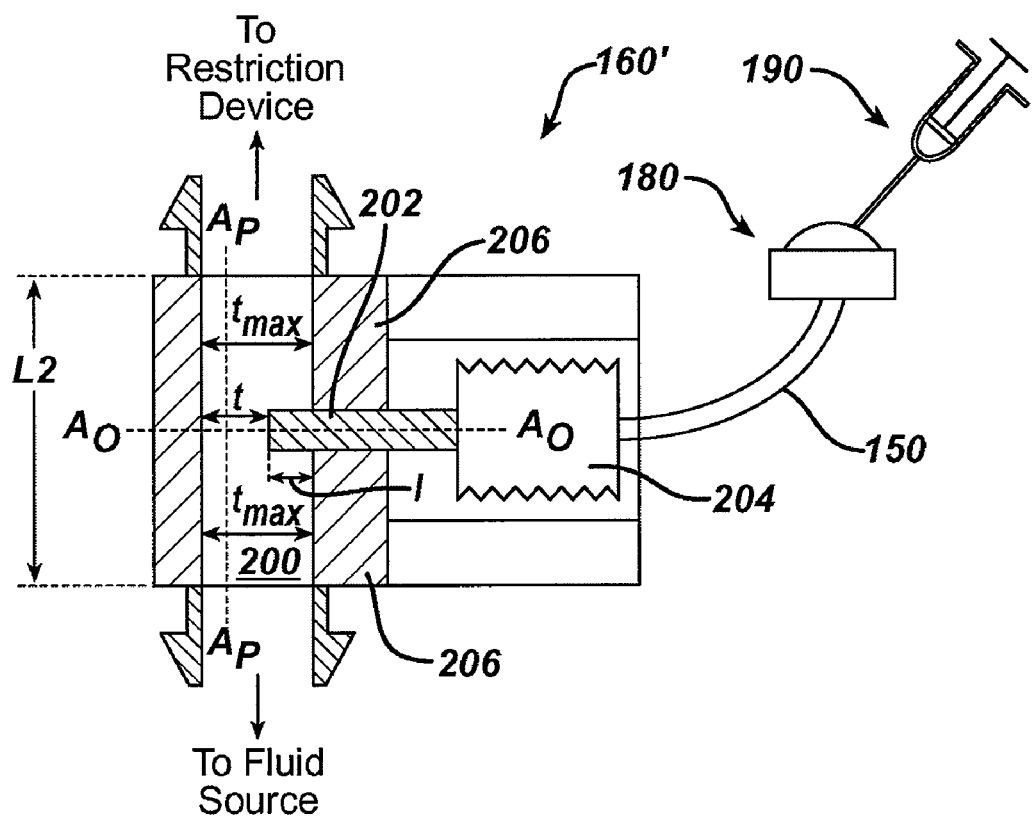
FIG. 12 is a schematic diagram of another embodiment of a flow control mechanism that can be used in the food intake restriction system of FIG. 1A.

As further show in FIG. 12, an adjustment mechanism 204 can be coupled to the obstruction mechanism 202, and it can be configured to change the length l of the obstruction mechanism 202 that extends into the fluid pathway 200. The adjustment mechanism 204 can have a variety of configurations, but in the illustrated embodiment of FIG. 12, the adjustment mechanism 204 is in the form of a fluid-filled bladder, e.g., a compressible bellows. The adjustment mechanism 204 can be fluidly coupled to the port 180 via the catheter 150 (or any other connector) to allow fluid to be introduced into and removed from the adjustment mechanism 204 via the port 180 (e.g., using the syringe 190) to assist in changing the length l of the obstruction mechanism 202 in the fluid pathway 200. By way of another non-limiting example, another adjustment mechanism 204 that can be used is a screw coupled to the obstruction mechanism 202. Rotation of the screw can be effective to increase and/or decrease a force applied by the screw to the obstruction mechanism 202, which in turn changes the length l of the obstruction mechanism 202 in the fluid pathway 200. By way of a further non-limiting example, another adjustment mechanism that can be used is a piston cylinder that can actuate the obstruction mechanism 202.

A person skilled in the art will also appreciate that the adjustment mechanism 204 can have particular characteristics that can be adjusted to change the length l of the obstruction mechanism 202 in the fluid pathway 200. For example, in embodiments where the adjustment mechanism 204 includes a spring, a spring constant or a length of the spring can be adjusted to change the length l of the obstruction mechanism 202 in the fluid pathway 200. The spring can be any flexible elastic object having any shape. For example, the spring can be a coil or helical spring having a cylindrical shape, although the spring can have other shapes, such as conical or dual conical, and it can have individual coils of any shape, such as elliptical or rectangular. Other examples of the adjustment mechanism 204 include an elastic band, thread, or cord, a volute spring, and other similar types of flexible elastic objects. The spring can also have a variety of sizes, and, if more than one spring is used, different springs used for the adjustment mechanism 204 can have different sizes and shapes. Furthermore, if more than one spring or other biasing mechanism is used anywhere within the restriction system 100 (or other restriction system), each spring can be the same as or different from any other spring within the restriction system 100.

The obstruction mechanism 202 can have a variety of sizes, shapes, and configurations. Generally, a longitudinal axis $A_O$ of the obstruction mechanism 202 extends substantially perpendicular to a longitudinal axis $A_P$ of the fluid pathway 200 such that movement of the obstruction mechanism 202 substantially parallel to its axis $A_O$ changes the length l of the obstruction mechanism 202 in the fluid pathway 200. In the embodiment shown in FIG. 12, the obstruction mechanism 202 is a substantially cylindrical, smooth, linear, rigid rod at least partially surrounded by a substantially fluid-impermeable bushing 206. However, the obstruction mechanism 202 can have any size, shape, and configuration that allows for its coupling with the adjustment mechanism 204. As the adjustment mechanism 204 expands (e.g., due to introduction of fluid into the adjustment mechanism 204 via introduction of fluid into the port 180), the obstruction mechanism 202 as a rigid member at least partially surrounded by the bushing 206 does not flex or bend but moves into the fluid pathway 200, thereby increasing the length l of the obstruction mechanism 202 in the fluid pathway 200. Similarly, as the adjustment mechanism 204 contracts (e.g., due to removal of fluid from the adjustment mechanism 204 via withdrawal of fluid from the port 180), the obstruction mechanism 202 also at least partially moves out of the fluid pathway 200, thereby decreasing the length l of the obstruction mechanism 202 in the fluid pathway 200.

Another embodiment of the obstruction mechanism is shown in FIG. 13. In this embodiment, the obstruction mechanism includes a threaded rod 208 at least partially surrounded by a substantially fluid-impermeable bushing 210 that includes threads 212 configured to engage the threaded rod 208. An adjustment mechanism such as one described above (e.g., a bellows, a piston cylinder, etc.) can be used to rotationally actuate the threaded rod 208, thereby adjusting the thickness t and thus also the flow rate through the pathway 200.

In yet another embodiment of a flow control mechanism 160", a flow rate between the band 120 and the fluid source 132 can be controlled by regulating a flow of fluid through a porous membrane. As shown in FIG. 14, the flow control mechanism 160" includes a porous disc or a semi-permeable membrane 220 disposed in a membrane housing 222. The membrane housing 222 has proximal and distal ends 224, 226 fluidly coupled, respectively, to the band 120 and the fluid source 132. The membrane 220 is disposed between the proximal and distal ends 224, 226 in a mid-portion 228 of the membrane housing 222. The membrane 220 can be adapted to allow fluid to flow into and out of the membrane housing 222 while sealing any fluid contained in the membrane housing 222 from the outside environment. In one exemplary embodiment, the membrane 220 is made of cellulose acetate. The flow rate (Q) through the membrane housing 222 can be generally expressed as follows, where w represents an average width, diameter, or thickness of the membrane 220 and d represents a pore size of the membrane's pores through which fluid can flow:

$$Q \propto \frac{(P_1 - P_2)d}{w}$$

The pore size d and the average width w can each have any value. The pore size d is preferably substantially constant for a given membrane 220. The average width w can be adjusted, thereby adjusting the flow rate through the flow control mechanism 160".

The average width w of the membrane 220 can be adjusted in a variety of ways. One way that the average width w can be adjusted is by disposing the membrane housing 222 in a flow control housing (e.g., the flow control housing 170 discussed above) as illustrated in an embodiment in FIG. 15. An amount of fluid also disposed within the flow control housing 170 can be adjusted (e.g., by using the port 180 and the syringe 190 as discussed above), thereby allowing compression and expansion of the membrane housing 222 and thus also the width w of the membrane 220 disposed therein. Generally, more fluid in the flow control housing 170 corresponds to a smaller width w and a faster flow rate, while less fluid in the flow control housing 170 corresponds to a larger width w and a slower flow rate.

Figure 16:
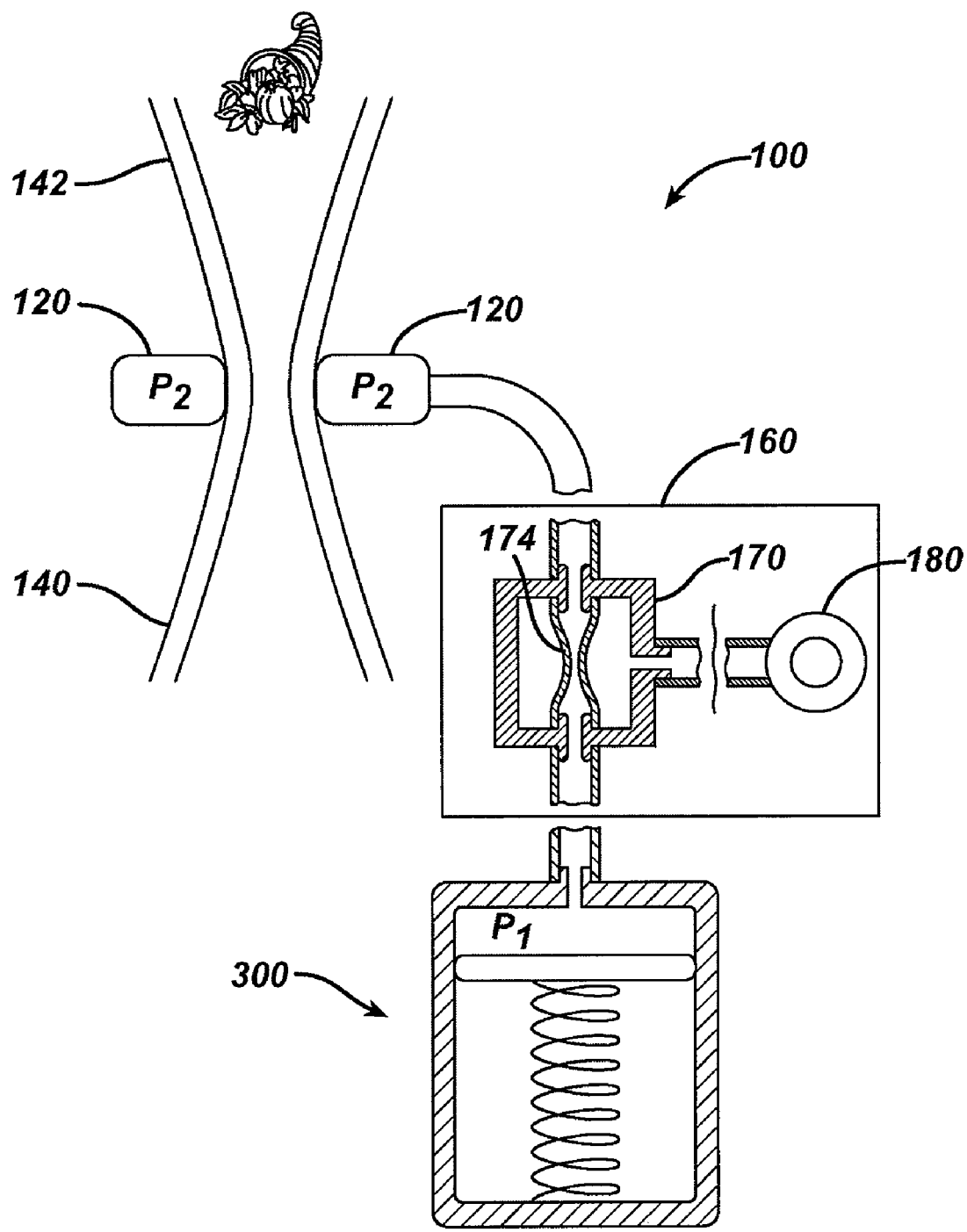
FIG. 16 is a schematic diagram of a food intake restriction system in use in a dormant stage.
Figure 17:
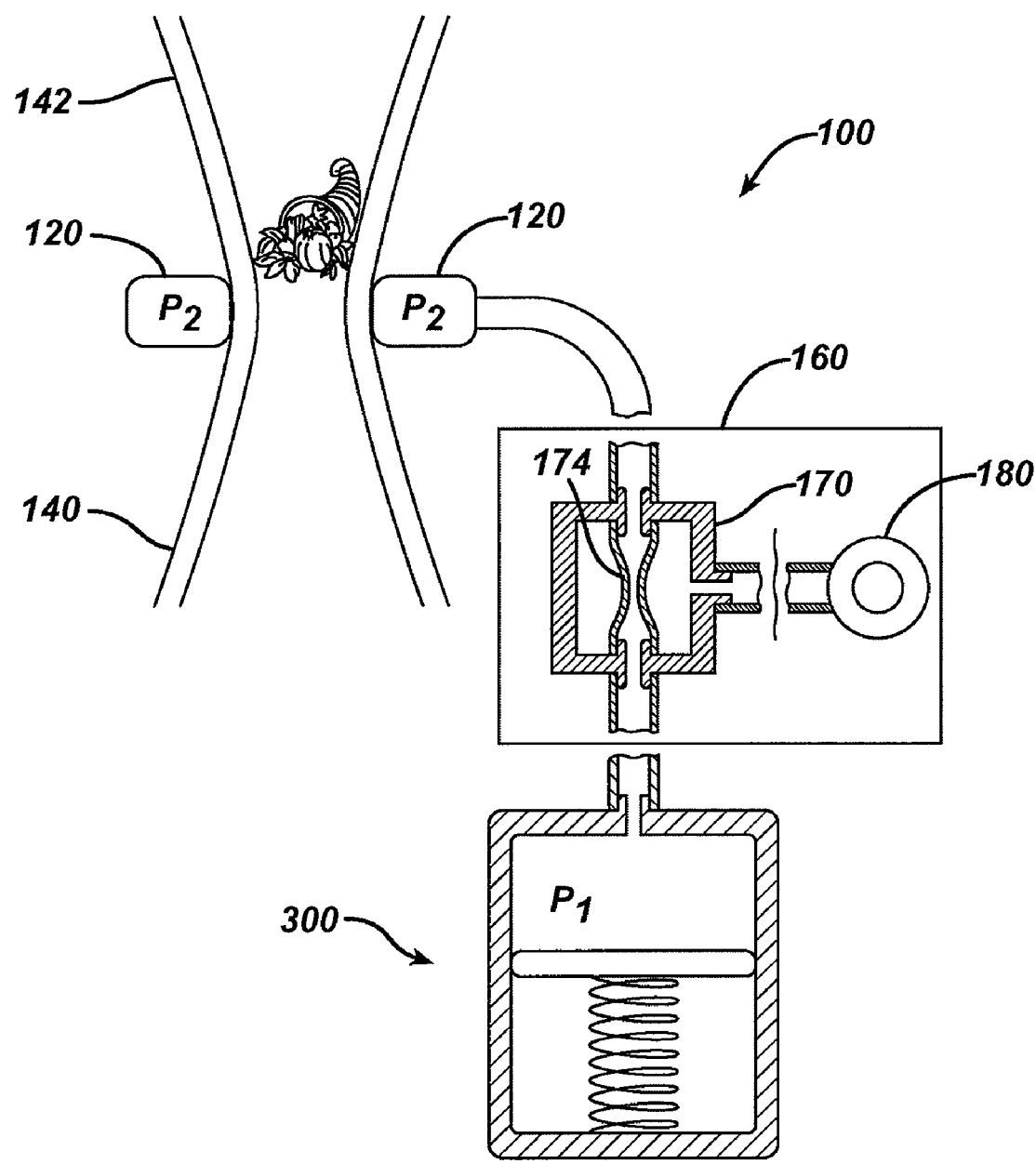
FIG. 17 is a schematic diagram of the food intake restriction system of FIG. 16 in use in a force stage following the dormant stage of FIG. 16.
Figure 18:
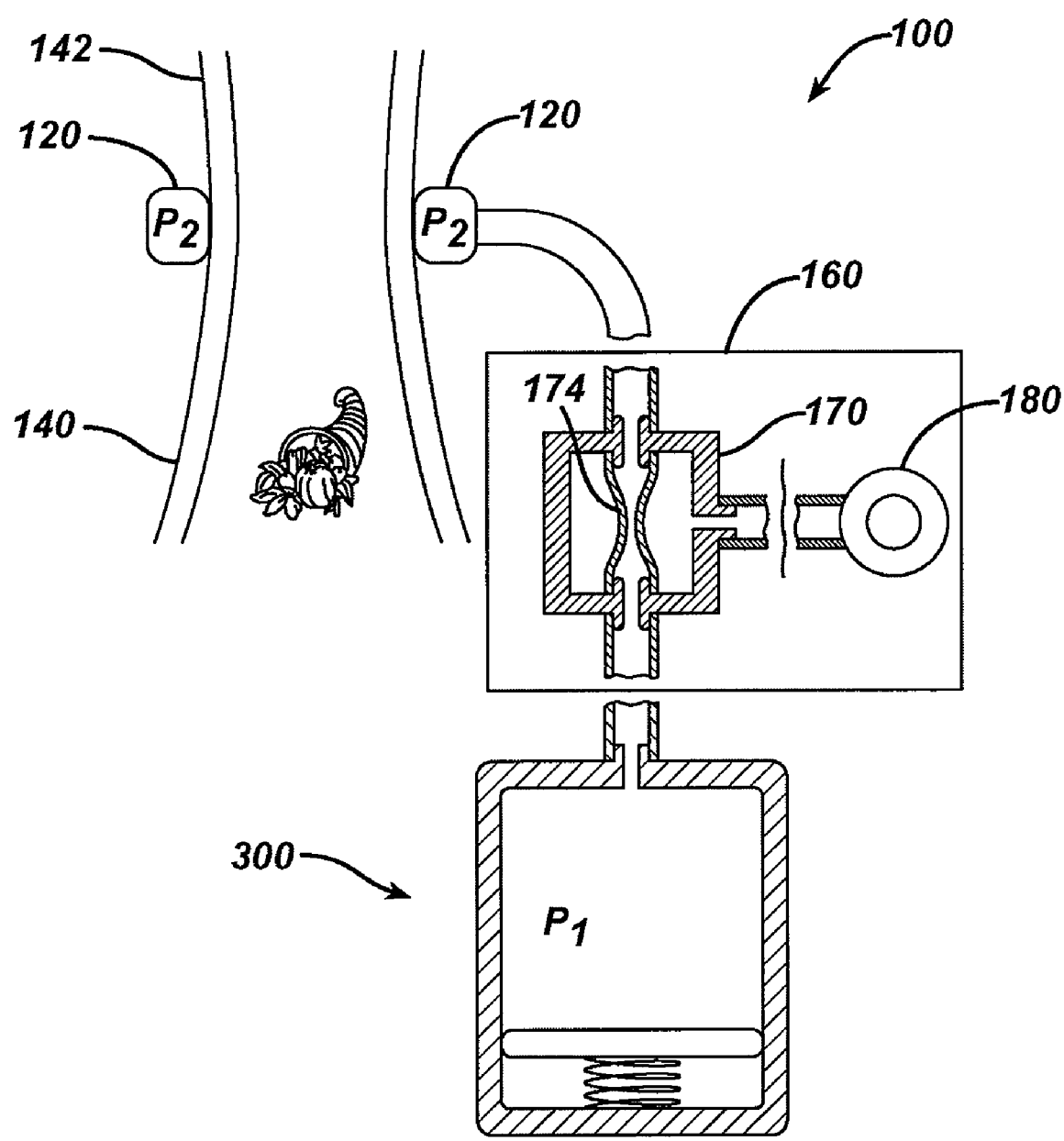
FIG. 18 is a schematic diagram of the food intake restriction system of FIG. 16 in use following the force stage of FIG. 17.

FIGS. 16-18 show one embodiment of the restriction system 100 in use. In the embodiment illustrated in FIGS. 16-18, the system 100 includes the pressured fluid source 300 of FIG. 3A and the flow control mechanism 160 of FIGS. 5-8 with the fluid conduit 174 having an adjustable diameter D. As shown, the fluid conduit's diameter 174 has the decreased diameter $D_D$ of FIG. 8. In a dormant stage shown in FIG. 16, the band 120 substantially closes the stoma opening in the stomach 140, e.g., the stoma is in a dormant position because substantially no forces are acting on the stoma (aside from the force of the band 120 to substantially close the stoma). In other words, the patient is not eating, drinking, swallowing, vomiting, or otherwise voluntarily or involuntarily exerting a force on the esophagus 142, the stomach 140, and/or the band 120. In the dormant stage, fluid from the fluid source 300 substantially fills the band 120. In other words, the system 100 is in equilibrium. Additionally, fluid within the system 100 is stationary, e.g., fluid is not flowing through the flow control mechanism 160 between the band 120 and the fluid source 300.

When a force acts on the stoma (e.g., peristaltic waves from the patient ingesting food and swallowing), such as in a force stage shown in FIG. 17, the force can create a higher pressure $P_2$ in the band 120 than the pressure $P_1$ of the fluid source 300. Such a pressure differential ($P_2 > P_1$) can influence the pressure control mechanism 130 to allow fluid in the band 120 to flow from the band 120 toward the fluid source 300 via the flow control mechanism 160. As discussed above, the diameter D of the fluid conduit 174 can regulate the flow rate of fluid between the band 120 and the fluid source 300, thus regulating the rate at which the pressure changes. Because patient satiety is substantially determined by an amount of time it takes fluid in the band 120 to flow from the band 120 toward the fluid source 300, and hence an amount of time it takes for food to pass through the stoma (or be naturally digested before passing through the stoma), the decreased diameter $D_D$ can allow for the patient to more quickly feel satiated and to feel satiated for a longer period of time because the flow rate through the control mechanism 160 is less than it would be through connective coupling of a substantially constant diameter between the band 120 and the fluid source 300. Similarly, if the diameter of the fluid conduit 174 was at the increased diameter $D_I$ of FIG. 7, the patient would feel satiated less quickly and for a shorter period of time because fluid would flow more quickly through the flow control mechanism 160 from the band 120 toward the fluid source 300. As such, a physician (or other authorized person) can adjust the diameter of the fluid conduit 174 any number of times over the course of the patient's treatment with the band 120 to, for example, provide for appropriate satiety of the patient. In other words, adjusting the diameter of the fluid conduit 174 can reduce or prevent rapid pressure changes in the band 120 that can reduce efficacy of the band 120 and affect a patient's eating patterns and/or overall weight control.

When the pressure control mechanism 130 has allowed enough fluid to flow from the band 120 toward the fluid source 300 via the fluid conduit 174, restriction of the stomach 140 by the band 120 can be sufficiently low so as to allow passage of food through the stoma, as shown in a passage stage in FIG. 18. The patient's satiety level thereby decreases. When the force stops acting on the stoma (e.g., the patient stops eating), the pressure differential can reverse such that the pressure $P_2$ of fluid in the band 120 is less than the pressure $P_1$ of fluid in the fluid source 120, thereby allowing fluid to flow from the fluid source 300 toward the band 120.

Figure 19A:
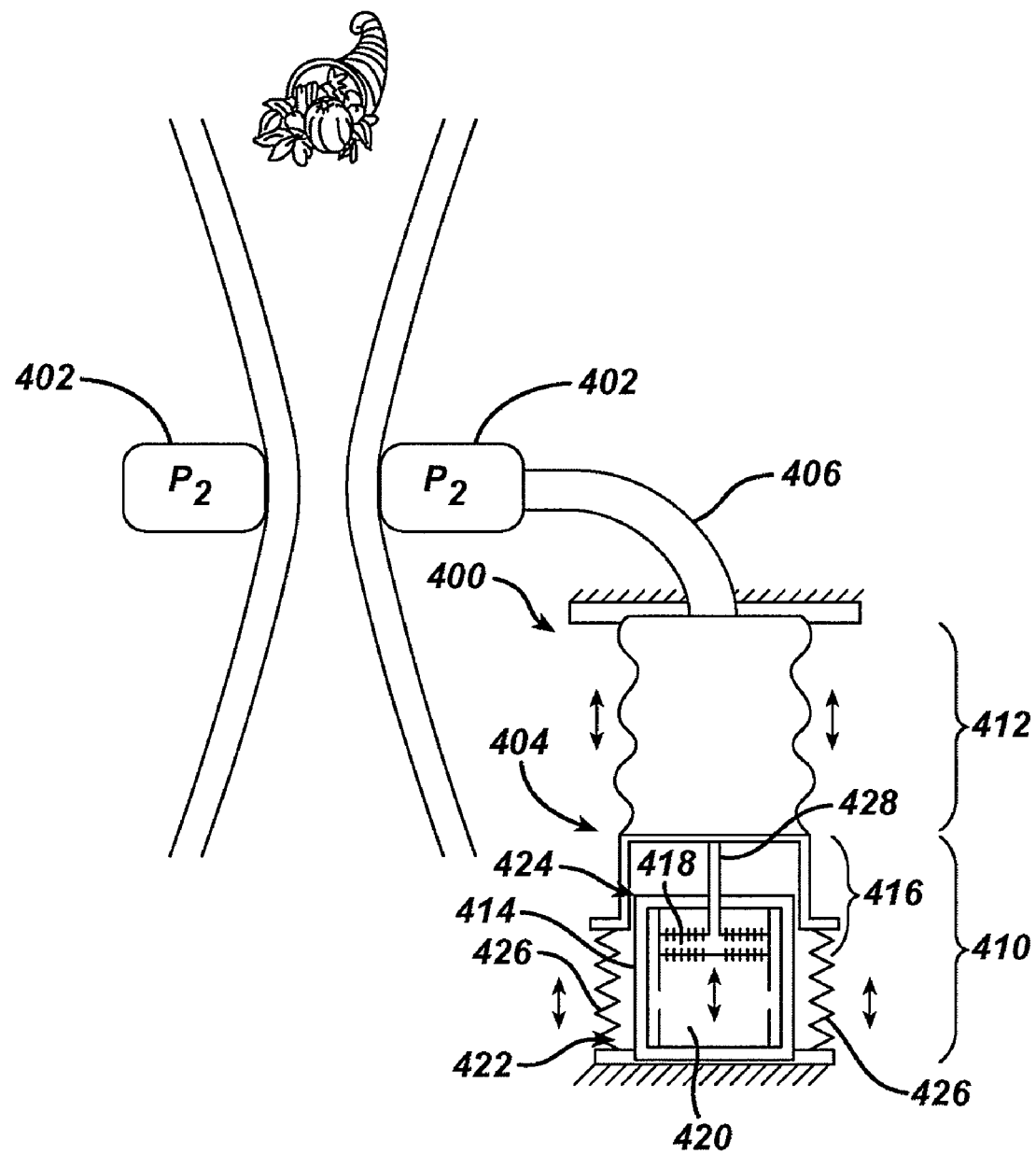
FIG. 19A is a schematic diagram of another food intake restriction system in use.

In another embodiment, rather than altering the geometry of the flow control mechanism to adjust the rate of the fluid flow between a fluid source and a restriction device, a biasing mechanism can be used to define the flow rate through the flow control mechanism. FIG. 19A illustrates a flow control mechanism 410 coupled to a fluid source 412 for regulating fluid flow between the fluid source 412 and a restriction device 402. The flow control mechanism 410 includes a biasing mechanism, namely a fluid-filled housing 414, that controls a rate of movement of an actuator coupled to the fluid source 412. Movement of the actuator is effective to drive fluid between the fluid source 412 and the restriction device 402, and thus the rate of movement of the actuator corresponds to the rate of fluid flow between the fluid source 412 and the restriction device 402. The rate of movement can be adjusted, as discussed in more detail below. As will also be discussed in more detail, the flow control mechanism 410 can also include a pressure regulating mechanism for regulating a pressure of the restriction device 402.

As shown in FIG. 19A, the fluid source 412 is in the form of a bellows (although the fluid source can have a variety of configurations, as discussed above) that is in fluid communication with the restriction device 402 via a catheter 406. One end 400 of the bellows is fixed to a housing, while another end 404 is coupled to an actuator 416. The actuator 416 can have a variety of configurations, but as shown, the actuator 416 includes a rigid rod 428 coupled at one end to the fluid source 412 and at its other end to a porous member 418 (e.g., mesh, a porous membrane, a disc having a plurality of holes formed therein, or any other porous composition allowing fluid to flow therethrough) disposed within the fluid-filled housing 414. Movement of the porous member 418 within the fluid-filled housing 414 can control a rate of fluid flow between the restriction device 402 and the fluid source 412. The porous member 418 can move at a certain rate through the fluid-filled housing 414 depending on various factors, such as the shape and size of the rod 428 and the porous member 418 and the type of fluid 420 contained in the fluid-filled housing 414. The fluid 420 in the housing 414 can flow through the porous member 418 to regulate a rate of movement of the porous member 418 through the housing 414 to thereby also regulate a rate of movement of the rod 428 and hence the rate of fluid flow between the fluid source 412 and the restriction device 402. As the porous member 418 moves toward a distal end 422 of the fluid-filled housing 414, the fluid source 412 is expanded and hence fluid flows from the band 402 toward the fluid source 412 to decrease an amount of fluid in the restriction device 402. Similarly, as the porous member 418 moves toward a proximal end 424 of the fluid-filled housing 414, the fluid source 412 contracts to cause fluid to flow toward the restriction device 402 from the fluid source 412 to increase an amount of fluid in the restriction device 402.

A rate of movement of the porous member 418 through the fluid 420 can be controlled by the configuration of the porous member 418 (e.g., size and number of holes through which fluid can flow) and by the fluid's composition (e.g., a viscosity of the fluid). The fluid-filled housing 414 can optionally be in fluid communication with a port, as previously described, to allow the fluid 420 in the fluid-filled housing 414 to be replaced with fluid having a different viscosity to adjust the rate of the actuator's movement through the housing 414. Generally, the more viscous the fluid 420, the slower the rate at which the porous member 418 can move through the fluid 420.

The actuator 416 can also be coupled to a spring 426 that can regulate the fluid pressure in the restriction device 402. The spring 426 can provide a biasing force to the fluid source 412 to respond to pressure changes in the restriction device, as described in more detail in previously mentioned U.S. application Ser. No. 11/965,322 entitled "Constant Force Mechanisms For Regulating Restriction Devices," filed on Dec. 27, 2007. The spring's biasing force can be internally or externally adjusted, and the spring 428 can be replaceable.

Figure 19B:
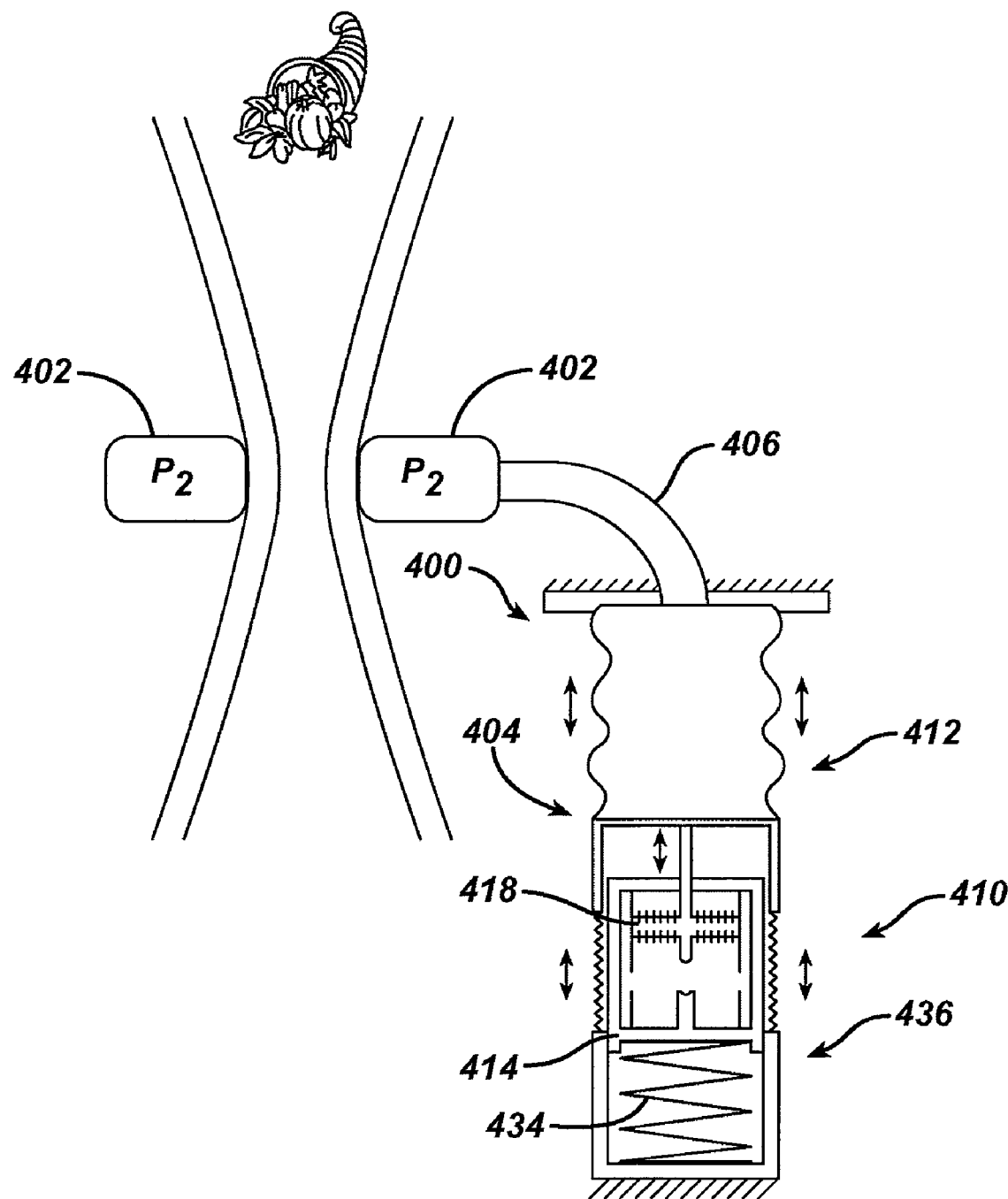
FIG. 19B is a schematic diagram of an alternate version of the food intake restriction system of FIG. 19A.

In another embodiment, shown in FIG. 19B, the flow control mechanism 410 can include a second spring 434 coupled to a distal end 436 of the fluid-filled housing 414. When the porous member 418 disposed within the fluid-filled housing 414 is in a distal-most position adjacent to the housing's distal end 436, the spring 434 can allow the fluid source 412 to further expand, e.g., to continue to allow fluid to flow from the restriction device 402 toward the fluid source 412.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method of forming a restriction in a patient, comprising:
    implanting a gastric restriction device around a stomach to form a restriction that corresponds to a volume of fluid in the restriction device, and the restriction device receiving fluid from and delivering fluid to a fluid source at a flow rate defined by a geometry of a flow control mechanism in fluid communication with and disposed between the restriction device and the fluid source; adjusting the geometry of the flow control mechanism to adjust the flow rate; wherein the flow control mechanism includes a flexible tube disposed within an internal cavity of a housing body having exterior walls that are flexible; wherein adjusting a geometry of the flexible tube comprises modifying an amount of a second fluid within the internal cavity to deform the exterior walls of the housing body and to change a longitudinal length of the flexible tube.

2. The method of claim 1, wherein a pathway of the flexible tube through which the fluid flows between the restriction device and the fluid source is not in fluid communication with the internal cavity such that modifying the amount of the second fluid within the internal cavity does not alter an amount of the fluid available to flow between the restriction device and the fluid source.

3. The method of claim 1, wherein modifying the amount of the second fluid changes a diameter of the flexible tube to adjust the geometry of the flexible tube.

4. The method of claim 1, wherein modifying the amount of the second fluid comprises removing at least some of the second fluid from the internal cavity to decrease the longitudinal length of the flexible tube and increase the flow rate.

5. The method of claim 4, wherein removing at least some of the second fluid from the internal cavity increases a diameter of the flexible tube.

6. The method of claim 1, wherein modifying the amount of the second fluid comprises introducing fluid to the internal cavity to increase the longitudinal length of the flexible tube and decrease the flow rate.

7. The method of claim 6, wherein introducing fluid to the internal cavity decreases a diameter of the flexible tube.

* * * * *